(12) United States Patent
Rawat et al.

(10) Patent No.: US 9,884,825 B2
(45) Date of Patent: Feb. 6, 2018

(54) CURCUMIN ANALOGS AND METHODS OF MAKING AND USING THEREOF

(71) Applicants: Georgia State University Research Foundation, Inc., Atlanta, GA (US); University of Delhi, Delhi (IN)

(72) Inventors: Diwan S. Rawat, Delhi (IN); Binghe Wang, Marietta, GA (US); Nitin Kumar, Delhi (IN); Sunny Manohar, Delhi (IN); Xiaochuan Yang, Towson, MD (US); Guojing Sun, Atlanta, GA (US); Nanting Ni, Ventura, CA (US)

(73) Assignees: Georgia State University Research Foundation, Inc., Atlanta, GA (US); University of Delhi, Delhi (IN)

( * ) Notice: Subject to any disclaimer, the term of this patent is extended or adjusted under 35 U.S.C. 154(b) by 0 days.

(21) Appl. No.: 14/418,025

(22) PCT Filed: Aug. 1, 2013

(86) PCT No.: PCT/US2013/053216
§ 371 (c)(1),
(2) Date: Jan. 28, 2015

(87) PCT Pub. No.: WO2014/022660
PCT Pub. Date: Feb. 6, 2014

(65) Prior Publication Data
US 2015/0152056 A1 Jun. 4, 2015

Related U.S. Application Data

(60) Provisional application No. 61/679,233, filed on Aug. 3, 2012.

(51) Int. Cl.
| | |
|---|---|
| *C07D 213/68* | (2006.01) |
| *C07D 401/14* | (2006.01) |
| *C07D 213/89* | (2006.01) |
| *C07D 401/06* | (2006.01) |
| *C07C 49/753* | (2006.01) |
| *C07C 225/18* | (2006.01) |
| *C07D 233/61* | (2006.01) |
| *C07D 295/116* | (2006.01) |

(52) U.S. Cl.
CPC .......... *C07D 213/68* (2013.01); *C07C 49/753* (2013.01); *C07C 225/18* (2013.01); *C07D 213/89* (2013.01); *C07D 233/61* (2013.01); *C07D 295/116* (2013.01); *C07D 401/06* (2013.01); *C07D 401/14* (2013.01); *C07C 2601/08* (2017.05)

(58) Field of Classification Search
CPC .. C07D 213/68; C07D 213/69; C07D 401/14; C07D 295/116; C07D 233/61; C07C 49/753; C07C 225/18; C07C 2101/08
See application file for complete search history.

(56) References Cited

U.S. PATENT DOCUMENTS

| | | | | |
|---|---|---|---|---|
| 3,852,279 | A | * | 12/1974 | Krapcho et al. ............. 546/119 |
| 3,923,816 | A | | 12/1975 | Krapcho |
| 4,065,617 | A | | 12/1977 | Krapcho |
| 4,085,102 | A | | 4/1978 | Krapcho |
| 4,177,271 | A | | 12/1979 | Vallet |
| 4,282,353 | A | * | 8/1981 | Green .................. C07D 303/22 549/219 |
| 5,811,218 | A | | 9/1998 | Kaji |
| 6,939,479 | B2 | * | 9/2005 | Farrand ................. C07C 45/673 252/299.01 |
| 2003/0092772 | A1 | | 5/2003 | Reksohadiprodjo |
| 2006/0276536 | A1 | | 12/2006 | VanderJagt |
| 2007/0010488 | A1 | | 1/2007 | Youssef |
| 2009/0011991 | A1 | | 1/2009 | Shoji |
| 2012/0046247 | A1 | | 2/2012 | Shih |

FOREIGN PATENT DOCUMENTS

| | | |
|---|---|---|
| EP | 0243159 | 10/1987 |
| EP | 0295044 | 12/1988 |
| EP | 0359431 | 3/1990 |
| EP | 0369645 | 5/1990 |
| GB | 1472325 | 6/1974 |

(Continued)

OTHER PUBLICATIONS

Buu-Hoi et al., 12 Bulletin De La Societe Chimique De France 3096-9 (1964) (CAS Abstract).*

(Continued)

*Primary Examiner* — Timothy R Rozof
(74) *Attorney, Agent, or Firm* — Pabst Patent Group LLP

(57) ABSTRACT

Compounds having Formula I or II, and methods of making and using thereof, are described herein:

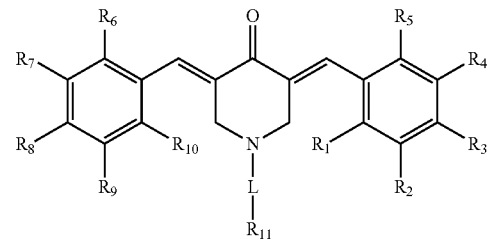

Formula I

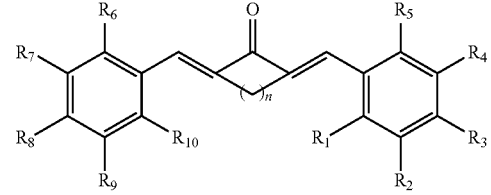

Formula II

22 Claims, 9 Drawing Sheets

(56) References Cited

FOREIGN PATENT DOCUMENTS

| | | |
|---|---|---|
| WO | 9117749 | 11/1991 |
| WO | 9301824 | 2/1993 |
| WO | 0140188 | 6/2001 |
| WO | 0146110 | 6/2001 |
| WO | 02095361 | 11/2002 |
| WO | 2005025623 | 3/2005 |
| WO | 2005063774 | 7/2005 |
| WO | 2007059613 | 5/2007 |
| WO | 2011005790 | 1/2011 |
| WO | 2012021692 | 2/2012 |

OTHER PUBLICATIONS

Barbulescu et al., 23(1) Revistade Chimie (Bucharest, Romania) 6-9 (1972) (CAS Abstract).*
Mirza et al., A27(1) J. Macromolecular Sci., Chem., 1-22 (1990) (CAS Abstract).*
McElvain et al., 70 J. Am. Chem. Soc. 1820-5 (1948) (CAS Abstr.).*
International Search Report for PCT/US2013/053216 dated Nov. 8, 2013.

* cited by examiner

CURCUMIN ANALOGS AND METHODS OF MAKING AND USING THEREOF

STATEMENT REGARDING FEDERALLY SPONSORED RESEARCH OR DEVELOPMENT

This invention was made with Government Support under Agreement Nos. GM086925 and GM084933 awarded to Binghe Wang by the National Institutes of Health. The Government has certain rights in the invention.

FIELD OF THE INVENTION

This invention is in the field of curcumin analogs, particularly C5 curcumin analogs, pharmaceutical compositions containing the same, and methods of using thereof.

BACKGROUND OF THE INVENTION

Turmeric has been used since ancient times in India and China as a dietary pigment and essential spice. It is also used in traditional/folk medicine as an antiseptic and anti-inflammatory agent and in wound healing. Curcumin has been identified as the active ingredient in turmeric. It is a yellow colored polyphenolic natural compound isolated from the rhizome of the herb *Curcuma longa* Linn which exhibits various biological activities including anti-inflammatory, antioxidant, antimicrobial, antiviral, chemopreventive, anti-angiogenic, and anticancer activities. Curcumin has also shown hepato-protective and nephro-protective, thrombosis supressing, myocardial infarction protective, hypoglycemic, and antirheumatic activities.

Curcumin exhibits this wide range of biological activities due to its unique ability to interact with various biomolecules and biochemical pathways, which include cell proliferation pathways, caspase activation pathways, tumor suppressor pathways, transcriptional factors, cell survival pathways, mitochondrial pathways, protein kinase pathways, and death receptor pathways. The multi-targeting ability of curcumin has made it a focus for cancer chemoprevention and pharmacotherapy.

Toxicological studies conducted in animal models or in humans have shown that curcumin is safe even at a dose level of 12 g/d. The pharmacological safety and efficacy of curcumin makes it a potential compound for treatment and prevention of a wide variety of diseases. However, the poor solubility, poor bioavailability, and poor absorption as well as rapid metabolism are major problems associated with curcumin. Consequently, curcumin itself is not a good candidate for further clinical development. Much effort has been devoted to developing new curcumin analogues in order to solve the pharmacokinetic problems and at the same time to maintain high potency and low toxicity. Efforts have also been made to enhance its selectivity and potency for addressing the pathological diversity of human cancer.

In order to address these issues, numerous approaches have been explored to synthesize curcumin analogues and derivatives. The pharmacological studies conducted on curcumin indicate that the β-diketone functionality of curcumin is a substrate for liver aldoketo reductases and this may be a metabolism of curcumin in vivo. In order to improve the in vivo metabolic stability of curcumin (e.g., C7 curcuminoids), several curcumin analogues with a single carbonyl moiety (e.g., C5 curcuminoids) have been prepared and some of these compounds have exhibited anticancer activity.

The degree of in vivo degradation and pharmacokinetic studies suggest that these compounds are more stable and exhibit increased activity compared to curcumin. Structure activity relationship studies conducted on these compounds revealed that the heteroaromatic core in these compounds correlated with high anti-proliferative and anti-inflammatory activities.

There exists a need for the synthesis of new C5 curcumin analogues, which are stable, bioavailable, and exhibit the desired biological activity.

Accordingly, it is an object of the invention to provide new stable, bioavailable C5 curcumin analogues and exhibit the desired biological activity, and methods of making and using thereof.

SUMMARY OF THE INVENTION

The compounds described herein are compounds of Formula

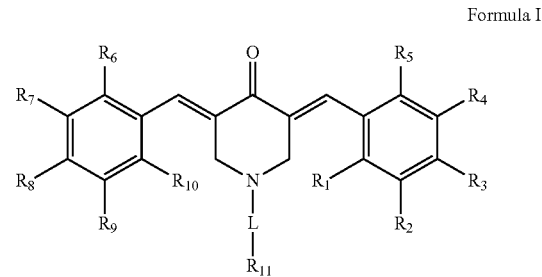

Formula I $R_1$-$R_{10}$ are independently absent or selected from the group consisting of substituted or unsubstituted, linear, branched, or cyclic alkyl, alkenyl, or alkynyl; halogen, substituted or unsubstituted aryl or heteroaryl, substituted or unsubstituted alkoxy; hydroxy, cyano, formyl, acyl, carboxylic acid (—COOH), carboxylate (—COO⁻), primary amide (e.g., —CONH$_2$), secondary amide (e.g., —CONHR$_{12}$), tertiary amide (e.g., —CONR$_{12}$R$_{12}$), secondary carbamate (e.g., —OCONHR$_{12}$; —NHCOOR$_{12}$), tertiary carbamate (e.g., —OCONR$_{12}$R$_{12}$; —NR$_{12}$COOR$_{12}$), urea (e.g., —NHCONHR$_{12}$; —NR$_{12}$CONHR$_{12}$; —NHCONR$_{12}$R$_{12}$, —NR$_{12}$CONR$_{12}$R$_{12}$), carbinol (e.g., —CH$_2$OH; —CHR$_{12}$OH, —CR$_{12}$R$_{12}$OH), ester (e.g., —COOR$_{12}$), thiol (—SH), primary amine (—NH$_2$), secondary amine (e.g., —NHR$_{12}$), tertiary amine (e.g., —NR$_{12}$R$_{12}$), thioether (e.g., —SR$_{12}$), AND sulfinyl group (e.g., —SOR$_{12}$), sulfonyl group (e.g., —SOOR$_{12}$).

$R_{11}$ is substituted or unsubstituted alkyl, cycloalkyl, alkenyl, cycloalkenyl, or alkynyl; substituted or unsubstituted benzyl sulfonyl (Bnz); substituted or unsubstituted p-toluene sulfonyl (p-Ts); substituted or unsubstituted benzyl; substituted or unsubstituted aryl; substituted or unsubstituted heteroaryl; wherein the $R_{11}$ if substituted, can be substituted with one or more of alkyl, cycloalkyl, alkenyl, cycloalkenyl, alkoxy, amine, halogen, hydroxyl, nitrile, CF$_3$, ester, amide, urea, carbamate, thioether, carboxylic acid, and aryl; and L is a linker or spacer.

In some embodiments, $R_{11}$ is unsubstituted alkyl, such as methyl, ethyl, or propyl. In some embodiments, $R_{11}$ is unsubstituted ethyl and at least one of $R_1$-$R_5$ and at least one of $R_6$-$R_{10}$ are halogen (e.g., Br, Cl, or F). In particular embodiments, $R_{11}$ and $R_8$ are halogen and $R_1$, $R_2$, $R_4$-$R_7$, $R_9$, and $R_{10}$ are hydrogen. In more particular embodiments, $R_3$ and $R_8$ are the same halogen. In still other embodiments, $R_{11}$ is unsubstituted ethyl and at least one of $R_1$-$R_5$ and at least one of $R_6$-$R_{10}$ are unsubstituted alkyl, such as methyl, ethyl, n-propyl, isopropyl, n-butyl, or t-butyl. In particular embodiments, $R_3$ and $R_8$ are unsubstituted alkyl and $R_1$, $R_2$, $R_4$-$R_7$, $R_9$, and $R_{10}$ are hydrogen. In more particular embodiments, $R_3$ and $R_8$ are the same unsubstituted alkyl. In still other embodiments, $R_{11}$ is unsubstituted ethyl and at least one of $R_1$-$R_5$ and at least one of $R_6$-$R_{10}$ are unsubstituted alkoxy, such as methoxy. In particular embodiments, $R_3$ and $R_8$ are unsubstituted alkoxy and $R_1$, $R_2$, $R_4$-$R_7$, $R_9$, and $R_{10}$ are hydrogen. In more particular embodiments, $R_3$ and $R_8$ are the same unsubstituted alkoxy.

In other embodiments, $R_{11}$ is unsubstituted p-toluene sulfonyl. In some embodiments, $R_{11}$ is unsubstituted p-toluene sulfonyl and at least one of $R_1$-$R_5$ and at least one of $R_6$-$R_{10}$ are halogen (e.g., Br, Cl, or F). In particular embodiments, $R_3$ and $R_8$ are halogen and $R_1$, $R_2$, $R_4$-$R_7$, $R_9$, and $R_{10}$ are hydrogen. In more particular embodiments, $R_3$ and $R_8$ are the same halogen. In still other embodiments, $R_{11}$ is unsubstituted p-toluene sulfonyl and at least one of $R_1$-$R_5$ and at least one of $R_6$-$R_{10}$ are unsubstituted alkyl, such as methyl, ethyl, n-propyl, isopropyl, n-butyl, or t-butyl. In particular embodiments, $R_3$ and $R_8$ are unsubstituted alkyl and $R_1$, $R_2$, $R_4$-$R_7$, $R_9$, and $R_{10}$ are hydrogen. In more particular embodiments, $R_3$ and $R_8$ are the same unsubstituted alkyl. In still other embodiments, $R_{11}$ is unsubstituted p-toluene sulfonyl and at least one of $R_1$-$R_5$ and at least one of $R_6$-$R_{10}$ are unsubstituted alkoxy, such as methoxy. In particular embodiments, $R_3$ and $R_8$ are unsubstituted alkoxy and $R_1$, $R_2$, $R_4$-$R_7$, $R_9$, and $R_{10}$ are hydrogen. In more particular embodiments, $R_3$ and $R_8$ are the same unsubstituted alkoxy.

In other embodiments, $R_{11}$ is unsubstituted benzyl. In some embodiments, $R_{11}$ is unsubstituted benzyl and at least one of $R_1$-$R_5$ and at least one of $R_6$-$R_{10}$ are halogen (e.g., Br, Cl, or F). In particular embodiments, $R_3$ and $R_8$ are halogen and $R_1$, $R_2$, $R_4$-$R_7$, $R_9$, and $R_{10}$ are hydrogen. In more particular embodiments, $R_3$ and $R_8$ are the same halogen. In still other embodiments, $R_{11}$ is unsubstituted benzyl and at least one of $R_1$-$R_5$ and at least one of $R_6$-$R_{10}$ are unsubstituted alkyl, such as methyl, ethyl, n-propyl, isopropyl, n-butyl, or t-butyl. In particular embodiments, $R_3$ and $R_8$ are unsubstituted alkyl and $R_1$, $R_2$, $R_4$-$R_7$, $R_9$, and $R_{10}$ are hydrogen. In more particular embodiments, $R_3$ and $R_8$ are the same unsubstituted alkyl. In still other embodiments, $R_{11}$ is unsubstituted benzyl and at least one of $R_1$-$R_5$ and at least one of $R_6$-$R_{10}$ are unsubstituted alkoxy, such as methoxy. In particular embodiments, $R_3$ and $R_8$ are unsubstituted alkoxy and $R_1$, $R_2$, $R_4$-$R_7$, $R_9$, and $R_{10}$ are hydrogen. In more particular embodiments, $R_3$ and $R_8$ are the same unsubstituted alkoxy.

In other embodiments, $R_{11}$ is unsubstituted benzyl sulfonyl. In some embodiments, $R_{11}$ is unsubstituted benzyl sulfonyl, at least one of $R_1$-$R_5$ and at least one of $R_6$-$R_{10}$ are halogen (e.g., Br, Cl, or F). In particular embodiments, $R_3$ and $R_8$ are halogen and $R_1$, $R_2$, $R_4$-$R_7$, $R_9$, and $R_{10}$ are hydrogen. In more particular embodiments, $R_3$ and $R_8$ are the same halogen. In still other embodiments, $R_{11}$ is unsubstituted benzyl sulfonyl and at least one of $R_1$-$R_5$ and at least one of $R_6$-$R_{10}$ are unsubstituted alkyl, such as methyl, ethyl, n-propyl, isopropyl, n-butyl, or t-butyl. In particular embodiments, $R_3$ and $R_8$ are unsubstituted alkyl and $R_1$, $R_2$, $R_4$-$R_7$, $R_9$, and $R_{10}$ are hydrogen. In more particular embodiments, $R_3$ and $R_8$ are the same unsubstituted alkyl. In still other embodiments, $R_{11}$ is unsubstituted benzyl sulfonyl and at least one of $R_1$-$R_5$ and at least one of $R_6$-$R_{10}$ are unsubstituted alkoxy, such as methoxy. In particular embodiments, $R_3$ and $R_8$ are unsubstituted alkoxy and $R_1$, $R_2$, $R_4$-$R_7$, $R_9$, and $R_{10}$ are hydrogen. In more particular embodiments, $R_3$ and $R_8$ are the same unsubstituted alkoxy.

In still other embodiments, L is present and $R_{11}$ is a substituted or unsubstituted aryl or heteroaryl group. In particular embodiments, L is a substituted or unsubstituted alkylene group, such as a methylene group, and $R_{11}$ is a substituted or unsubstituted triazole. In some embodiments, L is an alkylene groups, such as substituted or unsubstituted methylene linker and $R_{11}$ is a triazole group, such as

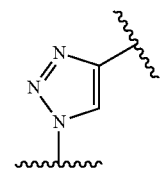

wherein L is attached to the triazole group at the C5 position. In some embodiments, the triazole ring is substituted at the nitrogen as shown above. In particular embodiments, the triazole ring is substituted with a substituted alkyl group. In more particular embodiments, the alkyl group is substituted as shown below:

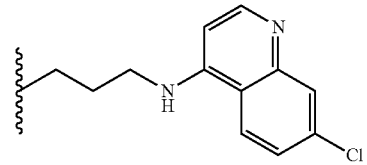 [SMILES: *CCCNc1ccnc2cc(Cl)ccc12]

In still other embodiments, the compound has the following formula:

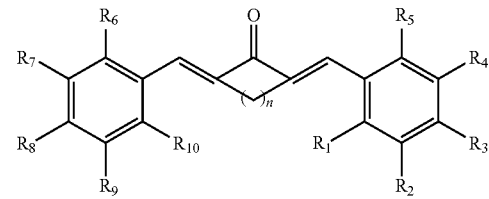

wherein $R_1$-$R_{10}$ are independently absent or selected from the group consisting of substituted or unsubstituted, linear, branched, or cyclic alkyl, alkenyl, or alkynyl; halogen, substituted or unsubstituted aryl or heteroaryl, substituted or unsubstituted alkoxy; hydroxy, cyano, formyl, acyl, carboxylic acid (—COOH), carboxylate (—COO⁻), primary amide (e.g., —CONH$_2$), secondary amide (e.g., —CONHR$_{12}$), tertiary amide (e.g., —CONR$_{12}$R$_{12}$), secondary carbamate (e.g., —OCONHR$_{12}$; —NHCOOR$_{12}$), tertiary carbamate (e.g., —OCONR$_{12}$R$_{12}$; —NR$_{12}$COOR$_{12}$), urea (e.g., —NHCONHR$_{12}$; —NR$_{12}$CONHR$_{12}$; —NHCONR$_{12}$R$_{12}$, —NR$_{12}$CONR$_{12}$R$_{12}$), carbinol (e.g., —CH$_2$OH; —CHR$_{12}$OH, —CR$_{12}$R$_{12}$OH), ester (e.g., —COOR$_{12}$), thiol (—SH), primary amine (—NH$_2$), secondary amine (e.g., —NHR$_{12}$), tertiary amine (e.g., —NR$_{12}$R$_{12}$), thioether (e.g., —SR$_{12}$), sulfinyl group (e.g., —SOR$_{12}$), sulfonyl group (e.g., —SOOR$_{12}$), provided that $R_3$ and $R_8$ are substituted alkoxy, such as —O(CH$_2$)$_m$X, where X is halogen or an aromatic or non-aromatic heterocyclic ring, such as

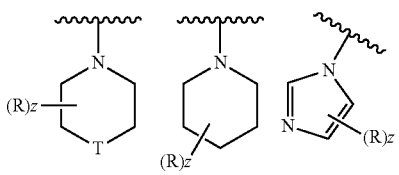

wherein

T is O, S, or NR$_{11}$, wherein each occurrence of R and R$_{11}$ is defined as above form R$_1$-R$_{10}$;

n=0, 2, 3, or 4;

m is an integer from 0-10; and z, as valence permits, is an integer from 0-10.

The compound(s) can be formulated with one or more pharmaceutically acceptable carriers and/or excipients to prepare pharmaceutical compositions. The compositions can be formulated for enteral (e.g., oral), parenteral (e.g., intravenous), topical, or transdermal administration.

The compounds can be administered to treat a proliferative disease, such as cancer. The compounds described herein showed significant cytotoxicity against cancer cells, such as human cervical cancer cells (HeLa)

DETAILED DESCRIPTION OF THE INVENTION

I. Definitions

Figure 1:
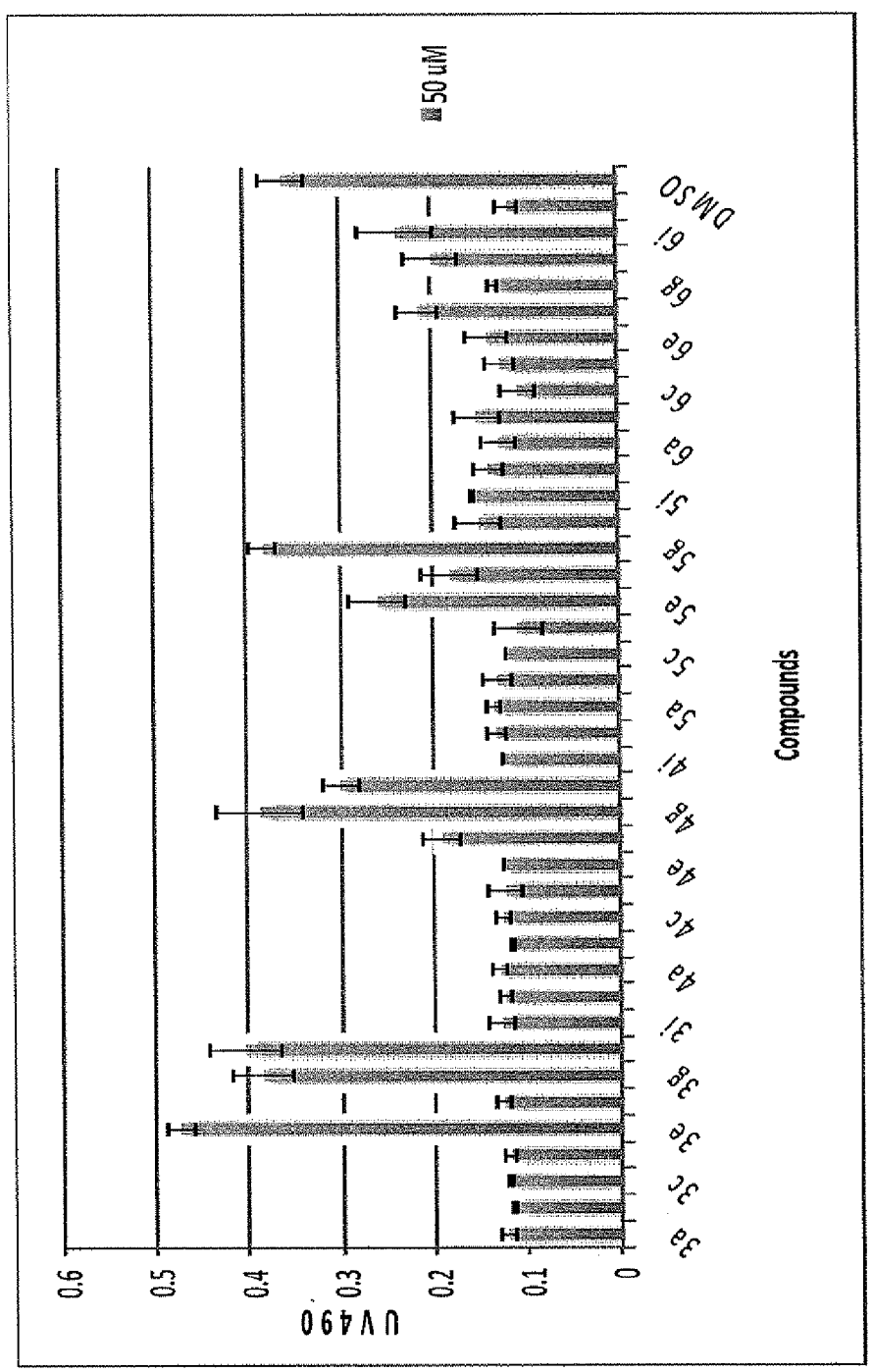
FIG. 1 is a bar graph showing the cytotoxicity (fraction of cell survival) of curcumin analogues in Hela cells using the MTT assay at 50 µM. Data represent average values of three replicates.

An "effective amount", e.g., of the compounds described herein, refers to an amount of the compound in a composition or formulation which, when applied as part of a desired dosage regimen brings about, e.g., a change in the rate of cell proliferation and/or the state of differentiation of a cell and/or rate of survival of a cell according to clinically acceptable standards for the disorder to be treated.

The "growth state" of a cell refers to the rate of proliferation of the cell and/or the state of differentiation of the cell. An "altered growth state" is a growth state characterized by an abnormal rate of proliferation, e.g., a cell exhibiting an increased or decreased rate of proliferation relative to a normal cell.

The term "patient" or "subject" to be treated refers to either a human or non-human animal.

The term "prodrug", as used herein, refers to compounds that, under physiological conditions, are converted into the therapeutically active compound described herein. A common method for making a prodrug is to include selected moieties, which are hydrolyzed under physiological conditions to reveal the desired molecule. In other embodiments, the prodrug is converted by an enzymatic activity of the host animal.

As used herein, "proliferating" and "proliferation" refer to cells undergoing mitosis.

As generally used herein "pharmaceutically acceptable" refers to those compounds, materials, compositions, and/or dosage forms which are, within the scope of sound medical judgment, suitable for use in contact with the tissues, organs, and/or bodily fluids of human beings and animals without excessive toxicity, irritation, allergic response, or other problems or complications commensurate with a reasonable benefit/risk ratio.

"Stereoisomer", as used herein, refers to isomeric molecules that have the same molecular formula and sequence of bonded atoms (constitution), but which differ in the three dimensional orientations of their atoms in space. Examples of stereoisomers include enantiomers and diastereomers. As used herein, an enantiomer refers to one of the two mirror-image forms of an optically active or chiral molecule. Diastereomers (or diastereoisomers) are stereoisomers that are not enantiomers (non-superimposable mirror images of each other). Chiral molecules contain a chiral center, also referred to as a stereocenter or stereogenic center, which is any point, though not necessarily an atom, in a molecule bearing groups such that an interchanging of any two groups leads to a stereoisomer. In organic compounds, the chiral center is typically a carbon, phosphorus or sulfur atom, though it is also possible for other atoms to be stereocenters in organic and inorganic compounds. A molecule can have multiple stereocenters, giving it many stereoisomers. In compounds whose stereoisomerism is due to tetrahedral stereogenic centers (e.g., tetrahedral carbon), the total number of hypothetically possible stereoisomers will not exceed 2n, where n is the number of tetrahedral stereocenters. Molecules with symmetry frequently have fewer than the maximum possible number of stereoisomers. A 50:50 mixture of enantiomers is referred to as a racemic mixture. Alternatively, a mixture of enantiomers can be enantiomerically enriched so that one enantiomer is present in an amount greater than 50%. Enantiomers and/or diasteromers can be resolved or separated using techniques known in the art.

"Half maximal inhibitory concentration, IC$_{50}$", as used herein, refers to a measure of the effectiveness of a compound in inhibiting biological or biochemical function. This quantitative measure indicates how much of a particular drug or other substance (inhibitor) is needed to inhibit a given biological process (or component of a process, i.e. an enzyme, cell, cell receptor or microorganism) by half. According to the FDA, IC$_{50}$ represents the concentration of a drug that is required for 50% inhibition in vitro. The IC$_{50}$ can be determined using a variety of assays known in the art.

The term "alkyl" refers to the radical of saturated aliphatic groups, including straight-chain alkyl groups, branched-chain alkyl groups, cycloalkyl(alicyclic) groups, alkyl-substituted cycloalkyl groups, and cycloalkyl-substituted alkyl groups.

In preferred embodiments, a straight chain or branched chain alkyl has 30 or fewer carbon atoms in its backbone (e.g., $C_1$-$C_{30}$ for straight chains, $C_3$-$C_{30}$ for branched chains), and more preferably 20 or fewer. Likewise, preferred cycloalkyls have from 3-10 carbon atoms in their ring structure, and more preferably have 5, 6 or 7 carbons in the ring structure. The term "alkyl" (or "lower alkyl") as used throughout the specification, examples, and claims is intended to include both "unsubstituted alkyls" and "substituted alkyls", the latter of which refers to alkyl moieties having one or more substituents replacing a hydrogen on one or more carbons of the hydrocarbon backbone. Such substituents include, but are not limited to, halogen, hydroxyl, carbonyl (such as a carboxyl, alkoxycarbonyl, formyl, or an acyl), thiocarbonyl (such as a thioester, a thioacetate, or a thioformate), alkoxyl, phosphoryl, phosphate, phosphonate, a hosphinate, amino, amino, amidine, imine, cyano, nitro, azido, sulfhydryl, alkylthio, sulfate, sulfonate, sulfamoyl, sulfonamido, sulfonyl, heterocyclyl, aralkyl, or an aromatic or heteroaromatic moiety.

Unless the number of carbons is otherwise specified, "lower alkyl" as used herein means an alkyl group, as defined above, but having from one to ten carbons, more preferably from one to six carbon atoms in its backbone structure. Likewise, "lower alkenyl" and "lower alkynyl" have similar chain lengths. Throughout the application, preferred alkyl groups are lower alkyls. In preferred embodiments, a substituent designated herein as alkyl is a lower alkyl.

It will be understood by those skilled in the art that the moieties substituted on the hydrocarbon chain can themselves be substituted, if appropriate. For instance, the substituents of a substituted alkyl may include halogen, hydroxy, nitro, thiols, amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —$CF_3$, —CN and the like. Cycloalkyls can be substituted in the same manner.

The term "heteroalkyl", as used herein, refers to straight or branched chain, or cyclic carbon-containing radicals, or combinations thereof, containing at least one heteroatom. Suitable heteroatoms include, but are not limited to, O, N, Si, P, Se, B, and S, wherein the phosphorous and sulfur atoms are optionally oxidized, and the nitrogen heteroatom is optionally quaternized. Heteroalkyls can be substituted as defined above for alkyl groups.

The term "alkylthio" refers to an alkyl group, as defined above, having a sulfur radical attached thereto. In preferred embodiments, the "alkylthio" moiety is represented by one of —S-alkyl, —S-alkenyl, and —S-alkynyl. Representative alkylthio groups include methylthio, ethylthio, and the like. The term "alkylthio" also encompasses cycloalkyl groups, alkene and cycloalkene groups, and alkyne groups. "Arylthio" refers to aryl or heteroaryl groups.

The terms "alkenyl" and "alkynyl" refer to unsaturated aliphatic groups analogous in length and possible substitution to the alkyls described above, but that contain at least one double or triple bond respectively.

The terms "alkoxyl" or "alkoxy" as used herein refer to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as can be represented by one of —O-alkyl, —O-alkenyl, and —O-alkynyl. Aroxy can be represented by —O-aryl or O-heteroaryl, wherein aryl and heteroaryl are as defined below. The alkoxy and phenoxy groups can be substituted as described above for alkyl.

The terms "amine" and "amino" are art-recognized and refer to both unsubstituted and substituted amines, e.g., a moiety that can be represented by the general formula:

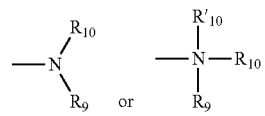

wherein, $R_9$, $R_{10}$, and $R'_{10}$ each independently represent a hydrogen, an alkyl, an alkenyl, —$(CH_2)_m$—$R_8$ or $R_9$ and $R_{10}$ taken together with the N atom to which they are attached complete a heterocycle having from 4 to 8 atoms in the ring structure; $R_8$ represents an aryl, a cycloalkyl, a cycloalkenyl, a heterocycle or a polycycle; and m is zero or an integer in the range of 1 to 8. In preferred embodiments, only one of $R_9$ or $R_{10}$ can be a carbonyl, e.g., $R_9$, $R_{10}$ and the nitrogen together do not form an imide. In still more preferred embodiments, the term "amine" does not encompass amides, e.g., wherein one of $R_9$ and $R_{10}$ represents a carbonyl. In even more preferred embodiments, $R_9$ and $R_{10}$ (and optionally $R'_{10}$) each independently represent a hydrogen, an alkyl or cycloalkyl, an alkenyl or cycloalkenyl, or alkynyl. Thus, the term "alkylamine" as used herein means an amine group, as defined above, having a substituted (as described above for alkyl) or unsubstituted alkyl attached thereto, i.e., at least one of $R_9$ and $R_{10}$ is an alkyl group.

The term "amide" is art-recognized as an amino-substituted carbonyl and includes a moiety that can be represented by the general formula:

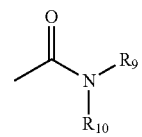

wherein, $R_9$ and $R_{10}$ are as defined above.

"Aryl", as used herein, refers to $C_5$-$C_{10}$-membered aromatic, heterocyclic, fused aromatic, fused heterocyclic, biaromatic, or bihetereocyclic ring systems. Broadly defined, "aryl", as used herein, includes 5-, 6-, 7-, 8-, 9-, and 10-membered single-ring aromatic groups that may include from zero to four heteroatoms, for example, benzene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaromatics". The aromatic ring can be substituted at one or more ring positions with one or more substituents including, but not limited to, halogen, azide, alkyl, aralkyl, alkenyl, alkynyl, cycloalkyl, hydroxyl, alkoxyl, amino (or quaternized amino), nitro, sulthydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —CF$_3$, —CN; and combinations thereof.

The term "aryl" also includes polycyclic ring systems having two or more cyclic rings in which two or more carbons are common to two adjoining rings (i.e., "fused rings") wherein at least one of the rings is aromatic, e.g., the other cyclic ring or rings can be cycloalkyls, cycloalkenyls, cycloalkynyls, aryls and/or heterocycles. Examples of heterocyclic rings include, but are not limited to, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH carbazolyl, carbolinyl, chromanyl, chromenyl, cinnolinyl, decahydroquinolinyl, 2H,6H-1,5,2-dithiazinyl, dihydrofuro[2,3 b]tetrahydrofuran, (uranyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl and xanthenyl. One or more of the rings can be substituted as defined above for "aryl".

The term "aralkyl", as used herein, refers to an alkyl group substituted with an aryl group (e.g., an aromatic or heteroaromatic group).

The term "carbocycle", as used herein, refers to an aromatic or non-aromatic ring in which each atom of the ring is carbon.

"Heterocycle" or "heterocyclic", as used herein, refers to a cyclic radical attached via a ring carbon or nitrogen of a monocyclic or bicyclic ring containing 3-10 ring atoms, and preferably from 5-6 ring atoms, consisting of carbon and one to four heteroatoms each selected from the group consisting of non-peroxide oxygen, sulfur, and N(Y) wherein Y is absent or is H, O, (C$_1$-C$_{10}$) alkyl, phenyl or benzyl, and optionally containing 1-3 double bonds and optionally substituted with one or more substituents. Examples of heterocyclic ring include, but are not limited to, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxepanyl, oxetanyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydropyranyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl and xanthenyl. Heterocyclic groups can optionally be substituted with one or more substituents at one or more positions as defined above for alkyl and aryl, for example, halogen, alkyl, aralkyl, alkenyl, alkynyl, cycloalkyl, hydroxyl, amino, nitro, sulfhydryl, imino, amido, phosphate, phosphonate, phosphinate, carbonyl, carboxyl, silyl, ether, alkylthio, sulfonyl, ketone, aldehyde, ester, a heterocyclyl, an aromatic or heteroaromatic moiety, —CF3, —CN, or the like.

The term "carbonyl" is art-recognized and includes such moieties as can be represented by the general formula:

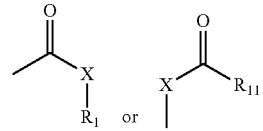

wherein, X is a bond or represents an oxygen or a sulfur, and R$_{11}$ represents a hydrogen, an alkyl, a cycloalkyl, an alkenyl, an cycloalkenyl, or an alkynyl, R'$_{11}$ represents a hydrogen, an alkyl, a cycloalkyl, an alkenyl, an cycloalkenyl, or an alkynyl. Where X is an oxygen and R$_{11}$ or R'$_{11}$ is not hydrogen, the formula represents an "ester". Where X is an oxygen and R$_{11}$ is as defined above, the moiety is referred to herein as a carboxyl group, and particularly when R$_{11}$ is a hydrogen, the formula represents a "carboxylic acid". Where X is an oxygen and is hydrogen, the formula represents a "formate". In general, where the oxygen atom of the above formula is replaced by sulfur, the formula represents a "thiocarbonyl" group. Where X is a sulfur and R$_{11}$ or R'$_{11}$ is not hydrogen; the formula represents a "thioester." Where X is a sulfur and R$_{11}$ is hydrogen, the formula represents a "thiocarboxylic acid." Where X is a sulfur and R'$_{11}$ is hydrogen, the formula represents a "thiofoxmate." On the other hand, where X is a bond, and R$_{11}$ is not hydrogen, the above formula represents a "ketone" group. Where X is a bond, and R$_{11}$ is hydrogen, the above formula represents an "aldehyde" group.

The term "heteroatom" as used herein means an atom of any element other than carbon or hydrogen. Preferred heteroatoms are boron, nitrogen, oxygen, phosphorus, sulfur and selenium. Other heteroatoms include silicon and arsenic.

As used herein, the term "nitro" means —NO$_2$; the term "halogen" designates —F, —Cl, —Br or —I; the term "sullhydryl" means —SH; the term "hydroxyl" means —OH; and the term "sulfonyl" means —SO$_2$—.

"Linker" or "spacer", as used herein, refers to an atom or atoms that separate the 6-membered ring of the curcuminoid from the substituent $R_{11}$. The Linker or spacer can be a single atom, such as a heteroatom (e.g., O or S), a group of atoms, such as a functional group (e.g., amine, —C(=O)—, —CH$_2$—), or multiple groups of atoms, such as an alkylene chain.

The term "substituted" as used herein, refers to all permissible substituents of the compounds described herein. In the broadest sense, the permissible substituents include acyclic and cyclic, branched and unbranched, carbocyclic and heterocyclic, aromatic and nonaromatic substituents of organic compounds. Illustrative substituents include, but are not limited to, halogens, hydroxyl groups, or any other organic groupings containing any number of carbon atoms, preferably 1-14 carbon atoms, and optionally include one or more heteroatoms such as oxygen, sulfur, or nitrogen grouping in linear, branched, or cyclic structural formats. Representative substituents include alkyl, substituted alkyl, alkenyl, substituted alkenyl, alkynyl, substituted alkynyl, phenyl, substituted phenyl, aryl, substituted aryl, heteroaryl, substituted heteroaryl, halo, hydroxyl, alkoxy, substituted alkoxy, phenoxy, substituted phenoxy, aroxy, substituted aroxy, alkylthio, substituted alkylthio, phenylthio, substituted phenylthio, arylthio, substituted arylthio, cyano, isocyano, substituted isocyano, carbonyl, substituted carbonyl, carboxyl, substituted carboxyl, amino, substituted amino, amido, substituted amido, sulfonyl, substituted sulfonyl, sulfonic acid, phosphoryl, substituted phosphoryl, phosphonyl, substituted phosphonyl, polyaryl, substituted polyaryl, $C_3$-$C_{20}$ cyclic, substituted $C_3$-$C_{20}$ cyclic, heterocyclic, substituted heterocyclic, aminoacid, peptide, and polypeptide groups.

Heteroatoms such as nitrogen may have hydrogen substituents and/or any permissible substituents of organic compounds described herein which satisfy the valences of the heteroatoms. It is understood that "substitution" or "substituted" includes the implicit proviso that such substitution is in accordance with permitted valence of the substituted atom and the substituent, and that the substitution results in a stable compound, i.e. a compound that does not spontaneously undergo transformation such as by rearrangement, cyclization, elimination, etc.

II. Compounds

1. Curcuminoids

The compounds described herein are compounds of Formula I:

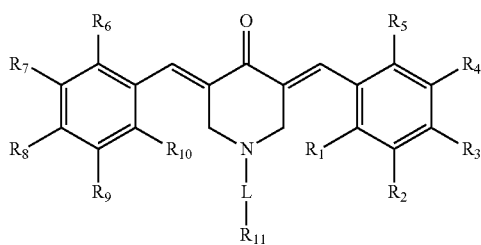

Formula I wherein $R_1$-$R_{10}$ are independently absent or selected from the group consisting of substituted or unsubstituted, linear, branched, or cyclic alkyl, alkenyl, or alkynyl; halogen, substituted or unsubstituted aryl or heteroaryl; substituted or unsubstituted alkoxy; hydroxy, cyano, formyl, acyl, carboxylic acid (—COOH), carboxylate (—COO$^-$), primary amide (e.g., —CONH$_2$), secondary amide (e.g., —CONHR$_{12}$), tertiary amide (e.g., —CONR$_{12}$R$_{12}$), secondary carbamate (e.g., —CONHR$_{12}$; —NHCOOR$_{12}$), tertiary carbamate (e.g., —OCONR$_{12}$R$_{12}$; —NR$_{12}$COOR$_{12}$), urea (e.g., —NHCONHR$_{12}$; —NR$_{12}$CONHR$_{12}$; —NHCONR$_{12}$R$_{12}$, —NR$_{12}$CONR$_{12}$R$_{12}$), carbinol (e.g., —CH$_2$OH; —CHR$_{12}$OH, —CR$_{12}$R$_{12}$OH), ester (e.g., —COOR$_{12}$), thiol (—SH), primary amine (—NH$_2$), secondary amine (e.g., —NHR$_{12}$), tertiary amine (e.g., —NR$_{12}$R$_{12}$), thioether (e.g., —SR$_{12}$), sulfinyl group (e.g., —SOR$_{12}$), sulfonyl group (e.g., —SOOR$_{12}$);

$R_{11}$ is substituted or unsubstituted alkyl, cycloalkyl, alkenyl, cycloalkenyl, or alkynyl; substituted or unsubstituted benzyl sulfonyl (Bnz); substituted or substituted p-toluene sulfonyl (p-Ts); substituted or unsubstituted benzyl; substituted or unsubstituted aryl; substituted or unsubstituted heteroaryl; wherein the $R_{11}$ if substituted, can be substituted with one or more of alkyl, cycloalkyl, alkenyl, cycloalkenyl, alkoxy, amine, halogen, hydroxyl, nitrile, CF$_3$, ester, amide, urea, carbamate, thioether, carboxylic acid, and aryl; and L is absent or a linker or spacer.

In some embodiments, $R_{11}$ is unsubstituted alkyl, such as methyl, ethyl, or propyl. In some embodiments, $R_{11}$ is unsubstituted ethyl. In some embodiments, $R_{11}$ is unsubstituted ethyl and at least one of $R_1$-$R_5$ and at least one of $R_6$-$R_{10}$ are halogen (e.g., Br, Cl, or F). In particular embodiments, $R_{11}$ and $R_8$ are halogen and $R_1$, $R_2$, $R_4$-$R_7$, $R_9$, and $R_{10}$ are hydrogen. In more particular embodiments, $R_3$ and $R_8$ are the same halogen. In still other embodiments, $R_{11}$ is unsubstituted ethyl and at least one of $R_1$-$R_5$ and at least one of $R_6$-$R_{10}$ are unsubstituted alkyl, such as methyl, ethyl, n-propyl, isopropyl, n-butyl, or t-butyl. In particular embodiments, $R_3$ and $R_8$ are unsubstituted alkyl and $R_1$, $R_2$, $R_4$-$R_7$, $R_9$, and $R_{10}$ are hydrogen. In more particular embodiments, $R_3$ and $R_8$ are the same unsubstituted alkyl. In still other embodiments, $R_{11}$ is unsubstituted ethyl and at least one of $R_1$-$R_5$ and at least one of $R_6$-$R_{10}$ are unsubstituted alkoxy, such as methoxy. In particular embodiments, $R_3$ and $R_8$ are unsubstituted alkoxy and $R_1$, $R_2$, $R_4$-$R_7$, $R_9$, and $R_{10}$ are hydrogen. In more particular embodiments, $R_3$ and $R_8$ are the same unsubstituted alkoxy.

In other embodiments, $R_{11}$ is unsubstituted p-toluene sulfonyl. In some embodiments, $R_{11}$ is unsubstituted p-toluene sulfonyl and at least one of $R_1$-$R_5$ and at least one of $R_6$-$R_{10}$ are halogen (e.g., Br, Cl, or F). In particular embodiments, $R_3$ and $R_8$ are halogen and $R_1$, $R_2$, $R_4$-$R_7$, $R_9$, and $R_{10}$ are hydrogen. In more particular embodiments, $R_3$ and $R_8$ are the same halogen. In still other embodiments, $R_{11}$ is unsubstituted p-toluene sulfonyl and at least one of $R_1$-$R_5$ and at least one of $R_6$-$R_{10}$ are unsubstituted alkyl, such as methyl, ethyl, n-propyl, isopropyl, n-butyl, or t-butyl. In particular embodiments, $R_3$ and $R_8$ are unsubstituted alkyl and $R_1$, $R_2$, $R_4$-$R_7$, $R_9$, and $R_{10}$ are hydrogen. In more particular embodiments, $R_3$ and $R_8$ are the same unsubstituted alkyl. In still other embodiments, $R_{11}$ is unsubstituted p-toluene sulfonyl and at least one of $R_1$-$R_5$ and at least one of $R_6$-$R_{10}$ are unsubstituted alkoxy, such as methoxy. In particular embodiments, $R_3$ and $R_8$ are unsubstituted alkoxy and $R_1$, $R_2$, $R_4$-$R_7$, $R_9$, and $R_{10}$ are hydrogen. In more particular embodiments, $R_3$ and $R_8$ are the same unsubstituted alkoxy.

In other embodiments, $R_{11}$ is unsubstituted benzyl. In some embodiments, $R_{11}$ is unsubstituted benzyl and at least one of $R_1$-$R_5$ and at least one of $R_6$-$R_{10}$ are halogen (e.g., Br, Cl, or F). In particular embodiments, $R_3$ and $R_8$ are halogen and $R_1$, $R_2$, $R_4$-$R_7$, $R_9$, and $R_{10}$ are hydrogen. In more particular embodiments, $R_3$ and $R_8$ are the same halogen. In still other embodiments, $R_{11}$ is unsubstituted benzyl and at least one of $R_1$-$R_5$ and at least one of $R_6$-$R_{10}$ are unsubstituted alkyl, such as methyl, ethyl, n-propyl, isopropyl, n-butyl, or t-butyl. In particular embodiments, $R_3$ and $R_8$ are unsubstituted alkyl and $R_1$, $R_2$, $R_4$-$R_7$, $R_9$, and $R_{10}$ are hydrogen. In more particular embodiments, $R_3$ and $R_8$ are the same unsubstituted alkyl. In still other embodiments, $R_{11}$ is unsubstituted benzyl and at least one of $R_1$-$R_5$ and at least one of $R_6$-$R_{10}$ are unsubstituted alkoxy, such as methoxy. In particular embodiments, $R_3$ and $R_8$ are unsubstituted alkoxy and $R_1$, $R_2$, $R_4$-$R_7$, $R_9$, and $R_{10}$ are hydrogen. In more particular embodiments, $R_3$ and $R_8$ are the same unsubstituted alkoxy.

In other embodiments, $R_{11}$ is unsubstituted benzyl sulfonyl. In some embodiments, $R_{11}$ is unsubstituted benzyl sulfonyl, at least one of $R_1$-$R_5$ and at least one of $R_6$-$R_{10}$ are halogen (e.g., Br, Cl, or F). In particular embodiments, $R_3$ and $R_8$ are halogen and $R_1$, $R_2$, $R_4$-$R_7$, $R_9$, and $R_{10}$ are hydrogen. In more particular embodiments, $R_3$ and $R_8$ are the same halogen. In still other embodiments, $R_{11}$ is unsubstituted benzyl sulfonyl and at least one of $R_1$-$R_5$ and at least one of $R_6$-$R_{10}$ are unsubstituted alkyl, such as methyl, ethyl, n-propyl, isopropyl, n-butyl, or t-butyl. In particular embodiments, $R_3$ and $R_8$ are unsubstituted alkyl and $R_1$, $R_2$, $R_4$-$R_7$, $R_9$, and $R_{10}$ are hydrogen. In more particular embodiments, $R_3$ and $R_8$ are the same unsubstituted alkyl. In still other embodiments, $R_{11}$ is unsubstituted benzyl sulfonyl and at least one of $R_1$-$R_5$ and at least one of $R_6$-$R_{10}$ are unsubstituted alkoxy, such as methoxy. In particular embodiments, $R_3$ and $R_8$ are unsubstituted alkoxy and $R_1$, $R_2$, $R_4$-$R_7$, $R_9$, and $R_{10}$ are hydrogen. In more particular embodiments, $R_3$ and $R_8$ are the same unsubstituted alkoxy.

In some embodiments, $R_1$-$R_{11}$ are as defined above and L is absent. In other embodiments, L is a one-carbon spacer and $R_1$-$R_{11}$ are as defined above.

In still other embodiments, L is present and $R_{11}$ is a substituted or unsubstituted aryl or heteroaryl group. In particular embodiments, L is a substituted or unsubstituted alkylene group, such as a methylene group, and $R_{11}$ is a substituted or unsubstituted triazole. In some embodiments, L is an alkylene groups, such as substituted or unsubstituted methylene linker and $R_{11}$ is a triazole group, such as

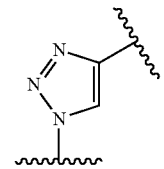

wherein L is attached to the triazole group at the C5 position. In some embodiments, the triazole ring is substituted at the nitrogen as shown above. In particular embodiments, the triazole ring is substituted with a substituted alkyl group. In more particular embodiments, the alkyl group is substituted as shown below:

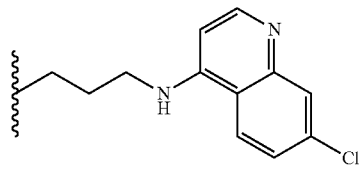 [SMILES: *CCCNc1ccnc2cc(Cl)ccc12]

Compounds which were synthesized and evaluated for cytotoxicity are shown in Table 1.

TABLE 1

| Code | Structure | Molecular Formula | Mol. Wt. |
|---|---|---|---|
| 3a | 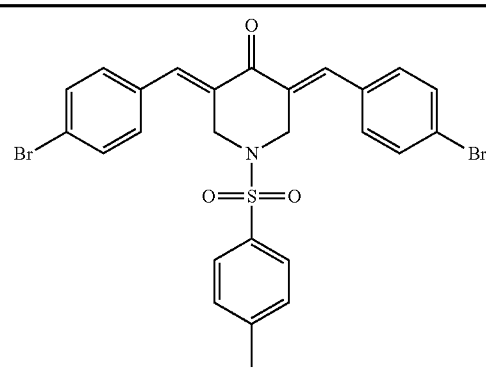 | $C_{26}H_{21}Br_2NO_3S$ | 587.32 |
| 3b | 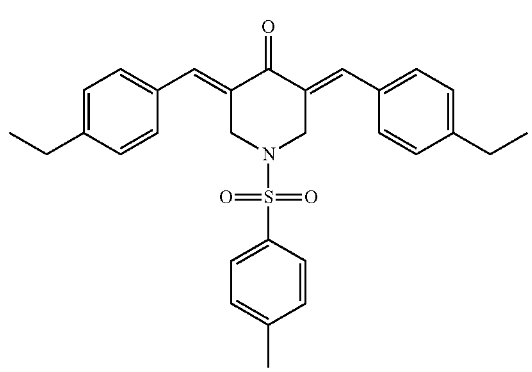 [SMILES: CCc1ccc(/C=C2\CN(S(=O)(=O)c3ccc(C)cc3)C/C(=C\c3ccc(CC)cc3)C2=O)cc1] | $C_{30}H_{31}NO_3S$ | 485.63 |

TABLE 1-continued

Synthesized compounds

| Code | Structure | Molecular Formula | Mol. Wt. |
|---|---|---|---|
| 3c | 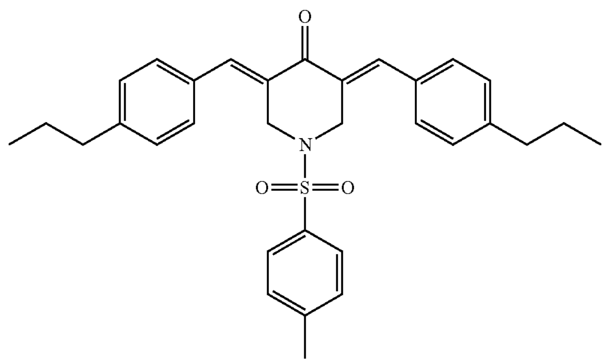 [SMILES: CCCc1ccc(/C=C2\CN(S(=O)(=O)c3ccc(C)cc3)C/C(=C\c3ccc(CCC)cc3)C2=O)cc1] | $C_{32}H_{35}NO_3S$ | 513.69 |
| 3d | 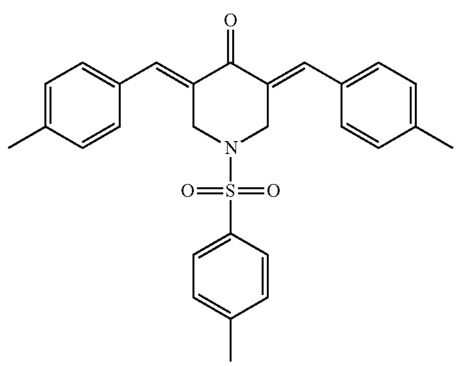 | $C_{28}H_{27}NO_3S$ | 457.58 |
| 3e | 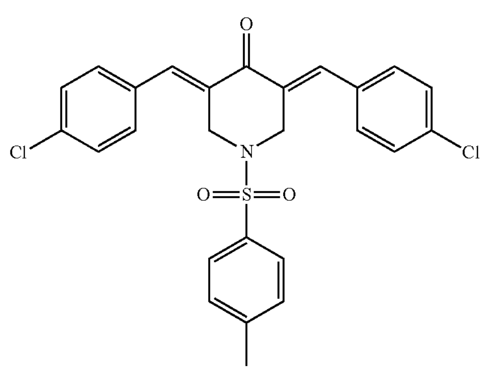 [SMILES: Cc1ccc(S(=O)(=O)N2C/C(=C\c3ccc(Cl)cc3)C(=O)/C(=C/c3ccc(Cl)cc3)C2)cc1] | $C_{26}H_{21}Cl_2NO_3S$ | 498.42 |
| 3f | 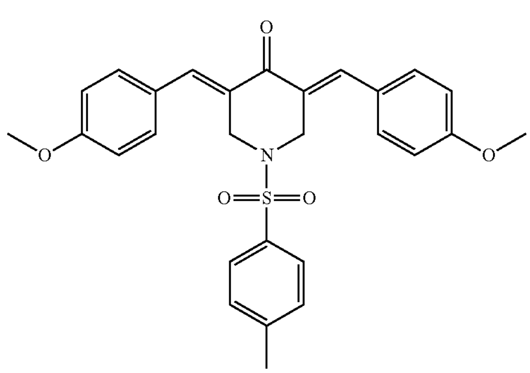 | $C_{28}H_{27}NO_5S$ | 489.58 |

TABLE 1-continued

Synthesized compounds

| Code | Structure | Molecular Formula | Mol. Wt. |
|---|---|---|---|
| 3g | 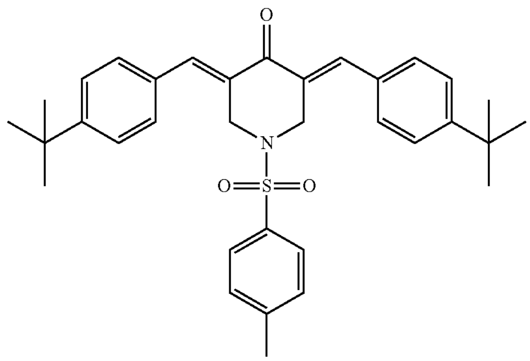 [SMILES: Cc1ccc(S(=O)(=O)N2C/C(=C\c3ccc(C(C)(C)C)cc3)C(=O)/C(=C/c3ccc(C(C)(C)C)cc3)C2)cc1] | $C_{34}H_{39}NO_3S$ | 541.74 |
| 3h | 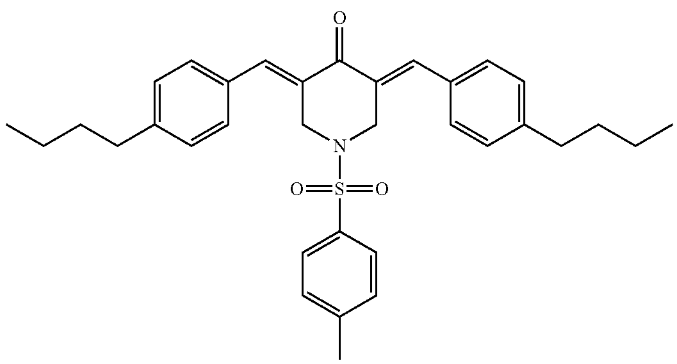 [SMILES: CCCCc1ccc(/C=C2\CN(S(=O)(=O)c3ccc(C)cc3)C/C(=C\c3ccc(CCCC)cc3)C2=O)cc1] | $C_{34}H_{39}NO_3S$ | 541.74 |
| 3i | 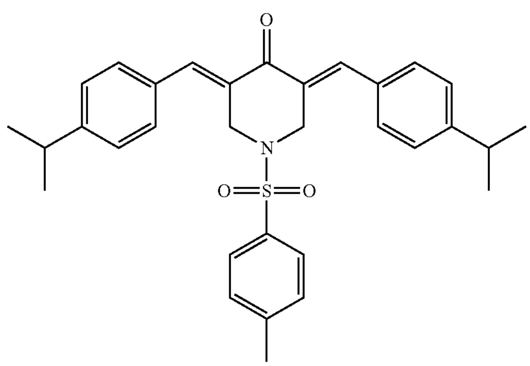 [SMILES: Cc1ccc(S(=O)(=O)N2C/C(=C\c3ccc(C(C)C)cc3)C(=O)/C(=C/c3ccc(C(C)C)cc3)C2)cc1] | $C_{32}H_{35}NO_3S$ | 513.69 |
| 3j | 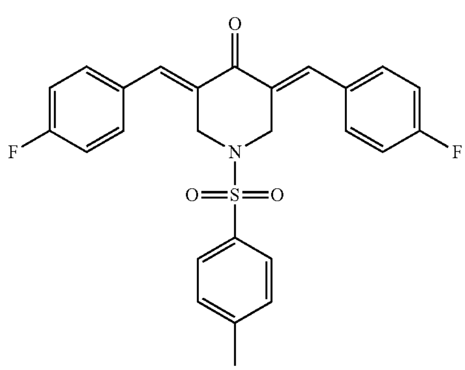 [SMILES: Cc1ccc(S(=O)(=O)N2C/C(=C\c3ccc(F)cc3)C(=O)/C(=C/c3ccc(F)cc3)C2)cc1] | $C_{26}H_{21}F_2NO_3S$ | 465.51 |

TABLE 1-continued

Synthesized compounds

| Code | Structure | Molecular Formula | Mol. Wt. |
|------|-----------|-------------------|----------|
| 4a   | 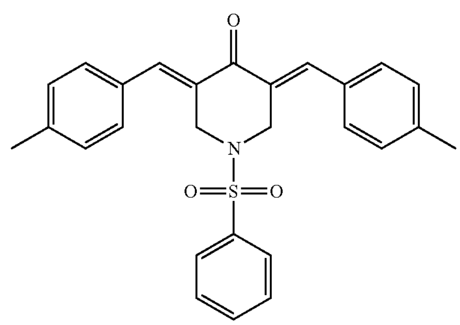          | $C_{27}H_{25}NO_3S$ | 443.55 |
| 4b   | 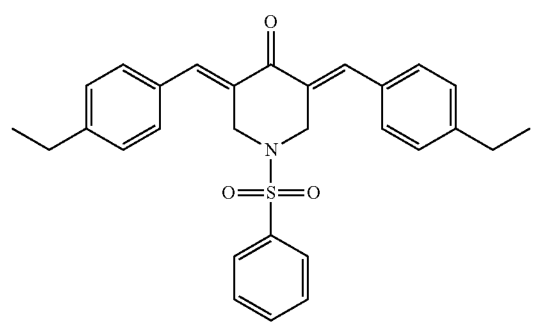 [SMILES: CCc1ccc(/C=C2\CN(S(=O)(=O)c3ccccc3)C/C(=C\c3ccc(CC)cc3)C2=O)cc1]          | $C_{29}H_{29}NO_3S$ | 471.61 |
| 4c   | 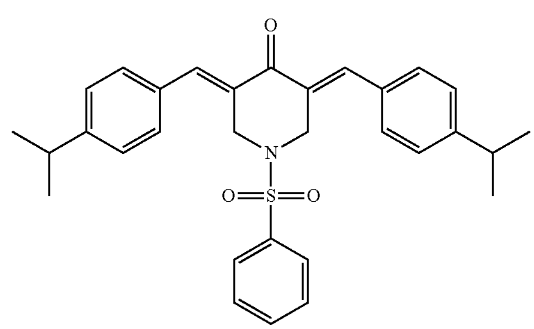 [SMILES: CC(C)c1ccc(/C=C2\CN(S(=O)(=O)c3ccccc3)C/C(=C\c3ccc(C(C)C)cc3)C2=O)cc1]          | $C_{31}H_{33}NO_3S$ | 499.66 |
| 4d   | 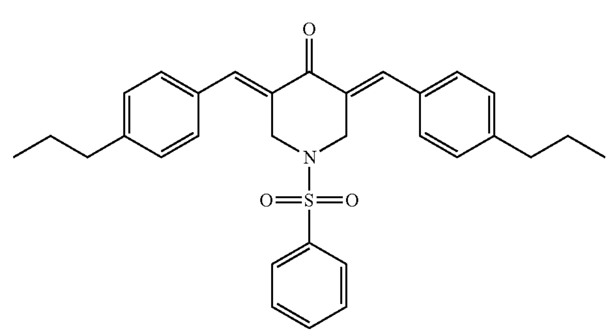 [SMILES: CCCc1ccc(/C=C2\CN(S(=O)(=O)c3ccccc3)C/C(=C\c3ccc(CCC)cc3)C2=O)cc1]          | $C_{31}H_{33}NO_3S$ | 499.66 |

TABLE 1-continued
Synthesized compounds
| Code | Structure | Molecular Formula | Mol. Wt. |
|---|---|---|---|
| 4e | 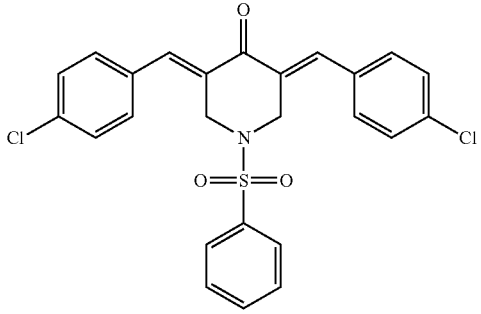 [SMILES: O=C1/C(=C/c2ccc(Cl)cc2)CN(S(=O)(=O)c2ccccc2)C/C1=C\c1ccc(Cl)cc1] | $C_{25}H_{19}Cl_2NO_3S$ | 484.39 |
| 4f | 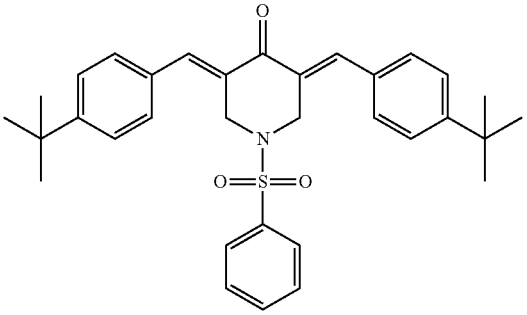 [SMILES: CC(C)(C)c1ccc(/C=C2\CN(S(=O)(=O)c3ccccc3)C/C(=C\c3ccc(C(C)(C)C)cc3)C2=O)cc1] | $C_{33}H_{37}NO_3S$ | 527.71 |
| 4g | 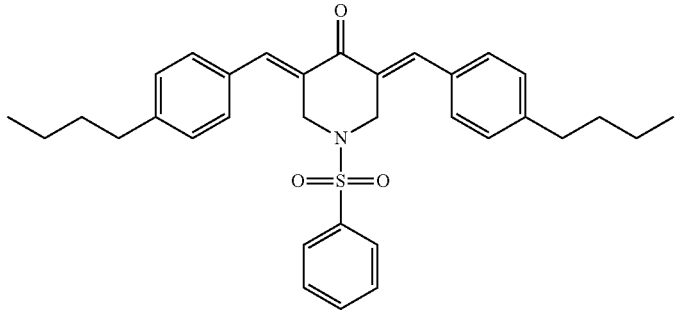 [SMILES: CCCCc1ccc(/C=C2\CN(S(=O)(=O)c3ccccc3)C/C(=C\c3ccc(CCCC)cc3)C2=O)cc1] | $C_{33}H_{37}NO_3S$ | 527.71 |
| 4h | 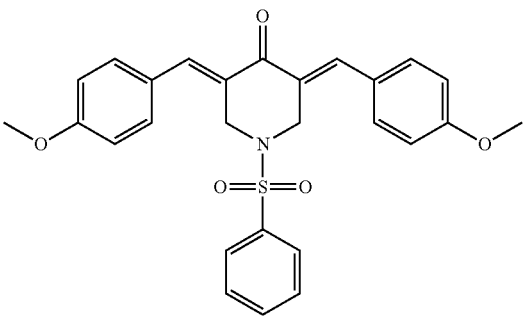 | $C_{27}H_{25}NO_5S$ | 475.55 |

TABLE 1-continued

Synthesized compounds

| Code | Structure | Molecular Formula | Mol. Wt. |
|------|-----------|-------------------|----------|
| 4i   | 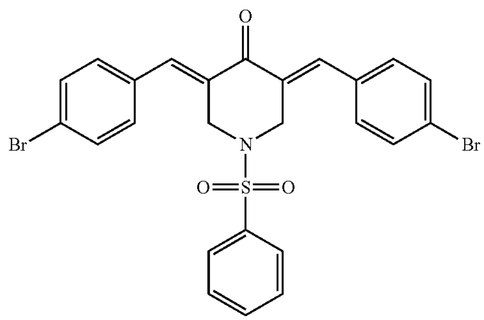 [SMILES: O=C1/C(=C/c2ccc(Br)cc2)CN(S(=O)(=O)c2ccccc2)C/C1=C\c1ccc(Br)cc1]          | $C_{25}H_{19}Br_2NO_3S$ | 573.29 |
| 4j   | 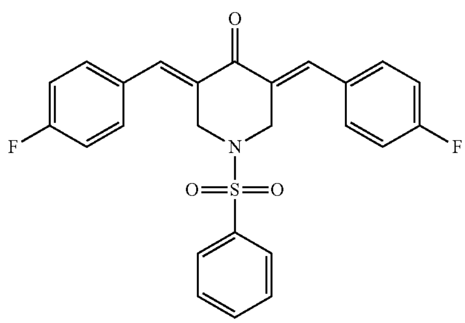 [SMILES: O=C1/C(=C/c2ccc(F)cc2)CN(S(=O)(=O)c2ccccc2)C/C1=C\c1ccc(F)cc1]          | $C_{25}H_{19}F_2NO_3S$  | 451.48 |
| 5a   | 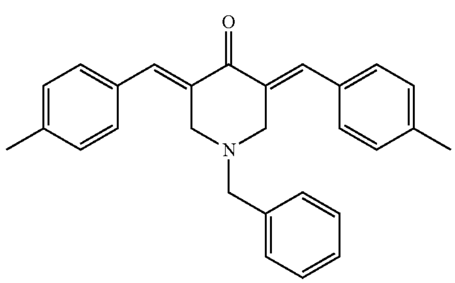          | $C_{28}H_{27}NO$        | 393.52 |
| 5b   | 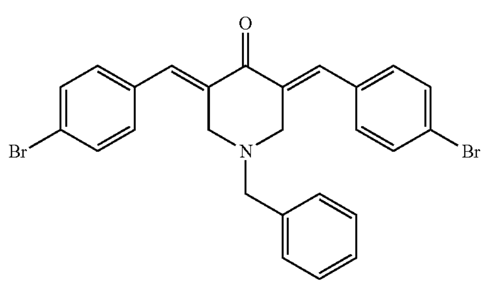 [SMILES: O=C1/C(=C/c2ccc(Br)cc2)CN(Cc2ccccc2)C/C1=C\c1ccc(Br)cc1]          | $C_{26}H_{21}Br_2NO$    | 523.25 |
| 5c   | 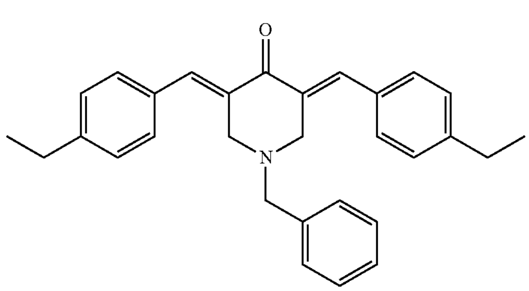 [SMILES: CCc1ccc(/C=C2\CN(Cc3ccccc3)C/C(=C\c3ccc(CC)cc3)C2=O)cc1]          | $C_{30}H_{31}NO$        | 421.57 |

TABLE 1-continued

Synthesized compounds

| Code | Structure | Molecular Formula | Mol. Wt. |
|---|---|---|---|
| 5d | 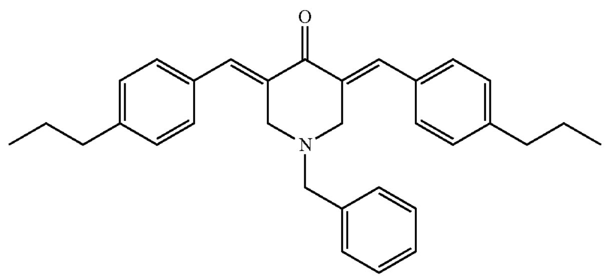 [SMILES: CCCc1ccc(/C=C2\CN(Cc3ccccc3)C/C(=C\c3ccc(CCC)cc3)C2=O)cc1] | $C_{32}H_{35}NO$ | 449.62 |
| 5e | 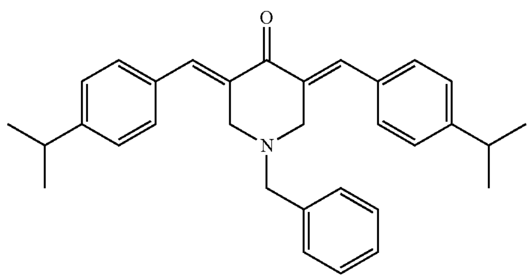 [SMILES: CC(C)c1ccc(/C=C2\CN(Cc3ccccc3)C/C(=C\c3ccc(C(C)C)cc3)C2=O)cc1] | $C_{32}H_{35}NO$ | 449.62 |
| 5f | 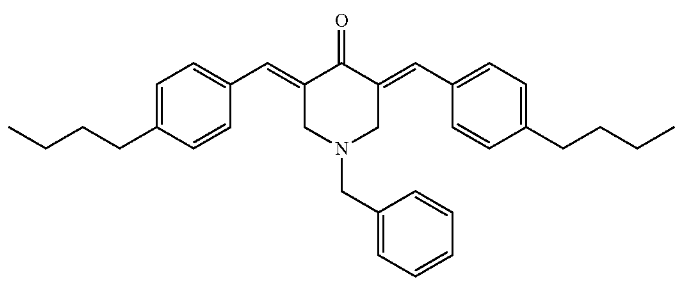 [SMILES: CCCCc1ccc(/C=C2\CN(Cc3ccccc3)C/C(=C\c3ccc(CCCC)cc3)C2=O)cc1] | $C_{34}H_{39}NO$ | 477.67 |
| 5g | 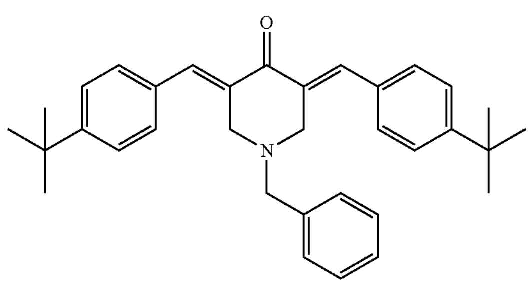 [SMILES: CC(C)(C)c1ccc(/C=C2\CN(Cc3ccccc3)C/C(=C\c3ccc(C(C)(C)C)cc3)C2=O)cc1] | $C_{34}H_{39}NO$ | 477.67 |
| 5h | 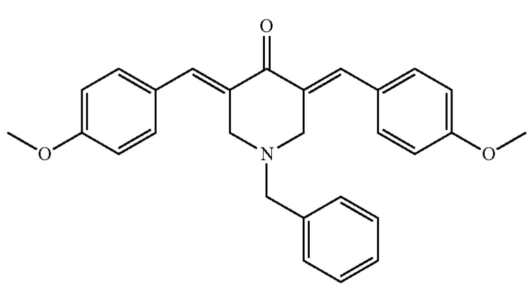 | $C_{28}H_{27}NO_3$ | 425.51 |

TABLE 1-continued

Synthesized compounds

| Code | Structure | Molecular Formula | Mol. Wt. |
|---|---|---|---|
| 5i | 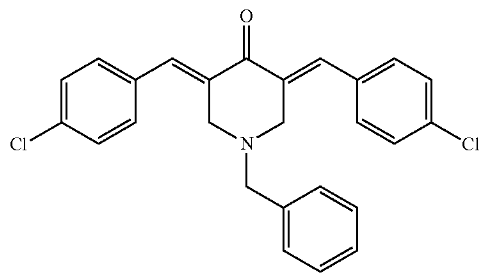 [SMILES: O=C1/C(=C/c2ccc(Cl)cc2)CN(Cc2ccccc2)C/C1=C\c1ccc(Cl)cc1] | $C_{26}H_{21}Cl_2NO$ | 343.35 |
| 5j | 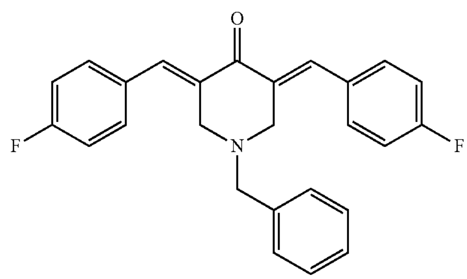 [SMILES: O=C1/C(=C/c2ccc(F)cc2)CN(Cc2ccccc2)C/C1=C\c1ccc(F)cc1] | $C_{26}H_{21}F_2NO$ | 401.44 |
| 6a | 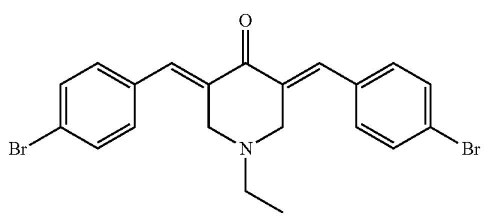 [SMILES: CCN1C/C(=C\c2ccc(Br)cc2)C(=O)/C(=C/c2ccc(Br)cc2)C1] | $C_{21}H_{19}Br_2NO$ | 461.18 |
| 6b | 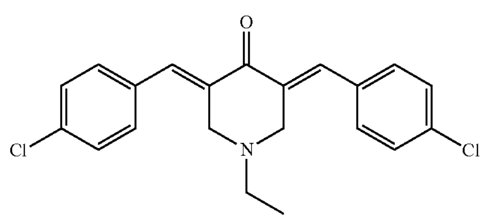 [SMILES: CCN1C/C(=C\c2ccc(Cl)cc2)C(=O)/C(=C/c2ccc(Cl)cc2)C1] | $C_{21}H_{19}Cl_2NO$ | 372.28 |
| 6c | 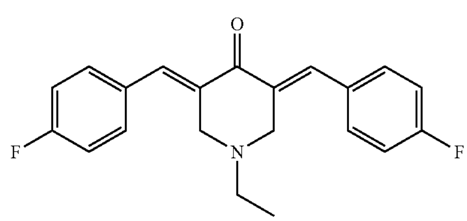 [SMILES: CCN1C/C(=C\c2ccc(F)cc2)C(=O)/C(=C/c2ccc(F)cc2)C1] | $C_{21}H_{19}F_2NO$ | 339.37 |
| 6d | 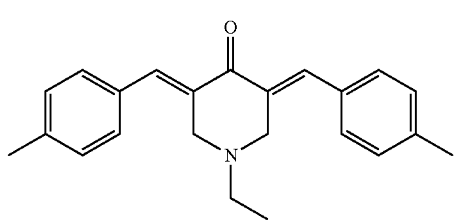 | $C_{23}H_{25}NO$ | 331.45 |

TABLE 1-continued

Synthesized compounds

| Code | Structure | Molecular Formula | Mol. Wt. |
|---|---|---|---|
| 6e | 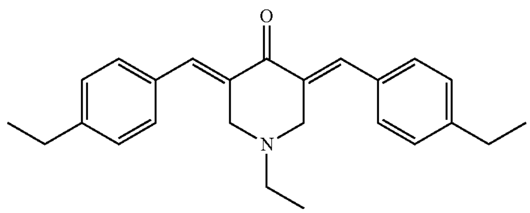 [SMILES: CCc1ccc(/C=C2\CN(CC)C/C(=C\c3ccc(CC)cc3)C2=O)cc1] | $C_{25}H_{29}NO$ | 359.5 |
| 6f | 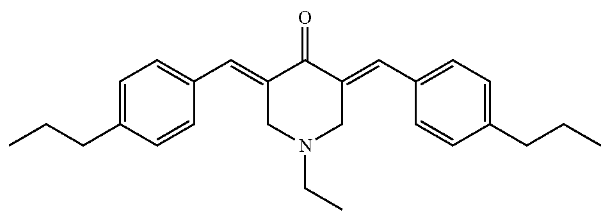 [SMILES: CCCc1ccc(/C=C2\CN(CC)C/C(=C\c3ccc(CCC)cc3)C2=O)cc1] | $C_{27}H_{33}NO$ | 387.55 |
| 6g | 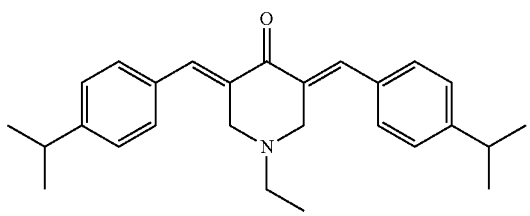 [SMILES: CCN1C/C(=C\c2ccc(C(C)C)cc2)C(=O)/C(=C/c2ccc(C(C)C)cc2)C1] | $C_{27}H_{33}NO$ | 387.55 |
| 6h | 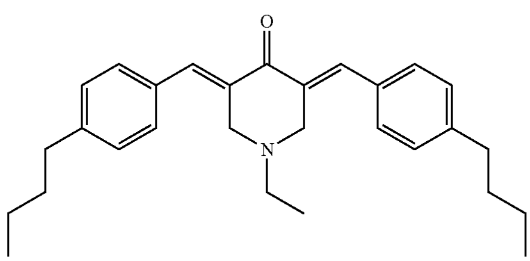 [SMILES: CCCCc1ccc(/C=C2\CN(CC)C/C(=C\c3ccc(CCCC)cc3)C2=O)cc1] | $C_{29}H_{37}NO$ | 415.61 |
| 6i | 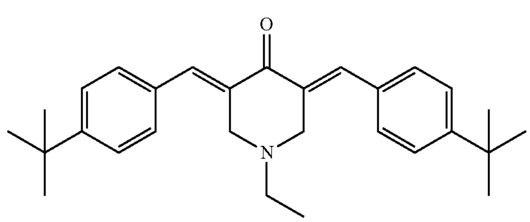 [SMILES: CCN1C/C(=C\c2ccc(C(C)(C)C)cc2)C(=O)/C(=C/c2ccc(C(C)(C)C)cc2)C1] | $C_{29}H_{37}NO$ | 415.61 |
| 6j | 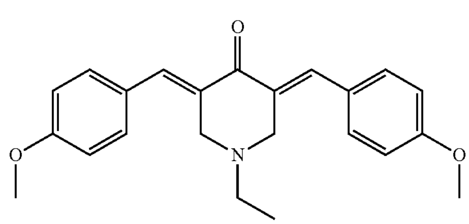 [SMILES: CCN1C/C(=C\c2ccc(OC)cc2)C(=O)/C(=C/c2ccc(OC)cc2)C1] | $C_{23}H_{25}NO_3$ | 363.44 |

In other embodiments, L is an alkylene groups, such as substituted or unsubstituted methylene linker and $R_{11}$ is a triazole group, such as

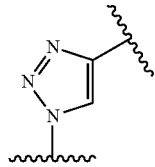

wherein L is attached to the triazole group at the C5 position. In some embodiments, the triazole ring is substituted at the nitrogen as shown above. In particular embodiments, the triazole ring is substituted with a substituted alkyl group. In more particular embodiments, the alkyl group is substituted as shown below:

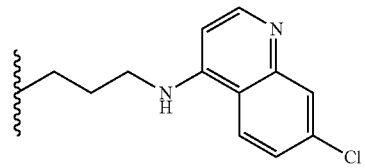 [SMILES: *CCCNc1ccnc2cc(Cl)ccc12]

Examples of these compounds which were synthesized and evaluated for cytotoxicity are shown below in Table 2:

TABLE 2

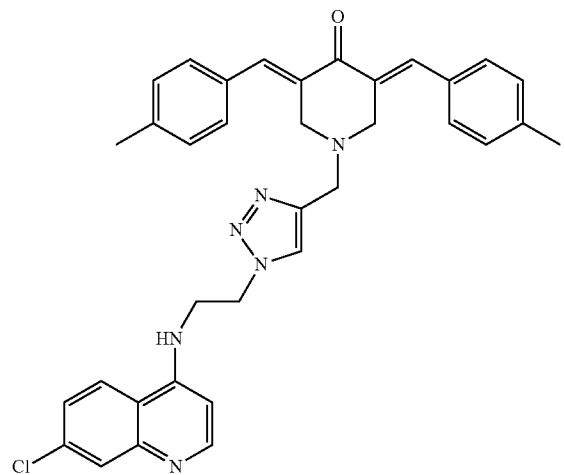 [SMILES: Cc1ccc(/C=C2\CN(Cc3cn(CCNc4ccnc5cc(Cl)ccc45)nn3)C/C(=C\c3ccc(C)cc3)C2=O)cc1]

SR-11

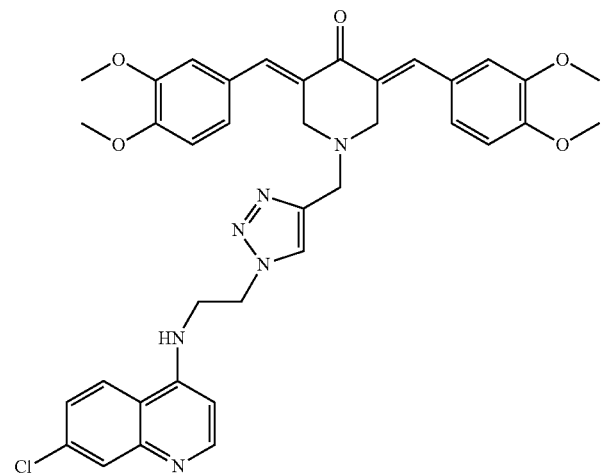 [SMILES: COc1ccc(/C=C2\CN(Cc3cn(CCNc4ccnc5cc(Cl)ccc45)nn3)C/C(=C\c3ccc(OC)c(OC)c3)C2=O)cc1OC]

SR-12

TABLE 2-continued
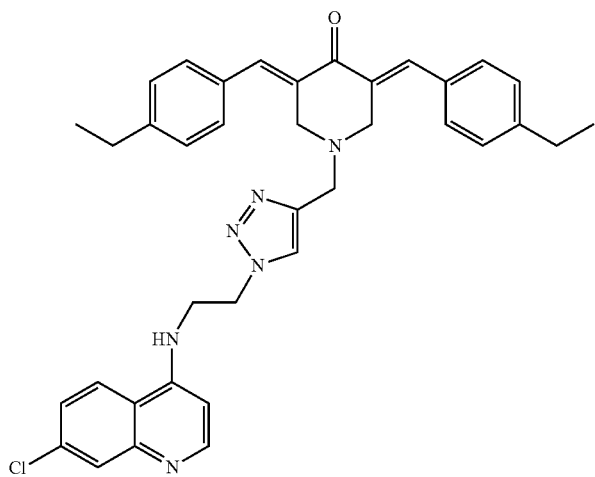 [SMILES: CCc1ccc(/C=C2\CN(Cc3cn(CCNc4ccnc5cc(Cl)ccc45)nn3)C/C(=C\c3ccc(CC)cc3)C2=O)cc1]
SR-13
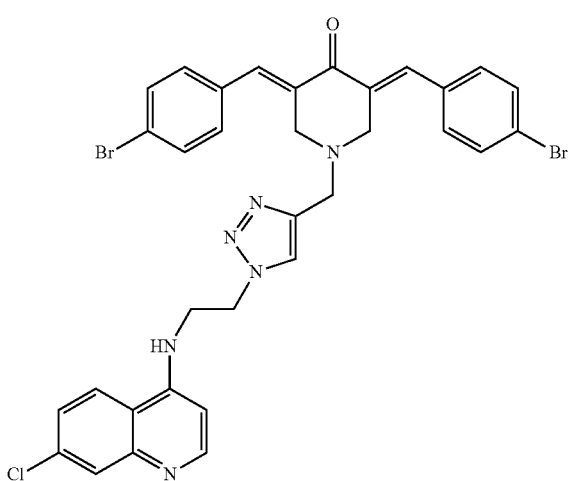
SR-14
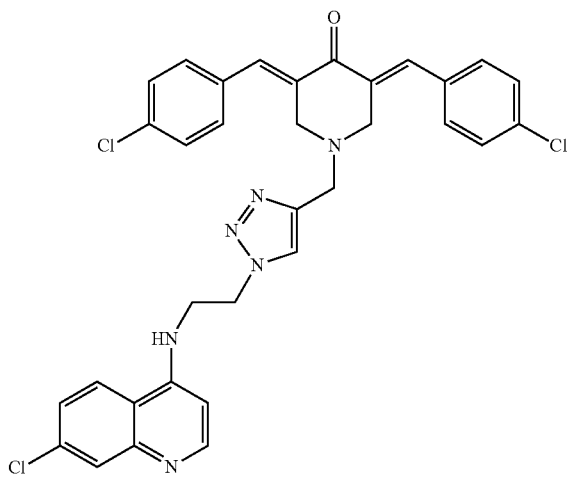 [SMILES: O=C1/C(=C/c2ccc(Br)cc2)CN(Cc2cn(CCNc3ccnc4cc(Cl)ccc34)nn2)C/C1=C\c1ccc(Br)cc1]
SR-15

TABLE 2-continued
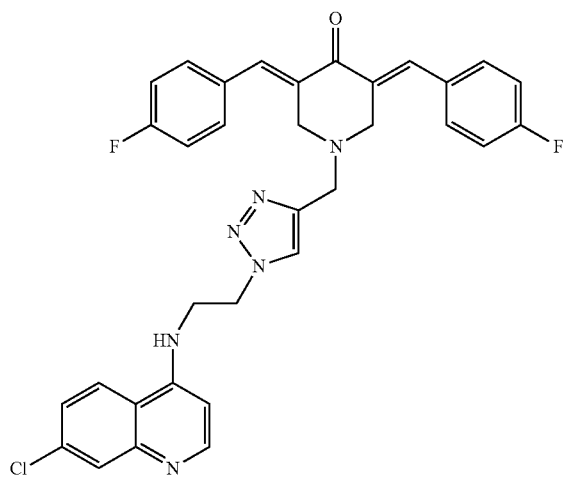 [SMILES: O=C1/C(=C/c2ccc(F)cc2)CN(Cc2cn(CCNc3ccnc4cc(Cl)ccc34)nn2)C/C1=C\c1ccc(F)cc1]
SR-16
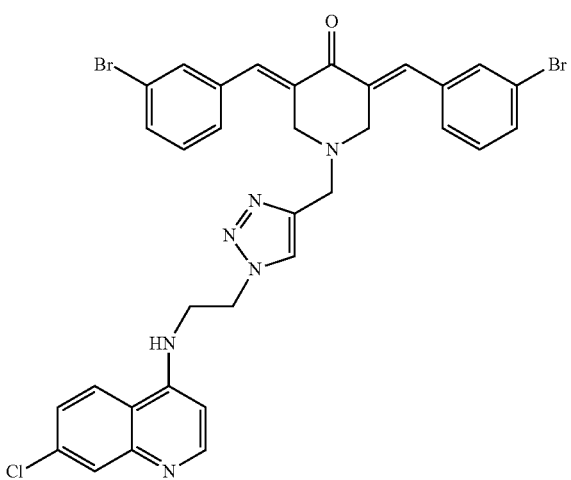 [SMILES: O=C1/C(=C/c2cccc(Br)c2)CN(Cc2cn(CCNc3ccnc4cc(Cl)ccc34)nn2)C/C1=C\c1cccc(Br)c1]
SR-17
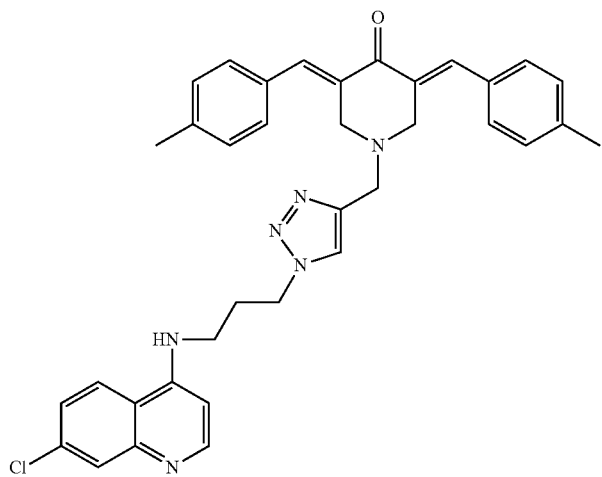 [SMILES: Cc1ccc(/C=C2\CN(Cc3cn(CCCNc4ccnc5cc(Cl)ccc45)nn3)C/C(=C\c3ccc(C)cc3)C2=O)cc1]
SR-34

TABLE 2-continued
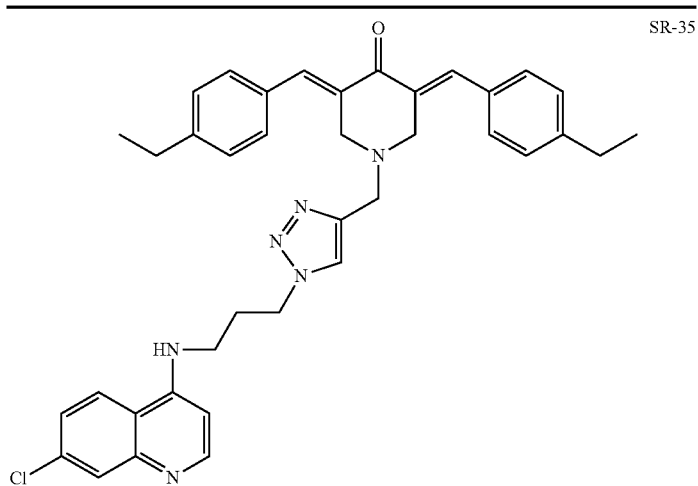
SR-35
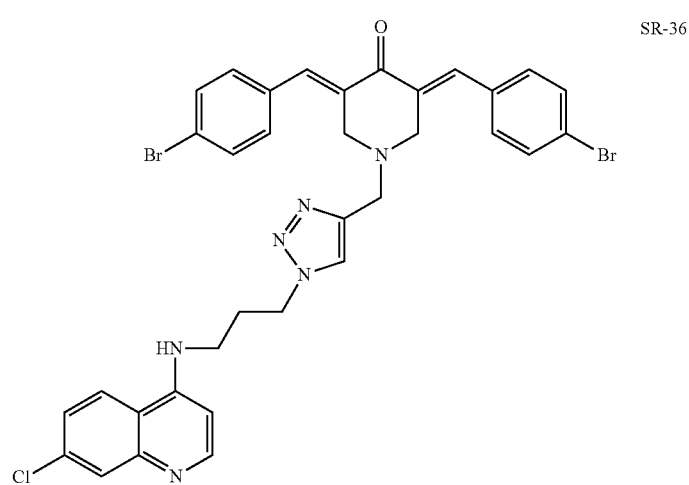
SR-36
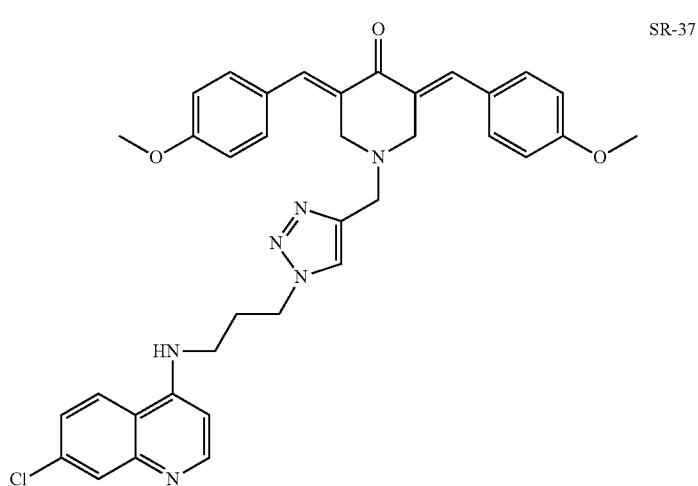
SR-37

TABLE 2-continued
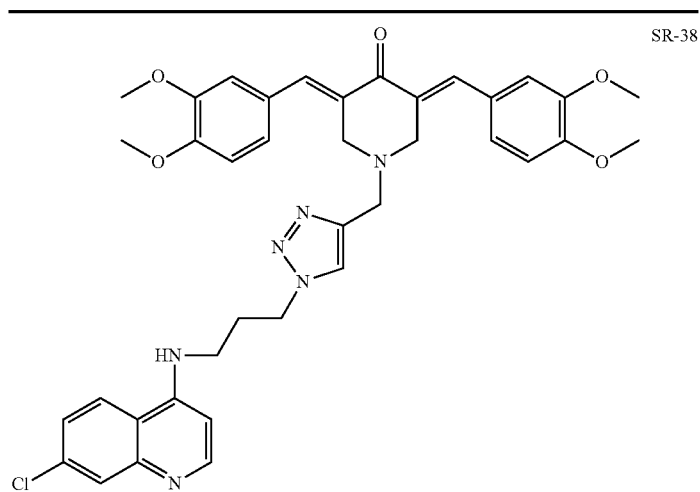
SR-38
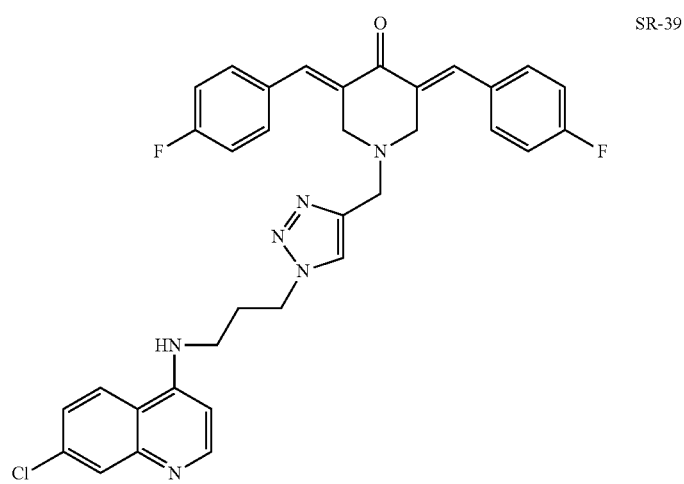
SR-39
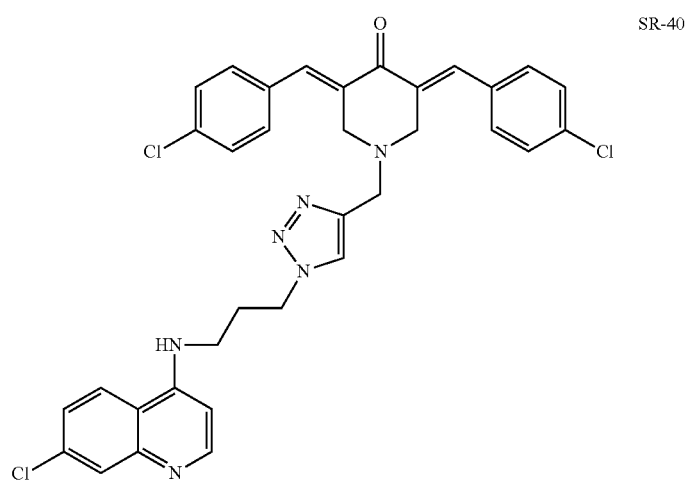
SR-40

C5-curcuminoid-triazole conjugates (SR11-SR17, SR34-SR40) were also evaluated against HeLa cells. As shown in the examples, most of these compounds showed good activity against four cell lines (HeLa, PC3, DU145 and KB).

In other embodiments, the compound has the formula:

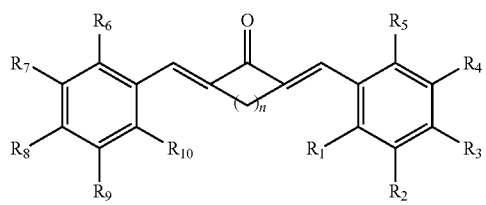

wherein $R_1$-$R_{10}$ are independently absent or selected from the group consisting of substituted or unsubstituted, linear, branched, or cyclic alkyl, alkenyl, or alkynyl; halogen, substituted or unsubstituted aryl or heteroaryl, substituted or unsubstituted alkoxy; hydroxy, cyano, formyl, acyl, carboxylic acid (—COOH), carboxylate (—COO$^-$), primary amide (e.g., —CONH$_2$), secondary amide (e.g., —CONHR$_{12}$), tertiary amide (e.g., —CONR$_{12}$R$_{12}$), secondary carbamate (e.g., —OCONHR$_{12}$; —NHCOOR$_{12}$), tertiary carbamate (e.g., —OCONR$_{12}$R$_{12}$; —NR$_{12}$COOR$_{12}$), urea (e.g., —NHCONHR$_{12}$; —NR$_{12}$CONHR$_{12}$; —NHCONR$_{12}$R$_{12}$, —NR$_{12}$CONR$_{12}$R$_{12}$), carbinol (e.g., —CH$_2$OH; —CHR$_{12}$OH, —CR$_{12}$R$_{12}$OH), ester (e.g., —COOR$_{12}$), thiol (—SH), primary amine (—NH$_2$), secondary amine (e.g., —NHR$_{12}$), tertiary amine (e.g., —NR$_{12}$R$_{12}$), thioether (e.g., —SR$_{12}$), sulfinyl group (e.g., —SOR$_{12}$), and sulfonyl group (e.g., —SOOR$_{12}$), provided that R$_3$ and R$_8$ are substituted alkoxy, such as —O(CH$_2$)$_m$X, where X is halogen or an aromatic or non-aromatic heterocyclic ring, such as

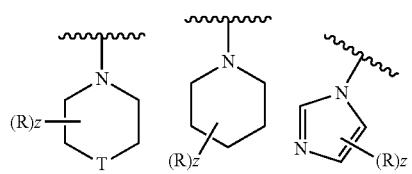

wherein
T is O, S, or NR$_{11}$, wherein each occurrence of R and R$_{11}$ is defined as above form R$_1$-R$_{10}$;
n 0, 2, 3, or 4;
m is an integer from 0-10; and
z, as valence permits, is an integer from 0-10.

In particular embodiments, n is 2 or 3; R$_1$ is —O(CH$_2$)$_3$X, wherein X is halogen or a heterocyclic ring as described above.

In other embodiments, n is 2 or 3; R$_1$ is —O(CH$_2$)$_3$X, wherein X is halogen or a heterocyclic ring as described above; and R$_2$ and R$_9$ are other than hydrogen. In particular embodiments, R$_2$ and R$_9$ are lower alkoxy, such as methoxy.

Exemplary compounds include the following, which were tested in MOLT4 and Hela cell.

TABLE 3

| Structure | IC$_{50}$ (μM) against Hela cell | IC$_{50}$ (μM) against Molt4 cell |
|---|---|---|
| SM216 | No activity below 2.5 μM | >50 |
| SM218 | No activity below 2.5 μM | No activity below 2.5 μM |

TABLE 3-continued

| Structure | IC$_{50}$ (μM) against Hela cell | IC$_{50}$ (μM) against Molt4 cell |
|---|---|---|
| SM223 | No activity below 2.5 μM | No activity below 2.5 μM |
| SM226 | 0.02 | 0.4 |
| SM229 | 0.03 | 0.5 |
| SM232 | 0.1 | 0.9 |

2. Curcumin Analogue Conjugates

The compounds described herein may be linked to another molecule or molecules in order to improve the efficacy of the compounds. Suitable molecules include, but are not limited to, targeting agents and agents, which increase the in vivo half-life of the compounds (e.g., polyethylene glycol). The compounds can be linked to such molecules in any manner provided that each region of the conjugate continues to perform its intended function without significant impairment of biological activity, for example, the anti-tumor activity and/or anti-inflammatory activity of the compounds disclosed herein.

The compounds described herein may be directly linked to a second compound or may be linked via a linker. The term "linker", as used herein, refers to one or more polyfunctional, e.g., bifunctional molecules, which can be used to covalently couple the one or more compounds to the molecule(s) and which do not interfere with the biological activity of the compounds. The linker may be attached to any part of the compounds so long as the point of attachment does not interfere with the biological activity, for example, the anti-tumor and/or anti-inflammatory activity of the compounds described herein.

In one embodiment, the compounds are conjugated to a second molecule through a reactive functional group on the compound, such as an ester, followed by reaction of the ester with a nucleophilic functional group on the molecule to be linked. The esters may be prepared, for example, by reaction of a carboxyl group on the compound with an alcohol in the presence of a dehydration agent such as dicyclohexylcarbodiimide (DCC), 1-(3-dimethylaminopropyl)-3-ethylcarbodiimide (EDC), or 1-(3-dimethylamino propyl)-3-ethylcarbodiimide methiodide (EDCI). The agent to be linked to the compound(s), for example, a tumor-specific antibody, is then mixed with the activated ester in aqueous solution to form the conjugate.

Alternatively, the ester of the compounds(s) may be prepared as described above and reacted with a linker group, for example, 2-aminoethanol, an alkylene diamine, an amino acid such as glycine, or a carboxy-protected amino acid such as glycine tert-butyl ester. If the linker contains a protected carboxy group, the protecting group is removed and the ester of the linker is prepared (as described above). The active ester is then reacted with the second molecule to give the conjugate. In another embodiment, the second agent can be derivatized with succinic anhydride to give an agent-succinate conjugate, which may be condensed in the presence of EDC or EDCI with a linker having a free amino or hydroxyl group.

It also is possible to prepare a compound containing a linker with a free amino group and crosslink the free amino group with a heterobifunctional cross linker such as sulfo-succinimidyl 4-(N-maleimidocyclohexane)-1-carboxylate which will react with the free sulfhydryl groups of protein antigens.

The compounds may also be coupled to a linker by reaction of the aldehyde group with an amino linker to form an intermediate imine conjugate, followed by reduction with sodium borohydride or sodium cyanoborohydride. Examples of such linkers include amino alcohols such as 2-aminoethanol and diamino compounds such as ethylenediamine, 1,2-propylenediamine, 1,5-pentanediamine, 1,6-hexanediamine, and the like. The compounds may then be coupled to the linker by first forming the succinated derivative with succinic anhydride followed by condensation with the linker with DCC, EDC.

In addition, the compounds may be oxidized with periodate and the resulting dialdehyde condensed with an amino alcohol or diamino compound listed above. The free hydroxyl or amino group on the linker may then be condensed with the succinate derivative of the antigen in the presence of DCC, EDC or EDCI. Many types of linkers are known in the art and may be used in the creation of conjugates. A non-limiting list of exemplary linkers is shown in Table 4.

TABLE 4

Examples of hetero-bifunctional cross-linking agents
Hetero-Bifunctional Cross Linking Agents

| Linker | Reactive Toward | Advantages and Applications | Spacer Arm Length after crosslinking (angstroms) |
|---|---|---|---|
| SMPT | Primary amines Sulfhydryls | Greater stability | 11.2 |
| SPDP | Primary amines Sulfhydryls | Thiolation Cleavable cross-linking | 6.8 |
| LC-SPDP | Primary amines Sulfhydryls | Extended spacer arm | 15.6 |
| Sulfo-LC-SPDP | Primary amines Sulfhydryls | Extended spacer arm Water soluble | 15.6 |
| SMCC | Primary amines Sulfhydryls | Stable maleimide reactive group Enzyme-antibody conjugation Hapten-carrier protein conjugation | 11.6 |
| Sulfo-SMCC | Primary amines Sulfhydryls | Stable maleimide reactive group Enzyme-antibody conjugation | 11.6 |
| MBS | Primary amines Sulfhydryls | Enzyme-antibody conjugation Hapten-carrier protein conjugation | 9.9 |
| Sulfo-MBS | Primary amines Sulfhydryls | Water soluble | 9.9 |
| SIAB | Primary amines Sulfhydryls | Enzyme-antibody conjugation | 10.6 |
| Sulfo-SIAB | Primary amines Sulfhydryls | Water soluble | 10.6 |
| SMPB | Primary amines Sulfhydryls | Extended spacer arm Enzyme-antibody conjugation | 14.5 |
| Sulfo-SMPB | Primary amines Sulfhydryls | Extended spacer arm Water-soluble | 14.5 |
| EDC/Sulfo-NHS | Primary amines Carboxyl groups | Hapten-carrier conjugation | 0 |
| ABH | Carbohydrates Non-selective | Reacts with sugar moieties | 11.9 |

III. Pharmaceutical Compositions

The compounds described herein can be formulated for enteral, parenteral, topical, or pulmonary administration. The compounds can be combined with one or more pharmaceutically acceptable carriers and/or excipients that are considered safe and effective and may be administered to an individual without causing undesirable biological side effects or unwanted interactions. The carrier is all components present in the pharmaceutical formulation other than the active ingredient or ingredients.

A. Parenteral Formulations

The compounds described herein can be formulated for parenteral administration. "Parenteral administration", as used herein, means administration by any method other than through the digestive tract or non-invasive topical or regional routes. For example, parenteral administration may include administration to a patient intravenously, intradermally, intraarterially, intraperitoneally, intralesionally, intracranially, intraarticularly, intraprostatically, intrapleurally, intratracheally, intravitreally, intratumorally, intramuscularly, subcutaneously, subconjunctivally, intravesicularly, intrapericardially, intraumbilically, by injection, and by infusion.

Parenteral formulations can be prepared as aqueous compositions using techniques is known in the art. Typically, such compositions can be prepared as injectable formulations, for example, solutions or suspensions; solid forms suitable for using to prepare solutions or suspensions upon the addition of a reconstitution medium prior to injection; emulsions, such as water-in-oil (w/o) emulsions, oil-in-water (o/w) emulsions, and microemulsions thereof, liposomes, or emulsomes.

The carrier can be a solvent or dispersion medium containing, for example, water, ethanol, one or more polyols (e.g., glycerol, propylene glycol, and liquid polyethylene glycol), oils, such as vegetable oils (e.g., peanut oil, corn oil, sesame oil, etc.), and combinations thereof. The proper fluidity can be maintained, for example, by the use of a coating, such as lecithin, by the maintenance of the required particle size in the case of dispersion and/or by the use of surfactants. In many cases, it will be preferable to include isotonic agents, for example, sugars or sodium chloride.

Solutions and dispersions of the active compounds as the free acid or base or pharmacologically acceptable salts thereof can be prepared in water or another solvent or dispersing medium suitably mixed with one or more pharmaceutically acceptable excipients including, but not limited to, surfactants, dispersants, emulsifiers, pH modifying agents, viscosity modifying agents, and combination thereof.

Suitable surfactants may be anionic, cationic, amphoteric or nonionic surface-active agents. Suitable anionic surfactants include, but are not limited to, those containing carboxylate, sulfonate and sulfate ions. Examples of anionic surfactants include sodium, potassium, ammonium of long chain alkyl sulfonates and alkyl aryl sulfonates such as sodium dodecylbenzene sulfonate; dialkyl sodium sulfosuccinates, such as sodium dodecylbenzene sulfonate; dialkyl sodium sulfosuccinates, such as sodium bis-(2-ethylthioxyl)-sulfosuccinate; and alkyl sulfates such as sodium lauryl sulfate. Cationic surfactants include, but are not limited to, quaternary ammonium compounds such as benzalkonium chloride, benzethonium chloride, cetrimonium bromide, stearyl dimethylbenzyl ammonium chloride, polyoxyethylene and coconut amine. Examples of nonionic surfactants include ethylene glycol monostearate, propylene glycol myristate, glyceryl monostearate, glyceryl stearate, polyglyceryl-4-oleate, sorbitan acylate, sucrose acylate, PEG-150 laurate, PEG-400 monolaurate, polyoxyethylene monolaurate, polysorbates, polyoxyethylene octylphenylether, PEG-1000 cetyl ether, polyoxyethylene tridecyl ether, polypropylene glycol butyl ether, Poloxamer® 401, stearoyl monoisopropanolamide, and polyoxyethylene hydrogenated tallow amide. Examples of amphoteric surfactants include sodium N-dodecyl-.beta.-alanine, sodium N-lauryl-.beta.-iminodipropionate, myristoamphoacetate, lauryl betaine and lauryl sulfobetaine.

The formulation can contain a preservative to prevent the growth of microorganisms. Suitable preservatives include, but are not limited to, parabens, chlorobutanol, phenol, sorbic acid, and thimerosal. The formulation may also contain an antioxidant to prevent degradation of the active agent(s).

The formulation is typically buffered to a pH of 3-8 for parenteral administration upon reconstitution. Suitable buffers include, but are not limited to, phosphate buffers, acetate buffers, and citrate buffers.

Water-soluble polymers are often used in formulations for parenteral administration. Suitable water-soluble polymers include, but are not limited to, polyvinylpyrrolidone, dextran, carboxymethylcellulose, and polyethylene glycol.

Sterile injectable solutions can be prepared by incorporating the active compounds in the required amount in the appropriate solvent or dispersion medium with one or more of the excipients listed above, as required, followed by filtered sterilization. Generally, dispersions are prepared by incorporating the various sterilized active ingredients into a sterile vehicle which contains the basic dispersion medium and the required other ingredients from those listed above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof. The powders can be prepared in such a manner that the particles are porous in nature, which can increase dissolution of the particles. Methods for making porous particles are well known in the art.

1. Controlled Release Formulations

The parenteral formulations described herein can be formulated for controlled release including immediate release, delayed release, extended release, pulsatile release, and combinations thereof.

i. Nano- and Microparticles

For parenteral administration, the one or more compounds, and optional one or more additional active agents, can be incorporated into microparticles, nanoparticles, or combinations thereof that provide controlled release of the compounds and/or one or more additional active agents. In embodiments wherein the formulations contains two or more drugs, the drugs can be formulated for the same type of controlled release (e.g., delayed, extended, immediate, or pulsatile) or the drugs can be independently formulated for different types of release (e.g., immediate and delayed, immediate and extended, delayed and extended, delayed and pulsatile, etc.).

For example, the compounds and/or one or more additional active agents can be incorporated into polymeric microparticles, which provide controlled release of the drug(s). Release of the drug(s) is controlled by diffusion of the drug(s) out of the microparticles and/or degradation of the polymeric particles by hydrolysis and/or enzymatic degradation. Suitable polymers include ethylcellulose and other natural or synthetic cellulose derivatives.

Polymers, which are slowly soluble and form a gel in an aqueous environment, such as hydroxypropyl methylcellulose or polyethylene oxide, may also be suitable as materials for drug containing microparticles. Other polymers include, but are not limited to, polyanhydrides, poly(ester anhydrides), polyhydroxy acids, such as polylactide (PLA), polyglycolide (PGA), poly(lactide-co-glycolide) (PLGA), poly-3-hydroxybutyrate (PHB) and copolymers thereof, poly-4-hydroxybutyrate (P4HB) and copolymers thereof, polycaprolactone and copolymers thereof, and combinations thereof.

Alternatively, the drug(s) can be incorporated into microparticles prepared from materials which are insoluble in aqueous solution or slowly soluble in aqueous solution, but are capable of degrading within the GI tract by means including enzymatic degradation, surfactant action of bile acids, and/or mechanical erosion. As used herein, the term "slowly soluble in water" refers to materials that are not dissolved in water within a period of 30 minutes. Preferred examples include fats, fatty substances, waxes, wax-like substances and mixtures thereof. Suitable fats and fatty substances include fatty alcohols (such as lauryl, myristyl stearyl, cetyl or cetostearyl alcohol), fatty acids and derivatives, including but not limited to fatty acid esters, fatty acid glycerides (mono-, di- and tri-glycerides), and hydrogenated fats. Specific examples include, but are not limited to hydrogenated vegetable oil, hydrogenated cottonseed oil, hydrogenated castor oil, hydrogenated oils available under the trade name Sterotex®, stearic acid, cocoa butter, and stearyl alcohol. Suitable waxes and wax-like materials include natural or synthetic waxes, hydrocarbons, and normal waxes. Specific examples of waxes include beeswax, glycowax, castor wax, carnauba wax, paraffins and candelilla wax. As used herein, a wax-like material is defined as any material, which is normally solid at room temperature and has a melting point of from about 30 to 300° C.

In some cases, it may be desirable to alter the rate of water penetration into the microparticles. To this end, rate-controlling (wicking) agents may be formulated along with the fats or waxes listed above. Examples of rate-controlling materials include certain starch derivatives (e.g., waxy maltodextrin and drum dried corn starch), cellulose derivatives (e.g., hydroxypropylmethyl-cellulose, hydroxypropyl-cellulose, methylcellulose, and carboxymethyl-cellulose), alginic acid, lactose and talc. Additionally, a pharmaceutically acceptable surfactant (for example, lecithin) may be added to facilitate the degradation of such microparticles.

Proteins, which are water insoluble, such as zein, can also be used as materials for the formation of drug containing microparticles. Additionally, proteins, polysaccharides and combinations thereof, which are water-soluble, can be formulated with drug into microparticles and subsequently cross-linked to form an insoluble network. For example, cyclodextrins can be complexed with individual drug molecules and subsequently cross-linked.

Encapsulation or incorporation of drug into carrier materials to produce drug-containing microparticles can be achieved through known pharmaceutical formulation techniques. In the case of formulation in fats, waxes or wax-like materials, the carrier material is typically heated above its melting temperature and the drug is added to form a mixture comprising drug particles suspended in the carrier material, drug dissolved in the carrier material, or a mixture thereof. Microparticles can be subsequently formulated through several methods including, but not limited to, the processes of congealing, extrusion, spray chilling or aqueous dispersion. In a preferred process, wax is heated above its melting temperature, drug is added, and the molten wax-drug mixture is congealed under constant stirring as the mixture cools. Alternatively, the molten wax-drug mixture can be extruded and spheronized to form pellets or beads. These processes are known in the art.

For some carrier materials it may be desirable to use a solvent evaporation technique to produce drug-containing microparticles. In this case drug and carrier material are co-dissolved in a mutual solvent and microparticles can subsequently be produced by several techniques including, but not limited to, forming an emulsion in water or other appropriate media, spray drying or by evaporating off the solvent from the bulk solution and milling the resulting material.

In some embodiments, drug in a particulate form is homogeneously dispersed in a water-insoluble or slowly water soluble material. To minimize the size of the drug particles within the composition, the drug powder itself may be milled to generate fine particles prior to formulation. The process of jet milling, known in the pharmaceutical art, can be used for this purpose. In some embodiments drug in a particulate form is homogeneously dispersed in a wax or wax like substance by heating the wax or wax like substance above its melting point and adding the drug particles while stirring the mixture. In this case a pharmaceutically acceptable surfactant may be added to the mixture to facilitate the dispersion of the drug particles.

The particles can also be coated with one or more modified release coatings. Solid esters of fatty acids, which are hydrolyzed by lipases, can be spray coated onto microparticles or drug particles. Zein is an example of a naturally water-insoluble protein. It can be coated onto drug containing microparticles or drug particles by spray coating or by wet granulation techniques. In addition to naturally water-insoluble materials, some substrates of digestive enzymes can be treated with cross-linking procedures, resulting in the formation of non-soluble networks. Many methods of cross-linking proteins, initiated by both chemical and physical means, have been reported. One of the most common methods to obtain cross-linking is the use of chemical cross-linking agents. Examples of chemical cross-linking agents include aldehydes (gluteraldehyde and formaldehyde), epoxy compounds, carbodiimides, and genipin. In addition to these cross-linking agents, oxidized and native sugars have been used to cross-link gelatin. Cross-linking can also be accomplished using enzymatic means; for example, transglutaminase has been approved as a GRAS substance for cross-linking seafood products. Finally, cross-linking can be initiated by physical means such as thermal treatment, UV irradiation and gamma irradiation.

To produce a coating layer of cross-linked protein surrounding drug containing microparticles or drug particles, a water-soluble protein can be spray coated onto the microparticles and subsequently cross-linked by the one of the methods described above. Alternatively, drug-containing microparticles can be microencapsulated within protein by coacervation-phase separation (for example, by the addition of salts) and subsequently cross-linked. Some suitable proteins for this purpose include gelatin, albumin, casein, and gluten.

Polysaccharides can also be cross-linked to form a water-insoluble network. For many polysaccharides, this can be accomplished by reaction with calcium salts or multivalent cations, which cross-link the main polymer chains. Pectin, alginate, dextran, amylose and guar gum are subject to cross-linking in the presence of multivalent cations. Complexes between oppositely charged polysaccharides can also be formed; pectin and chitosan, for example, can be complexed via electrostatic interactions.

In certain embodiments, it may be desirable to provide continuous delivery of one or more compounds to a patient in need thereof. For intravenous or intraarterial routes, this can be accomplished using drip systems, such as by intravenous administration. For topical applications, repeated application can be done or a patch can be used to provide continuous administration of the compounds over an extended period of time.

2. Injectable/Implantable Solid Implants

The compounds described herein can be incorporated into injectable/implantable solid or semi-solid implants, such as polymeric implants. In one embodiment, the compounds are incorporated into a polymer that is a liquid or paste at room temperature, but upon contact with aqueous medium, such as physiological fluids, exhibits an increase in viscosity to form a semi-solid or solid material. Exemplary polymers include, but are not limited to, hydroxyalkanoic acid polyesters derived from the copolymerization of at least one unsaturated hydroxy fatty acid copolymerized with hydroxyalkanoic acids. The polymer can be melted, mixed with the active substance and cast or injection molded into a device. Such melt fabrication require polymers having a melting point that is below the temperature at which the substance to be delivered and polymer degrade or become reactive. The device can also be prepared by solvent casting where the polymer is dissolved in a solvent and the drug dissolved or dispersed in the polymer solution and the solvent is then evaporated. Solvent processes require that the polymer be soluble in organic solvents. Another method is compression molding of a mixed powder of the polymer and the drug or polymer particles loaded with the active agent.

Alternatively, the compounds can be incorporated into a polymer matrix and molded, compressed, or extruded into a device that is a solid at room temperature. For example, the compounds can be incorporated into a biodegradable polymer, such as polyanhydrides, polyhydroalkanoic acids (MAO, PLA, PGA, PLGA, polycaprolactone, polyesters, polyamides, polyorthoesters, polyphosphazenes, proteins and polysaccharides such as collagen, hyaluronic acid, albumin and gelatin, and combinations thereof and compressed into solid device, such as disks, or extruded into a device, such as rods.

The release of the one or more compounds from the implant can be varied by selection of the polymer, the molecular weight of the polymer, and/ir modification of the polymer to increase degradation, such as the formation of pores and/or incorporation of hydrolyzable linkages. Methods for modifying the properties of biodegradable polymers to vary the release profile of the compounds from the implant are well known in the art.

B. Enteral Formulations

Suitable oral dosage forms include tablets, capsules, solutions, suspensions, syrups, and lozenges. Tablets can be made using compression or molding techniques well known in the art. Gelatin or non-gelatin capsules can prepared as hard or soft capsule shells, which can encapsulate liquid, solid, and semi-solid fill materials, using techniques well known in the art.

Formulations may be prepared using a pharmaceutically acceptable carrier. As generally used herein "carrier" includes, but is not limited to, diluents, preservatives, binders, lubricants, disintegrators, swelling agents, fillers, stabilizers, and combinations thereof.

Carrier also includes all components of the coating composition, which may include plasticizers, pigments, colorants, stabilizing agents, and glidants. Delayed release dosage formulations may be prepared as described in standard references. These references provide information on carriers, materials, equipment and process for preparing tablets and capsules and delayed release dosage forms of tablets, capsules, and granules.

Examples of suitable coating materials include, but are not limited to, cellulose polymers such as cellulose acetate phthalate, hydroxypropyl cellulose, hydroxypropyl methylcellulose, hydroxypropyl methylcellulose phthalate and hydroxypropyl methylcellulose acetate succinate; polyvinyl acetate phthalate, acrylic acid polymers and copolymers, and methacrylic resins that are commercially available under the trade name EUDRAGIT® (Roth Pharma, Westerstadt, Germany), zein, shellac, and polysaccharides.

Additionally, the coating material may contain conventional carriers such as plasticizers, pigments, colorants, glidants, stabilization agents, pore formers and surfactants.

Optional pharmaceutically acceptable excipients include, but are not limited to, diluents, binders, lubricants, disintegrants, colorants, stabilizers, and surfactants. Diluents, also referred to as "fillers," are typically necessary to increase the bulk of a solid dosage form so that a practical size is provided for compression of tablets or formation of beads and granules. Suitable diluents include, but are not limited to, dicalcium phosphate dihydrate, calcium sulfate, lactose, sucrose, mannitol, sorbitol, cellulose, microcrystalline cellulose, kaolin, sodium chloride, dry starch, hydrolyzed starches, pregelatinized starch, silicone dioxide, titanium oxide, magnesium aluminum silicate and powdered sugar.

Binders are used to impart cohesive qualities to a solid dosage formulation, and thus ensure that a tablet or bead or granule remains intact after the formation of the dosage forms. Suitable binder materials include, but are not limited to, starch, pregelatinized starch, gelatin, sugars (including sucrose, glucose, dextrose, lactose and sorbitol), polyethylene glycol, waxes, natural and synthetic gums such as acacia, tragacanth, sodium alginate, cellulose, including hydroxypropylmethylcellulose, hydroxypropylcellulose, ethylcellulose, and veegum, and synthetic polymers such as acrylic acid and methacrylic acid copolymers, methacrylic acid copolymers, methyl methacrylate copolymers, aminoalkyl methacrylate copolymers, polyacrylic acid/polymethacrylic acid and polyvinylpyrrolidone.

Lubricants are used to facilitate tablet manufacture. Examples of suitable lubricants include, but are not limited to, magnesium stearate, calcium stearate, stearic acid, glycerol behenate, polyethylene glycol, talc, and mineral oil.

Disintegrants are used to facilitate dosage form disintegration or "breakup" after administration, and generally include, but are not limited to, starch, sodium starch glycolate, sodium carboxymethyl starch, sodium carboxymethylcellulose, hydroxypropyl cellulose, pregelatinized starch, clays, cellulose, alginine, gums or cross linked polymers, such as cross-linked PVP (Polyplasdone® XL from GAF Chemical Corp).

Stabilizers are used to inhibit or retard drug decomposition reactions, which include, by way of example, oxidative reactions. Suitable stabilizers include, but are not limited to, antioxidants, butylated hydroxytoluene (BHT); ascorbic acid, its salts and esters; Vitamin E, tocopherol and its salts; sulfites such as sodium metabisulphite; cysteine and its derivatives; citric acid; propyl gallate, and butylated hydroxyanisole (BHA).

i. Controlled Release Formulations

Oral dosage forms, such as capsules, tablets, solutions, and suspensions, can for formulated for controlled release. For example, the one or more compounds and optional one or more additional active agents can be formulated into nanoparticles, microparticles, and combinations thereof, and encapsulated in a soft or hard gelatin or non-gelatin capsule or dispersed in a dispersing medium to form an oral suspension or syrup. The particles can be formed of the drug and a controlled release polymer or matrix. Alternatively, the drug particles can be coated with one or more controlled release coatings prior to incorporation in to the finished dosage form.

In another embodiment, the one or more compounds and optional one or more additional active agents are dispersed in a matrix material, which gels or emulsifies upon contact with an aqueous medium, such as physiological fluids. In the case of gels, the matrix swells entrapping the active agents, which are released slowly over time by diffusion and/or degradation of the matrix material. Such matrices can be formulated as tablets or as fill materials for hard and soft capsules.

In still another embodiment, the one or more compounds, and optional one or more additional active agents are formulated into a sold oral dosage form, such as a tablet or capsule, and the solid dosage form is coated with one or more controlled release coatings, such as a delayed release coatings or extended release coatings. The coating or coatings may also contain the compounds and/or additional active agents.

Extended Release Dosage Forms

The extended release formulations are generally prepared as diffusion or osmotic systems, which are known in the art. A diffusion system typically consists of two types of devices, a reservoir and a matrix, and is well known and described in the art. The matrix devices are generally prepared by compressing the drug with a slowly dissolving polymer carrier into a tablet form. The three major types of materials used in the preparation of matrix devices are insoluble plastics, hydrophilic polymers, and fatty compounds. Plastic matrices include, but are not limited to, methyl acrylate-methyl methacrylate, polyvinyl chloride, and polyethylene. Hydrophilic polymers include, but are not limited to, cellulosic polymers such as methyl and ethyl cellulose, hydroxyalkylcelluloses such as hydroxypropyl-cellulose, hydroxypropylmethylcellulose, sodium carboxymethylcellulose, and Carbopol® 934, polyethylene oxides and mixtures thereof. Fatty compounds include, but are not limited to, various waxes such as carnauba wax and glyceryl tristearate and wax-type substances including hydrogenated castor oil or hydrogenated vegetable oil, or mixtures thereof.

In certain preferred embodiments, the plastic material is a pharmaceutically acceptable acrylic polymer, including but not limited to, acrylic acid and methacrylic acid copolymers, methyl methacrylate, methyl methacrylate copolymers, ethoxyethyl methacrylates, cyanoethyl methacrylate, aminoalkyl methacrylate copolymer, poly(acrylic acid), poly(methacrylic acid), methacrylic acid alkylamine copolymer poly(methyl methacrylate), poly(methacrylic acid)(anhydride), polymethacrylate, polyacrylamide, poly(methacrylic acid anhydride), and glycidyl methacrylate copolymers.

In certain preferred embodiments, the acrylic polymer is comprised of one or more ammonio methacrylate copolymers. Ammonio methacrylate copolymers are well known in the art, and are described in NF XVII as fully polymerized copolymers of acrylic and methacrylic acid esters with a low content of quaternary ammonium groups.

In one preferred embodiment, the acrylic polymer is an acrylic resin lacquer such as that which is commercially available from Rohm Pharma under the tradename Eudragit®. In further preferred embodiments, the acrylic polymer comprises a mixture of two acrylic resin lacquers commercially available from Rohm Pharma under the tradenames Eudragit® RL30D and Eudragit® RS30D, respectively. Eudragit® RL30D and Eudragit® RS30D are copolymers of acrylic and methacrylic esters with a low content of quaternary ammonium groups, the molar ratio of ammonium groups to the remaining neutral (meth)acrylic esters being 1:20 in Eudragit® RL30D and 1:40 in Eudragit® RS30D. The mean molecular weight is about 150,000. Edragit® S-100 and Eudragit® L-100 are also preferred. The code designations RL (high permeability) and RS (low permeability) refer to the permeability properties of these agents. Eudragit® RL/RS mixtures are insoluble in water and in digestive fluids. However, multiparticulate systems formed to include the same are swellable and permeable in aqueous solutions and digestive fluids.

The polymers described above such as Eudragit® RL/RS may be mixed together in any desired ratio in order to ultimately obtain a sustained-release formulation having a desirable dissolution profile. Desirable sustained-release multiparticulate systems may be obtained, for instance, from 100% Eudragit® RL, 50% Eudragit® RL and 50% Eudragit® RS, and 10% Eudragit® RL and 90% Eudragit® RS. One skilled in the art will recognize that other acrylic polymers may also be used, such as, for example, Eudragit® L.

Alternatively, extended release formulations can be prepared using osmotic systems or by applying a semi-permeable coating to the dosage form. In the latter case, the desired drug release profile can be achieved by combining low permeable and high permeable coating materials in suitable proportion.

The devices with different drug release mechanisms described above can be combined in a final dosage form comprising single or multiple units. Examples of multiple units include, but are not limited to, multilayer tablets and capsules containing tablets, beads, or granules. An immediate release portion can be added to the extended release system by means of either applying an immediate release layer on top of the extended release core using a coating or compression process or in a multiple unit system such as a capsule containing extended and immediate release beads.

Extended release tablets containing hydrophilic polymers are prepared by techniques commonly known in the art such as direct compression, wet granulation, or dry granulation. Their formulations usually incorporate polymers, diluents, binders, and lubricants as well as the active pharmaceutical ingredient. The usual diluents include inert powdered substances such as starches, powdered cellulose, especially crystalline and microcrystalline cellulose, sugars such as fructose, mannitol and sucrose, grain flours and similar edible powders. Typical diluents include, for example, various types of starch, lactose, mannitol, kaolin, calcium phosphate or sulfate, inorganic salts such as sodium chloride and powdered sugar. Powdered cellulose derivatives are also useful. Typical tablet binders include substances such as starch, gelatin and sugars such as lactose, fructose, and glucose. Natural and synthetic gums, including acacia, alginates, methylcellulose, and polyvinylpyrrolidone can also be used. Polyethylene glycol, hydrophilic polymers, ethylcellulose and waxes can also serve as binders. A lubricant is necessary in a tablet formulation to prevent the tablet and punches from sticking in the die. The lubricant is chosen from such slippery solids as talc, magnesium and calcium stearate, stearic acid and hydrogenated vegetable oils.

Extended release tablets containing wax materials are generally prepared using methods known in the art such as a direct blend method, a congealing method, and an aqueous dispersion method. In the congealing method, the drug is mixed with a wax material and either spray-congealed or congealed and screened and processed.

Delayed Release Dosage Forms

Delayed release formulations can be created by coating a solid dosage form with a polymer film, which is insoluble in the acidic environment of the stomach, and soluble in the neutral environment of the small intestine.

The delayed release dosage units can be prepared, for example, by coating a drug or a drug-containing composition with a selected coating material. The drug-containing composition may be, e.g., a tablet for incorporation into a capsule, a tablet for use as an inner core in a "coated core" dosage form, or a plurality of drug-containing beads, particles or granules, for incorporation into either a tablet or capsule. Preferred coating materials include bioerodible, gradually hydrolyzable, gradually water-soluble, and/or enzymatically degradable polymers, and may be conventional "enteric" polymers. Enteric polymers, as will be appreciated by those skilled in the art, become soluble in the higher pH environment of the lower gastrointestinal tract or slowly erode as the dosage form passes through the gastrointestinal tract, while enzymatically degradable polymers are degraded by bacterial enzymes present in the lower gastrointestinal tract, particularly in the colon. Suitable coating materials for effecting delayed release include, but are not limited to, cellulosic polymers such as hydroxypropyl cellulose, hydroxyethyl cellulose, hydroxymethyl cellulose, hydroxypropyl methyl cellulose, hydroxypropyl methyl cellulose acetate succinate, hydroxypropylmethyl cellulose phthalate, methylcellulose, ethyl cellulose, cellulose acetate, cellulose acetate phthalate, cellulose acetate trimellitate and carboxymethylcellulose sodium; acrylic acid polymers and copolymers, preferably formed from acrylic acid, methacrylic acid, methyl acrylate, ethyl acrylate, methyl methacrylate and/or ethyl methacrylate, and other methacrylic resins that are commercially available under the tradename Eudragit® (Rohm Pharma; Westerstadt, Germany), including Eudragit® L30D-55 and L100-55 (soluble at pH 5.5 and above), Eudragit® L-100 (soluble at pH 6.0 and above), Eudragit® S (soluble at pH 7.0 and above, as a result of a higher degree of esterification), and Eudragits® NE, RL and RS (water-insoluble polymers having different degrees of permeability and expandability); vinyl polymers and copolymers such as polyvinyl pyrrolidone, vinyl acetate, vinylacetate phthalate, vinylacetate crotonic acid copolymer, and ethylene-vinyl acetate copolymer; enzymatically degradable polymers such as azo polymers, pectin, chitosan, amylose and guar gum; zein and shellac. Combinations of different coating materials may also be used. Multi-layer coatings using different polymers may also be applied.

The preferred coating weights for particular coating materials may be readily determined by those skilled in the art by evaluating individual release profiles for tablets, beads and granules prepared with different quantities of various coating materials. It is the combination of materials, method and form of application that produce the desired release characteristics, which one can determine only from the clinical studies.

The coating composition may include conventional additives, such as plasticizers, pigments, colorants, stabilizing agents, glidants, etc. A plasticizer is normally present to reduce the fragility of the coating, and will generally represent about 10 wt. % to 50 wt. % relative to the dry weight of the polymer. Examples of typical plasticizers include polyethylene glycol, propylene glycol, triacetin, dimethyl phthalate, diethyl phthalate, dibutyl phthalate, dibutyl sebacate, triethyl citrate, tributyl citrate, triethyl acetyl citrate, castor oil and acetylated monoglycerides. A stabilizing agent is preferably used to stabilize particles in the dispersion. Typical stabilizing agents are nonionic emulsifiers such as sorbitan esters, polysorbates and polyvinylpyrrolidone. Glidants are recommended to reduce sticking effects during film formation and drying, and will generally represent approximately 25 wt. % to 100 wt. % of the polymer weight in the coating solution. One effective glidant is talc. Other glidants such as magnesium stearate and glycerol monostearates may also be used. Pigments such as titanium dioxide may also be used. Small quantities of an anti-foaming agent, such as a silicone (e.g., simethicone), may also be added to the coating composition.

C. Topical Formulations

Suitable dosage forms for topical administration include creams, ointments, salves, sprays, gels, lotions, emulsions, and transdermal patches. The formulation may be formulated for transmucosal, transepithelial, transendothelial, or transdermal administration. The compounds can also be formulated for intranasal delivery, pulmonary delivery, or inhalation. The compositions may further contain one or more chemical penetration enhancers, membrane permeability agents, membrane transport agents, emollients, surfactants, stabilizers, and combination thereof.

1. Topical Formulations

"Emollients" are an externally applied agent that softens or soothes skin and are generally known in the art and listed in compendia, such as the "Handbook of Pharmaceutical Excipients", $4^{th}$ Ed., Pharmaceutical Press, 2003. These include, without limitation, almond oil, castor oil, ceratonia extract, cetostearoyl alcohol, cetyl alcohol, cetyl esters wax, cholesterol, cottonseed oil, cyclomethicone, ethylene glycol palmitostearate, glycerin, glycerin monostearate, glyceryl monooleate, isopropyl myristate, isopropyl palmitate, lanolin, lecithin, light mineral oil, medium-chain triglycerides, mineral oil and lanolin alcohols, petrolatum, petrolatum and lanolin alcohols, soybean oil, starch, stearyl alcohol, sunflower oil, xylitol and combinations thereof. In one embodiment, the emollients are ethylhexylstearate and ethylhexyl palmitate.

"Surfactants" are surface-active agents that lower surface tension and thereby increase the emulsifying, foaming, dispersing, spreading and wetting properties of a product. Suitable non-ionic surfactants include emulsifying wax, glyceryl monooleate, polyoxyethylene alkyl ethers, polyoxyethylene castor oil derivatives, polysorbate, sorbitan esters, benzyl alcohol, benzyl benzoate, cyclodextrins, glycerin monostearate, poloxamer, povidone and combinations thereof. In one embodiment, the non-ionic surfactant is stearyl alcohol.

"Emulsifiers" are surface active substances which promote the suspension of one liquid in another and promote the formation of a stable mixture, or emulsion, of oil and water. Common emulsifiers are: metallic soaps, certain animal and vegetable oils, and various polar compounds. Suitable emulsifiers include acacia, anionic emulsifying wax, calcium stearate, carbomers, cetostearyl alcohol, cetyl alcohol, cholesterol, diethanolamine, ethylene glycol palmitostearate, glycerin monostearate, glyceryl monooleate, hydroxpropyl cellulose, hypromellose, lanolin, hydrous, lanolin alcohols, lecithin, medium-chain triglycerides, methylcellulose, mineral oil and lanolin alcohols, monobasic sodium phosphate, monoethanolamine, nonionic emulsifying wax, oleic acid, poloxamer, poloxamers, polyoxyethylene alkyl ethers, polyoxyethylene castor oil derivatives, polyoxyethylene sorbitan fatty acid esters, polyoxyethylene stearates, propylene glycol alginate, self-emulsifying glyceryl monostearate, sodium citrate dehydrate, sodium lauryl sulfate, sorbitan esters, stearic acid, sunflower oil, tragacanth, triethanolamine, xanthan gum and combinations thereof. In one embodiment, the emulsifier is glycerol stearate.

Suitable classes of penetration enhancers are known in the art and include, but are not limited to, fatty alcohols, fatty acid esters, fatty acids, fatty alcohol ethers, amino acids, phospholipids, lecithins, cholate salts, enzymes, amines and amides, complexing agents (liposomes, cyclodextrins, modified celluloses, and diimides), macrocyclics, such as macrocylic lactones, ketones, and anhydrides and cyclic ureas, surfactants, N-methyl pyrrolidones and derivatives thereof, DMSO and related compounds, ionic compounds, azone and related compounds, and solvents, such as alcohols, ketones, amides, polyols (e.g., glycols). Examples of these classes are known in the art.

i. Lotions, Creams, Gels, Ointments, Emulsions, and Foams

"Hydrophilic" as used herein refers to substances that have strongly polar groups that readily interact with water.

"Lipophilic" refers to compounds having an affinity for lipids.

"Amphiphilic" refers to a molecule combining hydrophilic and lipophilic (hydrophobic) properties "Hydrophobic" as used herein refers to substances that lack an affinity for water; tending to repel and not absorb water as well as not dissolve in or mix with water.

A "gel" is a colloid in which the dispersed phase has combined with the continuous phase to produce a semisolid material, such as jelly.

An "oil" is a composition containing at least 95% wt of a lipophilic substance. Examples of lipophilic substances include but are not limited to naturally occurring and synthetic oils, fats, fatty acids, lecithins, triglycerides and combinations thereof.

A "continuous phase" refers to the liquid in which solids are suspended or droplets of another liquid are dispersed, and is sometimes called the external phase. This also refers to the fluid phase of a colloid within which solid or fluid particles are distributed. If the continuous phase is water (or another hydrophilic solvent), water-soluble or hydrophilic drugs will dissolve in the continuous phase (as opposed to being dispersed). In a multiphase formulation (e.g., an emulsion), the discreet phase is suspended or dispersed in the continuous phase.

An "emulsion" is a composition containing a mixture of non-miscible components homogenously blended together. In particular embodiments, the non-miscible components include a lipophilic component and an aqueous component. An emulsion is a preparation of one liquid distributed in small globules throughout the body of a second liquid. The dispersed liquid is the discontinuous phase, and the dispersion medium is the continuous phase. When oil is the dispersed liquid and an aqueous solution is the continuous phase, it is known as an oil-in-water emulsion, whereas when water or aqueous solution is the dispersed phase and oil or oleaginous substance is the continuous phase, it is known as a water-in-oil emulsion. Either or both of the oil phase and the aqueous phase may contain one or more surfactants, emulsifiers, emulsion stabilizers, buffers, and other excipients. Preferred excipients include surfactants, especially non-ionic surfactants; emulsifying agents, especially emulsifying waxes; and liquid non-volatile non-aqueous materials, particularly glycols such as propylene glycol. The oil phase may contain other oily pharmaceutically approved excipients. For example, materials such as hydroxylated castor oil or sesame oil may be used in the oil phase as surfactants or emulsifiers.

An emulsion is a preparation of one liquid distributed in small globules throughout the body of a second liquid. The dispersed liquid is the discontinuous phase, and the dispersion medium is the continuous phase. When oil is the dispersed liquid and an aqueous solution is the continuous phase, it is known as an oil-in-water emulsion, whereas when water or aqueous solution is the dispersed phase and oil or oleaginous substance is the continuous phase, it is known as a water-in-oil emulsion. The oil phase may consist at least in part of a propellant, such as an HFA propellant. Either or both of the oil phase and the aqueous phase may contain one or more surfactants, emulsifiers, emulsion stabilizers, buffers, and other excipients. Preferred excipients include surfactants, especially non-ionic surfactants; emulsifying agents, especially emulsifying waxes; and liquid non-volatile non-aqueous materials, particularly glycols such as propylene glycol. The oil phase may contain other oily pharmaceutically approved excipients. For example, materials such as hydroxylated castor oil or sesame oil may be used in the oil phase as surfactants or emulsifiers.

A sub-set of emulsions are the self-emulsifying systems. These drug delivery systems are typically capsules (hard shell or soft shell) comprised of the drug dispersed or dissolved in a mixture of surfactant(s) and lipophilic liquids such as oils or other water immiscible liquids. When the capsule is exposed to an aqueous environment and the outer gelatin shell dissolves, contact between the aqueous medium and the capsule contents instantly generates very small emulsion droplets. These typically are in the size range of micelles or nanoparticles. No mixing force is required to generate the emulsion as is typically the case in emulsion formulation processes.

A "lotion" is a low- to medium-viscosity liquid formulation. A lotion can contain finely powdered substances that are in soluble in the dispersion medium through the use of suspending agents and dispersing agents. Alternatively, lotions can have as the dispersed phase liquid substances that are immiscible with the vehicle and are usually dispersed by means of emulsifying agents or other suitable stabilizers. In one embodiment, the lotion is in the form of an emulsion having a viscosity of between 100 and 1000 centistokes. The fluidity of lotions permits rapid and uniform application over a wide surface area. Lotions are typically intended to dry on the skin leaving a thin coat of their medicinal components on the skin's surface.

A "cream" is a viscous liquid or semi-solid emulsion of either the "oil-in-water" or "water-in-oil type". Creams may contain emulsifying agents and/or other stabilizing agents. In one embodiment, the formulation is in the form of a cream having a viscosity of greater than 1000 centistokes, typically in the range of 20,000-50,000 centistokes. Creams are often time preferred over ointments, as they are generally easier to spread and easier to remove.

The difference between a cream and a lotion is the viscosity, which is dependent on the amount use of various oils and the percentage of water used to prepare the formulations. Creams are typically thicker than lotions, may have various uses and often one uses more varied oils/butters, depending upon the desired effect upon the skin. In a cream formulation, the water-base percentage is about 60-75% and the oil-base is about 20-30% of the total, with the other percentages being the emulsifier agent, preservatives and additives for a total of 100%.

An "ointment" is a semisolid preparation containing an ointment base and optionally one or more active agents. Examples of suitable ointment bases include hydrocarbon bases (e.g., petrolatum, white petrolatum, yellow ointment, and mineral oil); absorption bases (hydrophilic petrolatum, anhydrous lanolin, lanolin, and cold cream); water-removable bases (e.g., hydrophilic ointment), and water-soluble bases (e.g., polyethylene glycol ointments). Pastes typically differ from ointments in that they contain a larger percentage of solids. Pastes are typically more absorptive and less greasy that ointments prepared with the same components.

A "gel" is a semisolid system containing dispersions of small or large molecules in a liquid vehicle that is rendered semisolid by the action of a thickening agent or polymeric material dissolved or suspended in the liquid vehicle. The liquid may include a lipophilic component, an aqueous component or both. Some emulsions may be gels or otherwise include a gel component. Some gels, however, are not emulsions because they do not contain a homogenized blend of immiscible components. Suitable gelling agents include, but are not limited to, modified celluloses, such as hydroxypropyl cellulose and hydroxyethyl cellulose; Carbopol homopolymers and copolymers; and combinations thereof. Suitable solvents in the liquid vehicle include, but are not limited to, diglycol monoethyl ether; alklene glycols, such as propylene glycol; dimethyl isosorbide; alcohols, such as isopropyl alcohol and ethanol. The solvents are typically selected for their ability to dissolve the drug. Other additives, which improve the skin feel and/or emolliency of the formulation, may also be incorporated. Examples of such additives include, but are not limited, isopropyl myristate, ethyl acetate, $C_{12}$-$C_{15}$ alkyl benzoates, mineral oil, squalane, cyclomethicone, capric/caprylic triglycerides, and combinations thereof.

Foams consist of an emulsion in combination with a gaseous propellant. The gaseous propellant consists primarily of hydrofluoroalkanes (HFAs). Suitable propellants include HFAs such as 1,1,1,2-tetrafluoroethane (HFA 134a) and 1,1,1,2,3,3,3-heptafluoropropane (FIFA 227), but mixtures and admixtures of these and other HFAs that are currently approved or may become approved for medical use are suitable. The propellants preferably are not hydrocarbon propellant gases, which can produce flammable or explosive vapors during spraying. Furthermore, the compositions preferably contain no volatile alcohols, which can produce flammable or explosive vapors during use.

Buffers are used to control pH of a composition. Preferably, the buffers buffer the composition from a pH of about 4 to a pH of about 7.5, more preferably from a pH of about 4 to a pH of about 7, and most preferably from a pH of about 5 to a pH of about 7. In a preferred embodiment, the buffer is triethanolamine.

Preservatives can be used to prevent the growth of fungi and microorganisms. Suitable antifungal and antimicrobial agents include, but are not limited to, benzoic acid, butylparaben, ethyl paraben, methyl paraben, propylparaben, sodium benzoate, sodium propionate, benzalkonium chloride, benzethonium chloride, benzyl alcohol, cetylpyridinium chloride, chlorobutanol, phenol, phenylethyl alcohol, and thimerosal.

In certain embodiments, it may be desirable to provide continuous delivery of one or more compounds to a patient in need thereof. For topical applications, repeated application can be done or a patch can be used to provide continuous administration of the compounds over an extended period of time.

D. Pulmonary Formulations

In one embodiment, the compounds are formulated for pulmonary delivery, such as intranasal administration or oral inhalation. The respiratory tract is the structure involved in the exchange of gases between the atmosphere and the blood stream. The lungs are branching structures ultimately ending with the alveoli where the exchange of gases occurs. The alveolar surface area is the largest in the respiratory system and is where drug absorption occurs. The alveoli are covered by a thin epithelium without cilia or a mucus blanket and secrete surfactant phospholipids. The respiratory tract encompasses the upper airways, including the oropharynx and larynx, followed by the lower airways, which include the trachea followed by bifurcations into the bronchi and bronchioli. The upper and lower airways are called the conducting airways. The terminal bronchioli then divide into respiratory bronchiole, which then lead to the ultimate respiratory zone, the alveoli, or deep lung. The deep lung, or alveoli, is the primary target of inhaled therapeutic aerosols for systemic drug delivery.

Pulmonary administration of therapeutic compositions comprised of low molecular weight drugs has been observed, for example, beta-androgenic antagonists to treat asthma. Other therapeutic agents that are active in the lungs have been administered systemically and targeted via pulmonary absorption. Nasal delivery is considered to be a promising technique for administration of therapeutics for the following reasons: the nose has a large surface area available for drug absorption due to the coverage of the epithelial surface by numerous microvilli, the subepithelial layer is highly vascularized, the venous blood from the nose passes directly into the systemic circulation and therefore avoids the loss of drug by first-pass metabolism in the liver, it offers lower doses, more rapid attainment of therapeutic blood levels, quicker onset of pharmacological activity, fewer side effects, high total blood flow per $cm^3$, porous endothelial basement membrane, and it is easily accessible.

The term aerosol as used herein refers to any preparation of a fine mist of particles, which can be in solution or a suspension, whether or not it is produced using a propellant. Aerosols can be produced using standard techniques, such as ultrasonication or high-pressure treatment.

Carriers for pulmonary formulations can be divided into those for dry powder formulations and for administration as solutions. Aerosols for the delivery of therapeutic agents to the respiratory tract are known in the art. For administration via the upper respiratory tract, the formulation can be formulated into a solution, e.g., water or isotonic saline, buffered or un-buffered, or as a suspension, for intranasal administration as drops or as a spray. Preferably, such solutions or suspensions are isotonic relative to nasal secretions and of about the same pH, ranging e.g., from about pH 4.0 to about pH 7.4 or, from pH 6.0 to pH 7.0. Buffers should be physiologically compatible and include, simply by way of example, phosphate buffers. For example, a representative nasal decongestant is described as being buffered to a pH of about 6.2. One skilled in the art can readily determine a suitable saline content and pH for an innocuous aqueous solution for nasal and/or upper respiratory administration.

Preferably, the aqueous solution is water, physiologically acceptable aqueous solutions containing salts and/or buffers, such as phosphate buffered saline (PBS), or any other aqueous solution acceptable for administration to a animal or human. Such solutions are well known to a person skilled in the art and include, but are not limited to, distilled water, de-ionized water, pure or ultrapure water, saline, phosphate-buffered saline (PBS). Other suitable aqueous vehicles include, but are not limited to, Ringer's solution and isotonic sodium chloride. Aqueous suspensions may include suspending agents such as cellulose derivatives, sodium alginate, polyvinyl-pyrrolidone and gum tragacanth, and a wetting agent such as lecithin. Suitable preservatives for aqueous suspensions include ethyl and n-propyl p-hydroxybenzoate.

In another embodiment, solvents that are low toxicity organic (i.e. nonaqueous) class 3 residual solvents, such as ethanol, acetone, ethyl acetate, tetrahydofuran, ethyl ether, and propanol may be used for the formulations. The solvent is selected based on its ability to readily aerosolize the formulation. The solvent should not detrimentally react with the compounds. An appropriate solvent should be used that dissolves the compounds or forms a suspension of the compounds. The solvent should be sufficiently volatile to enable formation of an aerosol of the solution or suspension. Additional solvents or aerosolizing agents, such as freons, can be added as desired to increase the volatility of the solution or suspension.

In one embodiment, compositions may contain minor amounts of polymers, surfactants, or other excipients well known to those of the art. In this context, "minor amounts" means no excipients are present that might affect or mediate uptake of the compounds in the lungs and that the excipients that are present are present in amount that do not adversely affect uptake of compounds in the lungs.

Dry lipid powders can be directly dispersed in ethanol because of their hydrophobic character. For lipids stored in organic solvents such as chloroform, the desired quantity of solution is placed in a vial, and the chloroform is evaporated under a stream of nitrogen to form a dry thin film on the surface of a glass vial. The film swells easily when reconstituted with ethanol. To fully disperse the lipid molecules in the organic solvent, the suspension is sonicated. Nonaqueous suspensions of lipids can also be prepared in absolute ethanol using a reusable PARI LC Jet+ nebulizer (PARI Respiratory Equipment, Monterey, Calif.).

Dry powder formulations ("DPFs") with large particle size have improved flowability characteristics, such as less aggregation, easier aerosolization, and potentially less phagocytosis. Dry powder aerosols for inhalation therapy are generally produced with mean diameters primarily in the range of less than 5 microns, although a preferred range is between one and ten microns in aerodynamic diameter. Large "carrier" particles (containing no drug) have been co-delivered with therapeutic aerosols to aid in achieving efficient aerosolization among other possible benefits.

Polymeric particles may be prepared using single and double emulsion solvent evaporation, spray drying, solvent extraction, solvent evaporation, phase separation, simple and complex coacervation, interfacial polymerization, and other methods well known to those of ordinary skill in the art. Particles may be made using methods for making microspheres or microcapsules known in the art. The preferred methods of manufacture are by spray drying and freeze drying, which entails using a solution containing the surfactant, spraying to form droplets of the desired size, and removing the solvent.

The particles may be fabricated with the appropriate material, surface roughness, diameter and tap density for localized delivery to selected regions of the respiratory tract such as the deep lung or upper airways. For example, higher density or larger particles may be used for upper airway delivery. Similarly, a mixture of different sized particles, provided with the same or different EGS may be administered to target different regions of the lung in one administration.

Formulations for pulmonary delivery include unilamellar phospholipid vesicles, liposomes, or lipoprotein particles. Formulations and methods of making such formulations containing nucleic acid are well known to one of ordinary skill in the art. Liposomes are formed from commercially available phospholipids supplied by a variety of vendors including Avanti Polar Lipids, Inc. (Biuuingham, Ala.). In one embodiment, the liposome can include a ligand molecule specific for a receptor on the surface of the target cell to direct the liposome to the target cell.

E. Other Active Agents

The compounds described herein can be co-administered with one or more additional active agents, such as diagnostic agents, therapeutic agents, and/or prophylactic agents. Suitable classes of active agents include, but are not limited to:

Alkylating agents, such as nitrogen mustards (e.g., mechloroethamine, cyclophosphamide, ifosfamide, melphalan, and chlorambucil), ethylenimines and methylmelamines (e.g., heaxmethylmelamine), alkyl sulfonates (e.g., thiotepa and busulfan) nitrosoureas (e.g., carmustine, lomustine, semustine, and streptozocin), and triazines (e.g., dacarbazine);

Antimetabolites, such as folic acid and analogs thereof (e.g., methotrexate), pyrimidine analogs (e.g., fluoracil, floxuridine, and cytarabine), purine analogs and related inhibitors (e.g., mercaptopurine, thioguanine, and pentostatin), Cytotoxic anticancer agents, such as paclitaxel;

Cytostatic and/or cytotoxic agents such as anti-angiogenic agents such as endostatin, angiostatin, thalidomide;

Analgesics, such as opioid and non-opioid analgesics; and

Vaccines containing cancer antigens or immunomodulators such as cytokines to enhance the anti-cancer activity;

Natural products, such as vinca alkaloids (e.g., vinblastine and vincristine), epipodophyllotoxins (e.g., etoposide and tertiposide), antibiotics (e.g., dactinomycin, daunorubicin, doxorubicin, bleomycin, plicamycin, and mitomycin), enzymes (e.g., L-asparaginase), and biological response modifiers (e.g., interferon alpha);

Proteasome inhibitors, such as lactacystin, MG-132, and PS-341; Tyrosine kinase inhibitors, such as Gleevece, ZD 1839 (Iressa®), SH268, genistein, CEP2563, SU6668, SUI 1248, and EMD 121974;

Retinoids and synthetic retinoids, such as bexarotene, tretinoin, 13-cis-retinoic acid, 9-cis-retinoic acid, .alpha.-difluoromethylomithine, ILX23-7553, fenretinide, and N-4-carboxyphenyl retinamide;

Cyclin-dependent kinase inhibitors, such as flavopiridol, UCN-01, roscovitine and olomoucine;

COX-2 inhibitors include, such as celecoxib, valecoxib, and rofecoxib;

Prenylprotein transferase inhibitors, such as RI 15777, SCH66336, L-778,123, BAL9611 and TAN-1813;

Hormones and antagonists, such as adrenocorticosteroids (e.g., prednisone), progestins (e.g, hydroxyprogesterone caproate, medroxyprogesterone acetate, and megestrol acetate), estrogens (e.g., diethylstilbestrol and ethinyl estradiol), antiestrogen (e.g., tamoxifen), androgens (e.g., testosterone propionate, fluoxtnesterone, antiandrogen), and gonadotropin-releasing hormone analogs;

Sigma-2 receptor agonists, such as CB-64D, CB-184 and haloperidol;

HMG-CoA reductase inhibitors, such as lovastatin, simvastatin, pravastatin, fluvastatin, atorvastatin and cerivastatin;

HIV protease inhibitors, such as amprenavir, abacavir, CGP-73547, CGP-61755, DMP-450, indinavir, nelfinavir, tipranavir, ritonavir, saquinavir, ABT-378, AG 1776, and BMS-232,632;

Proteins include insulin, and

Miscellaneous compounds include platinum coordination complexes (e.g., cisplatin and carboplatin), anthracenedione (e.g., mitoxantrone), substituted urea (hydroxyurea), methyl hydrazines (e.g., procarbazine), and adrenocortical suppressants (e.g., mitotane and aminogluethimide).

The one or more compounds and the one or more additional active agents can be formulated in the same dosage form or separate dosage forms. Alternatively, the one or more additional active agents can be administered simultaneously or almost simultaneously in different dosage forms. If in separate dosage units, the one or more compounds and the one or more additional active agents can be administered by the same route of administration or by different routes of administration. For example, the one or more compounds and the one or more additional active agents can both be administered parenterally, or one can be administered parenterally and one orally.

If the one or more compounds and the one or more active agents are administered sequentially, the second agent to be administered is administered typically less than 6 hours following administration of the first agent, preferably less than 4 hours after the first agent, more preferably less than 2 hours after the first agent, more preferably less than 1 hour after the first agent, most preferably less than 30 minutes after administration of the first agent, and most preferably immediately after administration of the first agent. "Immediately", as used here, means less than 10 minutes, preferably less than 5 minutes, more preferably less than 2 minutes, most preferably less than one minute.

The compounds and the one or more additional active agents can be formulated for controlled release, for example, immediate release, delayed release, extended release, pulsatile release, and combinations thereof. In one embodiment, the one or more compounds are formulated for immediate release and the one or more additional agents are formulated for delayed, extended, or pulsatile release. In another embodiment, the one or more compounds are formulated for delayed, extended, or pulsatile release and the one or more additional active agents are formulated for immediate release. In still another embodiment, the one or more compounds and the one or more additional active agents are independently formulated for delayed, extended, or pulsatile release.

IV. Methods of Making the Compounds

The starting N-substituted 4-piperidones were synthesized using literature procedures. In general, treatment of 4-piperidone hydrochloride with p-toluene sulphonyl chloride, or benzene sulphonyl chloride or benzyl bromide or ethyl iodide in presence of anhydrous $K_2CO_3$ at room temperature in biphasic medium [$CHCl_3$:$H_2O$ (1:1)] yielded desired compounds (2a-d) in good yield (scheme 1). The acid catalyzed Claisen-Schmidt condensation of compounds 2a-d with variety of substituted benzaldehydes under reflux temperature led to the formation of desired compounds (3a-j, 4a-j, 5a-j, 6a-j) in good to excellent yield (scheme 1).

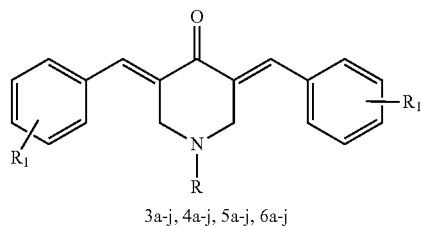

3a-j, 4a-j, 5a-j, 6a-j

C5-curcuminoid-triazole hybrids were prepared as shown in scheme 3. The starting azides were prepared by literature method as shown in scheme 2. The alkyl bromide (7a-c) on refluxing with sodium azide in presence of anhydrous $K_2CO_3$ and DMF affords desired compounds (8a-c) in good yield (scheme 2).

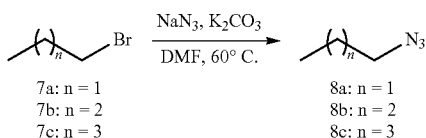

7a: n = 1
7b: n = 2
7c: n = 3

8a: n = 1
8b: n = 2
8c: n = 3

The alkyne counterparts for click reaction were prepared as shown in scheme 3. The compound 9 was synthesized via nucleophilic substitution reaction between 4-piperidone hydrochloride monohydrate and propargyl bromide in presence of anhydrous $K_2CO_3$ in the biphasic system [$CHCl_3$:$H_2O$ (1:1)] at room temperature in good yield. The compound 9 was reacted with substituted benzaldehydes in presence of 20% NaOH solution in ethanol to give compounds (11a-c, 12a-c, 13a-c, 14a-c, 15a-c, 16a-c) in very good yield (scheme 3).

Scheme 3

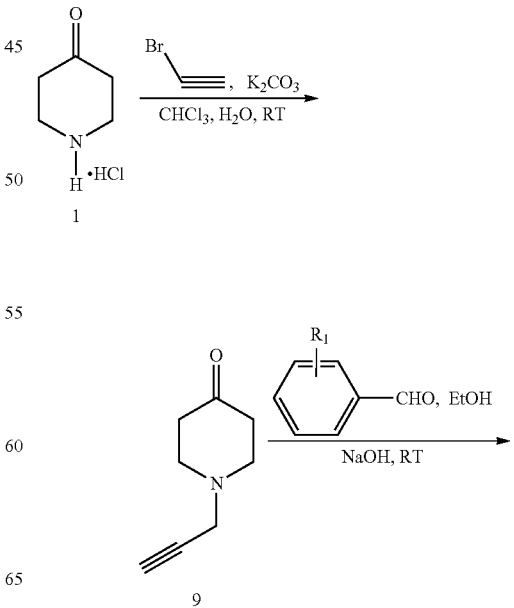

Scheme 1

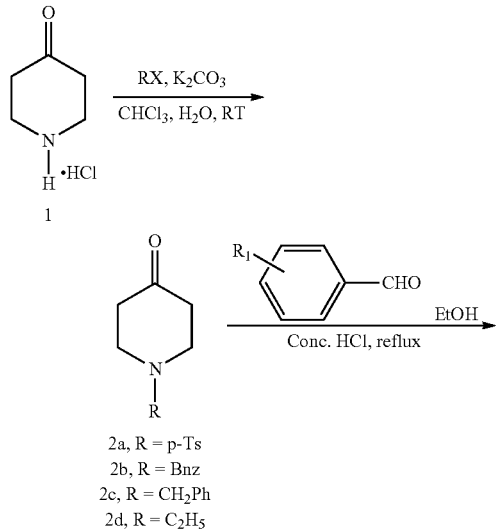

2a, R = p-Ts
2b, R = Bnz
2c, R = $CH_2Ph$
2d, R = $C_2H_5$

-continued

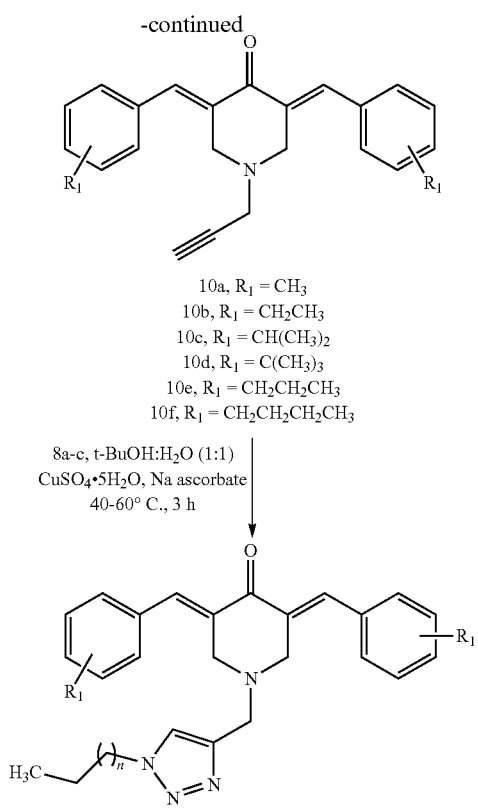

10a, R₁ = CH₃
10b, R₁ = CH₂CH₃
10c, R₁ = CH(CH₃)₂
10d, R₁ = C(CH₃)₃
10e, R₁ = CH₂CH₂CH₃
10f, R₁ = CH₂CH₂CH₂CH₃

V. Methods of Using the Compounds

The compounds described herein can be administered to a subject in need thereof to treat the subject either prophylactically (i.e., to prevent cancer) or therapeutically (i.e., to treat cancer after it has been detected), including reducing tumor growth, reducing the risk of local invasiveness of a tumor, increasing survival time of the patient, and/or reducing the risk of metastasis of a primary tumor.

The compounds described herein can contact a target cell to inhibit the initiation and promotion of cancer, to kill cancer/malignant cells, to inhibit cell growth, to induce apoptosis, to inhibit metastasis, to decrease tumor size, to otherwise reverse or reduce the malignant phenotype of tumor cells, and combinations thereof. This may be achieved by contacting a tumor or tumor cell with a single composition or pharmacological formulation that includes the compound(s), or by contacting a tumor or tumor cell with more than one distinct composition or formulation, simultaneously, wherein one composition includes one or more compounds described herein and the other includes a second agent.

Exemplary cancers, which can be treated, include, but are not limited to, cancer of the skin, colon, uterine, ovarian, pancreatic, lung, bladder, breast, renal system, and prostate. Other cancers include, but are not limited to, cancers of the brain, liver, stomach, esophagus, head and neck, testicles, cervix, lymphatic system, larynx, esophagus, parotid, biliary tract, rectum, endometrium, kidney, and thyroid; including squamous cell carcinomas, adenocarcinomas, small cell carcinomas, gliomas, neuroblastomas, and the like. Assay methods for ascertaining the relative efficacy of the compounds described herein in treating the above types of cancers as well as other cancers are well known in the art.

The compounds described herein can also be used to treat metastatic cancer either in patients who have received prior chemo, radio, or biological therapy or in previously untreated patients. In one embodiment, the patient has received previous chemotherapy. Patients can be treated using a variety of routes of administration including systemic administration, such as intravenous administration or subcutaneous administration, oral administration or by intratumoral injection.

The compounds described herein can also be used to treat patients who have been rendered free of clinical disease by surgery, chemotherapy, and/or radiotherapy. In these aspects, the purpose of therapy is to prevent or reduce the likelihood of recurrent disease. Adjuvant therapy can be administered in the same regimen as described above to prevent recurrent disease.

The compositions described herein contain an effective amount of the one or more of the compounds described herein. The amount to be administered can be readily determined by the attending physician based on a variety of factors including, but not limited to, age of the patient, weight of the patient, disease or disorder to be treated, presence of a pre-existing condition, and dosage form to be administered (e.g., immediate release versus modified release dosage form). Typically, the effective amount is from about 0.1 mg/kg/day to about 200 mg/kg/day, more preferably from 0.1 mg/kg/day to 50 mg/kg/day, more preferably from 0.1 mg/kg/day to 25 mg/kg/day, and most preferably from 0.1 mg/kg/day to 10 mg/kg/day. Dosages greater or less than this may be administered depending on the diseases or disorder to be treated.

EXAMPLES

Example 1. Synthesis and Characterization of 1-tosyl-piperidin-4-one (2a) and Related Compounds (2a-d)

Compounds 2a-d were prepared by literature methods and characterized spectroscopically. In a typical reaction, 4-piperidone hydrochloride monohydrate 1 (5 g, 29.13 mmol) was dissolved in 20 mL of a biphasic system of CHCl₃:H₂O (1:1). To this reaction mixture, $K_2CO_3$ (12.06 g, 87.40 mmol) was added followed by the addition of p-toluenesulphonyl chloride (5.5 g, 29.13 mmol). The reaction was stirred at room temperature for 4 h and progress of the reaction was monitored by thin layer chromatography. After completion, reaction mixture was extracted with chloroform. The organic layer was dried over $Na_2SO_4$ and excess of solvent was removed under vacuum. The crude product was purified by silica gel column using EtOAc/Hexane as an eluent to afford the desired compound as white solid. Yield: 8.24 g (88%); mp: 142° C.; IR (Film, cm⁻¹): 2966, 2927, 2879, 1713 (C=O), 1369, 1348, 1225, 1171, 965, 691; ¹H NMR (400 MHz, CDCl₃): δ=2.44 (s, 3H, PhCH₃), 2.53 (t, J=5.8 Hz, 4H, 2×CH₂CH₂NTs), 3.38 (t, J=5.8 Hz, 4H, 2×CH₂CH₂NTs), 7.33 (d, J=8.0 Hz, 2H, ArH), 7.67 (d, J=8.0 Hz, 2H, ArH); ESI-MS (m/z): 254.08 (M⁺+H).

Example 2. Synthesis of 1-benzyl-3,5-bis(4-propyl-benzylidene)piperidin-4-one (5d) and Related Compounds (3a-j, 4a-j, 5a-j, 6a-j)

Compound 2c (250 mg, 1.32 mmol) and 4-propylbenzaldehyde (391 mg, 2.64 mmol) were dissolved in 20 mL of EtOH at 0° C. To this reaction mixture 2 mL of 35-38% HCl was added. After 15-20 minutes of stirring at room temperature, the reaction mixture was refluxed for 6 h. The precipitated yellow compound was filtered and washed with EtOH. Crude product was crystallized in EtOH to get compound 5d in pure form. Yield: 368 mg (83%); mp: 113° C.; IR (Film): ν=3026, 2959, 2930, 2871, 1672 (C=O), 1608, 1509, 1454, 1301, 1263, 1195, 1178, 1001, 699; $^1$H NMR (400 MHz, CDCl$_3$): δ=0.94 (t, J=7.3 Hz, 6H, 2×PhCH$_2$CH$_2$CH$_3$), 1.61-1.65 (in, 4H, 2×PhCH$_2$CH$_2$CH$_3$), 2.59 (t, J=8.0 Hz, 4H, 2×PhCH$_2$CH$_2$CH$_3$), 3.70 (s, 2H, NCH$_2$Ph), 3.86 (s, 4H, CH$_2$NCH$_2$), 7.17 (d, J=8.0 Hz, 4H, ArH), 7.22-7.27 (m, 9H, ArH), 7.78 (s, 2H, 2×C=CHPh) ppm; $^{13}$C NMR (100 MHz, CDCl$_3$): δ=13.90 (CH$_3$), 22.29 (CH$_2$), 35.46 (CH$_2$), 54.36 (CH$_2$), 61.24 (CH$_2$), 127.24 (CH), 128.25 (CH), 128.59 (CH), 128.98 (CH), 130.46 (CH), 132.46 (Cquart), 132.60 (Cquart), 136.61 (CH), 144.21 (Cquart), 187.78 (CO) ppm; ESI-MS (m/z): 450.27 (M$^+$+H); Anal. calcd for C$_{32}$H$_{35}$NO: C, 85.48; H, 7.85; N, 3.12; Found: C, 85.46; H, 7.88; N, 3.10.

3,5-Bis(4-bromobenzylidene)-1-tosylpiperidin-4-one (3a)

Yield: 75%; mp: 214° C.; IR (Film): ν=2919, 2850, 1675 (C=O), 1485, 1343, 1160, 1071, 742; $^1$H NMR (400 MHz, CDCl$_3$): δ=2.43 (s, 3H, PhCH$_3$), 4.53 (s, 4H, CH$_2$NCH$_2$), 7.19-7.24 (m, 6H, ArH), 7.48 (d, J=8.2 Hz, 4H, ArH), 7.59-7.63 (m, 4H, ArH, 2×C=CHPh) ppm; ESI-MS (m/z): 585.92 (M$^+$+H); Anal. calcd for C$_{26}$H$_{21}$Br$_2$NO$_3$S: C, 53.17; H, 3.60; N, 2.38; Found: C, 53.15; H, 3.58; N, 2.37.

3,5-Bis(4-etbylbenzylidene)-1-tosylpiperidin-4-one (3b)

Yield: 72%; mp: 165° C.; IR (Film): ν=2964, 2922, 2851, 1675 (C=O), 1605, 1510, 1347, 1266, 1169, 1090, 835, 762, 667; $^1$H NMR (400 MHz, CDCl$_3$): δ=1.27 (t, J=7.3 Hz, 6H, 2×PhCH$_2$CH$_3$), 2.42 (s, 3H, PhCH$_3$), 2.68 (q, J=7.3 Hz, 4H, 2×PhCH$_2$CH$_3$), 4.63 (s, 4H, CH$_2$NCH$_2$), 7.20 (d, J=8.2 Hz, 2H, ArH), 7.26-7.28 (m, 4H, ArH), 7.48 (d, J=8.2 Hz, 4H, ArH), 7.68 (s, 2H, 2×C=CHPh) ppm; ESI-MS (m/z): 486.20 (M$^+$+H); Anal. calcd for C$_{30}$H$_{31}$NO$_3$S: C, 74.20; H, 6.43; N, 2.88; Found: C, 74.22; H, 6.41; N, 2.86.

3,5-Bis(4-propylbenzylidene)-1-tosylpiperidin-4-one (3c)

Yield: 78%; mp: 157° C.; IR (Film): ν=2958, 2924, 1675 (C=O), 1605, 1348, 1263, 1237, 1169, 1089, 994, 966, 866, 665; $^1$H NMR (400 MHz, CDCl$_3$): δ=0.96 (t, J=7.3 Hz, 6H, 2×PhCH$_2$CH$_2$CH$_3$), 1.68-1.70 (m, 4H, 2×PhCH$_2$CH$_2$CH$_3$), 2.42 (s, 3H, PhCH$_3$), 2.62 (t, J=7.8 Hz, 4H, 2×PhCH$_2$CH$_2$CH$_3$), 4.63 (s, 4H, CH$_2$NCH$_2$), 7.20 (d, J=8.2 Hz, 4H, ArH), 7.26-7.27 (m, 4H, ArH), 7.48 (d, J=8.2 Hz, 4H, ArH), 7.67 (s, 2H, 2×C=CHPh) ppm; $^{13}$C NMR (100 MHz, CDCl$_3$): δ=13.85, 21.58, 24.28, 37.91, 47.30, 127.60, 129.01, 129.14, 129.64, 130.48, 131.86, 138.53, 184.94 ppm; ESI-MS (m/z): 514.23 (M$^+$+H); Anal. calcd for C$_{32}$H$_{35}$NO$_3$S: C, 74.82; H, 6.87; N, 2.73; Found: C, 74.81; H, 6.85; N, 2.75.

3,5-Bis(4-methylbenzylidene)-1-tosylpiperidin-4-one (3d)

Yield: 81%; mp: 187° C.; IR (Film): ν=2919, 2851, 1678 (C=O), 1606, 1511, 1348, 1265, 1178, 1168, 992, 815, 667; $^1$H NMR (400 MHz, CDCl$_3$): δ=2.42 (s, 9H, 3×CH$_3$), 4.62 (s, 4H, CH$_2$NCH$_2$), 7.20 (d, J=8.2 Hz, 4H, ArH), 7.23-7.26 (m, 4H, ArH), 7.46 (d, J=8.2 Hz, 4H, ArH), 7.66 (s, 2H, 2×C=CHPh) ppm; $^{13}$C NMR (100 MHz, CDCl$_3$): δ=21.57, 47.27, 127.56, 129.19, 129.62, 130.45, 131.62, 138.52, 140.14, 143.95, 184.99 ppm; ESI-MS (m/z): 458.17 (M$^+$+H); Anal. calcd. for C$_{28}$H$_{27}$NO$_3$S: C, 73.49; H, 5.95; N, 3.06; Found: C, 73.52; H, 5.97; N, 3.02.

3,5-Bis(4-chlorobenzylidene)-1-tosylpiperidin-4-one (3e)

Yield: 80%; mp: 209° C.; IR (Film): ν=2919, 2850, 1607, 1483, 1343, 1160, 1087, 947, 829, 792, 742, 677; $^1$H NMR (400 MHz, CDCl$_3$): δ=2.43 (s, 3H, PhCH$_3$), 4.55 (s, 4H, CH$_2$NCH$_2$), 7.23 (d, J=7.8 Hz, 4H, ArH), 7.26-7.28 (m, 2H, ArH), 7.42 (d, J=7.8 Hz, 4H, ArH), 7.48 (d, J=7.8 Hz, 2H, ArH), 7.65 (s, 2H, 2×C=CHPh) ppm; ESI-MS (m/z): 498.06 (M$^+$+H); 500.12 (M$^+$+2), 502.12 (M$^+$+4); Anal. calcd. for C$_{26}$H$_{21}$Cl$_2$NO$_3$S: C, 62.65; H, 4.25; N, 2.81; Found: C, 62.63; H, 4.26; N, 2.80.

3,5-Bis(4-methoxybenzylidene)-1-tosylpiperidin-4-one (3f)

Yield: 68%; mp: 183° C.; IR (Film): ν=2933, 2838, 1671 (C=O), 1598, 1510, 1459, 1349, 1257, 1171, 1030, 965, 830, 669; $^1$H NMR (400 MHz, CDCl$_3$): δ=2.41 (s, 3H, PhCH$_3$), 3.88 (s, 6H, 2×PhOCH$_3$), 4.62 (s, 4H, CH$_2$NCH$_2$), 6.97 (d, J=8.2 Hz, 4H, ArH), 7.20 (d, J=8.2 Hz, 2H, ArH), 7.31 (d, J=8.2 Hz, 4H, ArH), 7.48 (d, J=8.2 Hz, 2H, ArH), 7.64 (s, 2H, 2×C=CHPh) ppm; $^{13}$C NMR (100 MHz, CDCl$_3$): δ=21.58, 47.24, 55.41, 114, 127.56, 128.01, 129.63, 132.37, 134.77, 138.07, 143.92, 160.75, 184.89 ppm; ESI-MS (m/z): 490.16 (M$^+$+H); Anal. calcd for C$_{28}$H$_{27}$NO$_5$S: C, 68.69; H, 5.56; N, 2.86; Found: C, 68.68; H, 5.58; N, 2.88.

3,5-Bis(4-tert-butylbenzylidene)-1-tosylpiperidin-4-one (3g)

Yield: 78%; mp: 220° C.; IR (Film): ν=2962, 2870, 1672 (C=O), 1612, 1581, 1413, 1346, 1262, 1184, 1162, 1037, 962, 846, 758, 682, 673; $^1$H NMR (400 MHz, CDCl$_3$): δ=1.31 (s, 18H, 2×PhC(CH$_3$)$_3$), 2.37 (s, 3H, PhCH$_3$), 4.58 (s, 4H, CH$_2$NCH$_2$), 7.17-7.21 (m, 2H, ArH), 7.24-7.26 (m, 4H, ArH), 7.41-7.46 (m, 6H, ArH), 7.64 (s, 2H, 2×C=CHPh) ppm; $^{13}$C NMR (100 MHz, CDCl$_3$): δ=21.59, 31.12, 34.89, 47.36, 125.87, 127.62, 129.64, 130.35, 131.58, 134.60, 143.98, 153.16, 184.68 ppm; ESI-MS (m/z): 542.27 (M$^+$+H); Anal. calcd for C$_{34}$H$_{39}$NO$_3$S: C, 75.38; H, 7.26; N, 2.59; Found: C, 75.39; H, 7.28; N, 2.57.

3,5-Bis(4-butylbenzylidene)-1-tosylpiperidin-4-one (3h)

Yield: 85%; mp: 148° C.; IR (Film): ν=2957, 2928, 2871, 2859, 1676 (C=O), 1604, 1510, 1350, 1265, 1241, 1181, 1169, 997, 869, 821, 666; $^1$H NMR (400 MHz, CDCl$_3$): δ=0.94 (t, J=7.3 Hz, 6H, 2×PhCH$_2$CH$_2$CH$_2$CH$_3$), 1.36-1.40 (m, 4H, 2×PhCH$_2$CH$_2$CH$_2$CH$_3$), 1.59-1.64 (m, 4H, 2×PhCH$_2$CH$_2$CH$_2$CH$_3$), 2.42 (s, 3H, PhCH$_3$), 2.65 (t, J=8.2 Hz, 4H, 2×PhCH$_2$CH$_2$CH$_2$CH$_3$), 4.63 (s, 4H, CH$_2$NCH$_2$), 7.21 (d, J=8.2 Hz, 2H, ArH), 7.26-7.27 (m, 6H, ArH), 7.48 (d, J=8.2 Hz, 4H, ArH), 7.67 (s, 2H, 2×C=CHPh) ppm; $^{13}$C NMR (100 MHz, CDCl$_3$): δ=13.92, 21.57, 22.35, 33.30, 35.55, 47.30, 127.59, 128.96, 129.12, 129.64, 130.49, 131.81, 138.54, 145.12, 184.94 ppm; ESI-MS (m/z): 542.27

(M⁺+H); Anal. calcd for C₃₄H₃₉NO₃S: C, 75.38; H, 7.26; N, 2.59; Found: C, 75.36; H, 7.23; N, 2.57.

3,5-Bis(4-isopropylbenzylidene)-1-tosylpiperidin-4-one (3i)

Yield: 71%; mp: 177° C.; IR (Film): ν=2951, 2927, 2861, 2859, 1675 (C=O), 1614, 1510, 1450, 1265, 1241, 1182, 1169, 997; ¹H NMR (400 MHz, CDCl₃): δ=1.29 (d, J=6.8 Hz, 12H, 2×PhCH(CH₃)₂), 2.42 (s, 3H, PhCH₃), 2.91-3.01 (m, 2H, 2×PhCH(CH₃)₂), 4.63 (s, 4H, CH₂NCH₂), 7.22 (d, J=8.2 Hz, 4H, ArH), 7.28-7.33 (m, 6H, ArH), 7.49 (d, J=8.2 Hz, 2H, ArH), 7.68 (s, 2H, 2×C=CHPh) ppm; ¹³C NMR (100 MHz, CDCl₃): δ=21.58, 23.73, 34.06, 47.34, 27.00, 127.60, 129.14, 129.64, 130.60, 131.97, 138.53, 150.92, 184.91 ppm; ESI-MS (m/z): 514.23 (M⁺+H); Anal. calcd for C₃₂H₃₅NO₃S: C, 74.82; H, 6.87; N, 2.73; Found: C, 74.84; H, 6.86; N, 2.75.

3,5-Bis(4-fluorobenzylidene)-1-tosylpiperidin-4-one (3j)

Yield: 73%; mp: 204° C.; IR (Film): ν=3023, 1669 (C=O), 1599, 1573, 1505, 1342, 1223, 1154, 1086, 1041, 946, 835, 745, 677; ¹H NMR (400 MHz, CDCl₃): δ=2.43 (s, 3H, PhCH₃), 4.51 (s, 4H, CH₂NCH₂), 7.13-7.18 (m, 4H, ArH), 7.23 (d, J=7.8 Hz, 2H, ArH), 7.32-7.36 (m, 2H, ArH), 7.49-7.51 (m, 4H, ArH), 7.67 (s, 2H, 2×C=CHPh) ppm; ESI-MS (m/z): 466.12 (M⁺+H); Anal. calcd for C₂₆H₂₁F₂NO₃S: C, 67.08; H, 4.55; N, 3.01; Found: C, 67.37; H, 4.70; N, 3.02.

3,5-Bis(4-methylbenzylidene)-1-(phenylsulfonyl)piperidin-4-one (4a)

Yield: 67%; mp: 211° C.; IR (Film): ν=2920, 2850, 1605, 1463, 1349, 1263, 1171, 1091, 994, 814; ¹H NMR (400 MHz, CDCl₃): δ=2.42 (s, 6H, 2×PhCH₃), 4.67 (s, 4H, CH₂NCH₂), 7.24-7.29 (m, 8H, ArH), 7.40-7.43 (m, 2H, ArH), 7.55-7.58 (m, 3H, ArH), 7.65 (s, 2H, 2×C=CHPh) ppm; ¹³C NMR (100 MHz, CDCl₃): δ=21.48, 47.27, 127.48, 129.00, 129.03, 129.64, 130.46, 138.62, 184.82 ppm; ESI-MS (m/z): 444.16 (M⁺+H); Anal. calcd for C₂₇H₂₅NO₃S: C, 73.11; H, 5.68; N, 3.16; Found: C, 73.05; H, 5.86; N, 3.10.

3,5-Bis(4-ethylbenzylidene)-1-(phenylsulfonyl)piperidin-4-one (4b)

Yield: 77%; mp: 165° C.; IR (Film): ν=2965, 2922, 2851, 1678 (C=O), 1604, 1584, 1350, 1262, 1172, 1155, 972, 867, 838, 829, 760; ¹H NMR (400 MHz, CDCl₃): δ=1.27 (t, J=7.3 Hz, 6H, 2×PhCH₂CH₃), 2.69 (q, J=7.7 Hz, 4H, 2×PhCH₂CH₃), 4.68 (s, 4H, CH₂NCH₂), 7.26-7.31 (m, 8H, ArH), 7.40-7.44 (m, 2H, ArH), 7.55-7.59 (m, 3H, ArH), 7.65 (s, 2H, 2×C=CHPh) ppm; ¹³C NMR (100 MHz, CDCl₃): δ=15.23, 28.78, 47.31, 127.51, 128.44, 129.01, 130.57, 131.79, 133.11, 138.66, 146.42, 184.79 ppm; ESI-MS (m/z): 472.19 (M⁺+H); Anal. calcd for C₂₉H₂₉NO₃S: C, 73.86; H, 6.20; N, 2.97; Found: C, 73.93; H, 6.38; N, 2.92.

3,5-Bis(4-isopropylbenzylidene)-1-(phenylsulfonyl)piperidin-4-one (4c)

Yield: 72%; mp: 170° C.; IR (Film): ν=2959, 2921, 2851, 1668 (CO), 1606, 1463, 1347, 1265, 1241, 1166, 1090, 956, 835, 740; ¹H NMR (400 MHz, CDCl₃): δ=1.29 (d, J=6.8 Hz, 12H, 2×PhCH(CH₃)₂), 2.95-2.97 (m, 2H, 2×PhCH(CH₃)₂), 4.68 (s, 4H, CH₂NCH₂), 7.27-7.34 (m, 8H, ArH), 7.41-7.44 (m, 2H, ArH), 7.55-7.61 (m, 3H, ArH), 7.66 (s, 2H, 2×C=CHPh) ppm; ¹³C NMR (100 MHz, CDCl₃): δ=23.73, 34.07, 47.35, 127.03, 127.54, 129.01, 130.61, 131.92, 133.12, 137.88, 150.97, 184.74 ppm; ESI-MS (m/z): 500.22 (M⁺+H); Anal. calcd for C₃₁H₃₃NO₃S: C, 74.52; H, 6.66; N, 2.80; Found: C, 74.55; H, 6.63; N, 2.82.

1-(Phenylsulfonyl)-3,5-bis(4-propylbenzylidene)piperidin-4-one (4d)

Yield: 69%; mp: 153° C.; IR (Film): ν=2952, 1704 (C=O), 1505, 1443, 1232, 1035, 10313, 808, 757; ¹H NMR (400 MHz, CDCl₃): δ=0.94 (t, J=7.3 Hz, 6H, 2×PhCH₂CH₂CH₃), 1.64-1.68 (m, 4H, 2×PhCH₂CH₂CH₃), 2.60 (t, J=7.6 Hz, 4H, 2×PhCH₂CH₂CH₃), 4.65 (s, 4H, CH₂NCH₂), 7.24-7.25 (n, 3H, ArH), 7.37-7.41 (m, 3H, ArH), 7.52-7.58 (m, 7H, ArH), 7.63 (s, 2H, 2×C=CHPh) ppm; ¹³C NMR (100 MHz, CDCl₃): δ=13.85, 24.28, 37.91, 47.30, 127.51, 128.98, 129.03, 130.50, 131.12, 138.67, 144.97, 184.82 ppm; ESI-MS (m/z): 501.22 (M⁺+H); Anal. calcd for C₃₁H₃₃NO₃S: C, 74.52; H, 6.66; N, 2.80; Found: C, 73.30; H, 6.21; N, 2.79.

3,5-Bis(4-chlorobenzylidene)-1-(phenylsulfonyl)piperidin-4-one (4e)

Yield: 74%; mp: 237° C.; IR (Film): ν=2920, 2851, 1610, 1490, 1166, 1092, 809; ¹H NMR (400 MHz, CDCl₃): δ=4.60 (s, 4H, CH₂NCH₂), 7.26-7.29 (m, 5H, ArH), 7.43-7.46 (m, 6H, ArH), 7.58-7.61 (m, 2H, ArH), 7.64 (s, 2H, 2×C=CHPh) ppm; ESI-MS (m/z): 484.05 (M⁺+H), 486.12 (M⁺+2), 488.08 (M⁺+4); Anal. calcd for C₂₅H₁₉Cl₂NO₃S: C, 61.99; H, 3.95; N, 2.89; Found: C, 60.77; H, 4.02; N, 2.71.

3,5-Bis(4-tert-butylbenzylidene)-1-(phenylsulfonyl)piperidin-4-one (4f)

Yield: 68%; mp: 194° C.; IR (Film): ν=2963, 2869, 1672 (C=O), 1608, 1583, 1352, 1264, 1185, 1166, 990, 756, 724; ¹H NMR (400 MHz, CDCl₃): δ=1.37 (s, 18H, 2×PhC(CH₃)₃), 4.69 (s, 4H, CH₂NCH₂), 7.29 (d, J=8.2 Hz, 4H, ArH), 7.41-7.49 (m, 6H, ArH), 7.56-7.62 (m, 3H, ArH), 7.67 (s, 2H, 2×C=CHPh) ppm; ¹³C NMR (100 MHz, CDCl₃): δ=31.13, 34.92, 47.37, 125.91, 127.56, 129.03, 130.38, 131.53, 133.13, 138.56, 153.24, 148.23 ppm; ESI-MS (m/z): 529.25 (M⁺+H); Anal. calcd for C₃₃H₃₇NO₃S: C, 75.11; H, 7.07; N, 2.65; Found: C, 75.13; H, 7.02; N, 2.61.

3,5-Bis(4-butylbenzylidene)-1-(phenylsulfonyl)piperidin-4-one (4g)

Yield: 76%; mp: 134° C.; IR (Film): ν=2956, 2930, 2858, 1676 (C=O), 1605, 1446, 1352, 1265, 1168, 1090, 691; ¹H NMR (400 MHz, CDCl₃): δ=0.94 (t, J=7.0 Hz, 6H, 2×PhCH₂CH₂CH₂CH₃), 1.35-1.42 (m, 4H, 2×PhCH₂CH₂CH₂CH₃), 1.59-1.64 (m, 4H, 2×PhCH₂CH₂CH₂CH₃), 2.65 (t, J=7.8 Hz, 4H, 2×PhCH₂CH₂CH₂CH₃), 4.68 (s, 4H, CH₂NCH₂), 7.26-7.27 (m, 4H, ArH), 7.42-7.44 (m, 4H, ArH), 7.55-7.60 (m, 5H, ArH), 7.66 (s, 2H, 2×C=CHPh) ppm; ESI-MS (m/z): 528.25 (M⁺+H); Anal. calcd for C₃₃H₃₇NO₃S: C, 75.11; H, 7.07; N, 2.65; Found: C, 75.12; H, 7.11; N, 2.66.

3,5-Bis(4-methoxybenzylidene)-1-(phenylsulfonyl)piperidin-4-one (4h)

Yield: 71%; mp: 217° C.; IR (Film): ν=2918, 2850, 1670 (C=O), 1595, 1506, 1460, 1349, 1252, 1234, 1169, 1028, 991, 837; $^1$H NMR (400 MHz, CDCl$_3$): δ=3.88 (s, 6H, 2×PhOCH$_3$), 4.67 (s, 4H, CH$_2$NCH$_2$), 6.97 (d, J=8.6 Hz, 4H, ArH), 7.31 (d, J=8.6 Hz, 4H, ArCH), 7.41-7.43 (m, 2H, ArH), 7.54-7.63 (m, 5H, ArH, 2×C=CHPh) ppm; $^{13}$C NMR (100 MHz, CDCl$_3$): δ=47.25, 55.42, 114.42, 127.08, 127.48, 127.83, 128.99, 132.40, 138.18, 160.78, 184.74 ppm; ESI-MS (m/z): 476.15 (M$^+$+H); Anal. calcd for C$_{27}$H$_{25}$NO$_5$S: C, 68.19; H, 5.30; N, 2.95; Found: C, 68.17; H, 5.36; N, 2.99.

3,5-Bis(4-bromobenzylidene)-1-(phenylsulfonyl)piperidin-4-one (4i)

Yield: 77%; mp: 247° C.; IR (Film): ν=2920, 2850, 1674 (C=O), 1219, 1071, 822, 772; $^1$H NMR (400 MHz, CDCl$_3$): δ=4.59 (s, 4H, CH$_2$NCH$_2$), 7.19 (d, J=8.2 Hz, 2H, ArH), 7.42-7.46 (m, 4H, ArH), 7.58-7.62 (m, 9H, ArH, 2×C=CHPh) ppm; ESI-MS (m/z): 571.95 (M$^+$+H); Anal. calcd for C$_{25}$H$_{19}$Br$_2$NO$_3$S: C, 52.38; H, 3.34; N, 2.44; Found: C, 52.57; H, 3.14; N, 2.46.

3,5-Bis(4-fluorobenzylidene)-1-(phenylsulfonyl)piperidin-4-one (4j)

Yield: 73%; mp: 181° C.; IR (Film): ν=2922, 2851, 1670 (C=O), 1600, 1507, 1345, 1227, 1158, 1088, 948, 835, 751; $^1$H NMR (400 MHz, CDCl$_3$): δ=4.62 (s, 4H, CH$_2$NCH$_2$), 7.15-7.19 (m, 4H, ArH), 7.32-7.36 (m, 4H, ArH), 7.44-7.46 (m, 2H, ArH), 7.59-7.61 (m, 3H, ArH), 7.65 (s, 2H, 2×C=CHPh) ppm; ESI-MS (m/z): 452.11 (M$^+$+H); Anal. calcd for C$_{25}$H$_{19}$F$_2$NO$_3$S: C, 66.51; H, 4.24; N, 3.10; Found: C, 66.68; H, 4.42; N, 3.03.

1-Benzyl-3,5-bis(4-methylbenzylidene)piperidin-4-one (5a)

Yield: 78%; mp: 170° C.; IR (Film ν=2920, 2801, 1609, 1510, 1451, 1264, 1178, 1000, 816; $^1$H NMR (400 MHz, CDCl$_3$): δ=2.36 (s, 6H, 2×PhCH$_3$), 3.71 (s, 2H, NCH$_2$Ph), 3.87 (s, 4H, CH$_2$NCH$_2$), 7.16-7.24 (m, 13H, ArH), 7.78 (s, 2H, 2×C=CHPh) ppm; $^{13}$C NMR (100 MHz, CDCl$_3$): δ=21.39, 54.46, 61.43, 128.30, 128.96, 129.25, 130.45, 132.43, 136.47, 187.79 ppm; ESI-MS (m/z): 394.21 (M$^+$+H); Anal. calcd for C$_{28}$H$_{27}$NO: C, 85.46; H, 6.92; N, 3.56; Found: C, 85.39; H, 6.95; N, 3.58.

1-Benzyl-3,5-bis(4-bromobenzylidene)piperidin-4-one (5b)

Yield: 69%; mp: 151° C.; IR (Film): ν=3028, 2924, 2807, 2739, 1669 (C=O), 1610, 1579, 1487, 1402, 1315, 1266, 1189, 1071, 1003, 819, 755; $^1$H NMR (400 MHz, CDCl$_3$): δ=3.69 (s, 2H, NCH$_2$Ph), 3.80 (s, 4H, CH$_2$NCH$_2$), 7.15-7.25 (m, 9H, ArH), 7.47 (d, J=8.0 Hz, 4H, ArH), 7.71 (s, 2H, 2×C=CHPh) ppm; ESI-MS (m/z): 522 (M$^+$+H); Anal. calcd for C$_{26}$H$_{21}$Br$_2$NO: C, 59.68; H, 4.05; N, 2.68; Found: C, 59.65; H, 4.07; N, 2.66.

1-Benzyl-3,5-bis-(4-ethyl-benzylidene)-piperidin-4-one (5c)

Yield: 68%; mp: 119° C.; IR (Film): ν=3028, 2964, 2873, 2746, 1668 (C=O), 1606, 1581, 1450, 1320, 1266, 1178, 1166, 1073, 932, 830, 752; $^1$H NMR (400 MHz, CDCl$_3$): δ=1.22 (t, J=7.3 Hz, 6H, 2×PhCH$_2$CH$_3$), 2.62 CH$_2$NCH$_2$), 7.19-7.26 (m, 13H, ArH), 7.78 (s, 2H, 2×C=CHPh) ppm; $^{13}$C NMR (100 MHz, CDCl$_3$): δ=15.25, 28.65, 54.39, 61.32, 128.00, 128.22, 128.90, 130.50, 132.52, 132.61, 136.43, 145.42, 187.74 ppm; ESI-MS (m/z): 423.24 (M$^+$+2H); Anal. calcd for C$_{30}$H$_{31}$NO: C, 85.47; H, 7.41; N, 3.32; Found: C, 85.44; H, 7.43; N, 3.35.

1-Benzyl-3,5-bis(4-isopropylbenzylidene)piperidin-4-one (5e)

Yield: 76%; mp: 157° C.; IR (Film): ν=2960, 2870, 1672 (C=O), 1612, 1508, 1455, 1419, 1311, 1264, 1180, 1001, 830; $^1$H NMR (400 MHz, CDCl$_3$): δ=1.21 (d, J=7.3 Hz, 12H, 2×PhCH(CH$_3$)$_2$), 2.89 (sept, 2H, 2×PhCH(CH$_3$)$_2$), 3.73 (s, 2H, NCH$_2$Ph), 3.91 (s, 4H, CH$_2$NCH$_2$), 7.18-7.28 (m, 13H, ArH), 7.81 (s, 2H, 2×C=CHPh) ppm; $^{13}$C NMR (100 MHz, CDCl$_3$): δ=23.76, 33.98, 54.42, 61.31, 126.63, 127.24, 128.27, 130.58, 132.84, 136.48, 150.06, 187.87 ppm; ESI-MS (m/z): 450.27 (M$^+$+H); Anal. calcd for C$_{32}$H$_{35}$NO: C, 85.48; H, 7.85; N, 3.12; Found: C, 85.42; H, 7.84; N, 3.08.

1-Benzyl-3,5-bis(4-butylbenzylidene)piperidin-4-one (5f)

Yield: 75%; mp: 104° C.; IR (Film): ν=2956, 2929, 2858, 1673 (C=O), 1613, 1509, 1455, 1418, 1305, 1264, 1195, 1177, 1001, 931, 829, 753; $^1$H NMR (400 MHz, CDCl$_3$): δ=0.90 (t, J=7.3 Hz, 6H, 2×PhCH$_2$CH$_2$CH$_2$CH$_3$), 1.30-1.39 (m, 4H, 2×PhCH$_2$CH$_2$CH$_2$CH$_3$), 1.55-1.63 (m, 4H, 2×PhCH$_2$CH$_2$CH$_2$CH$_3$), 2.59 (t, J=7.3 Hz, 4H, 2×PhCH$_2$CH$_2$CH$_2$CH$_3$), 3.71 (s, 2H, NCH$_2$Ph), 3.88 (s, 4H, CH$_2$NCH$_2$), 7.16 (d, J=8.0 Hz, 4H, ArH). 7.22-7.26 (m, 9H, ArH), 7.79 (s, 2H, 2×C=CHPh) ppm; $^{13}$C NMR (100 MHz, CDCl$_3$): δ=13.90, 22.29, 33.34, 35.46, 54.36, 61.24, 128.25, 128.59, 128.88, 130.46, 132.60, 136.61, 144.21, 187.78 ppm; ESI-MS (m/z): 478.30 (M$^+$+H); Anal. calcd for C$_{34}$H$_{39}$NO: C, 85.49; H, 8.23; N, 2.93; Found: C, 85.55; H, 8.21; N, 2.94.

1-Benzyl-3,5-bis(4-tert-butylbenzylidene)piperidin-4-one (5g)

Yield: 77%; mp: 167° C.; IR (Film): ν=2963, 2869, 1672 (C=O), 1611, 1582, 1264, 1203, 1185, 1017, 1003, 830, 737; $^1$H NMR (400 MHz, CDCl$_3$): δ=1.32 (s, 18H, 2×PhC(CH$_3$)$_3$), 3.71 (s, 2H, NCH$_2$Ph), 3.87 (s, 4H, CH$_2$NCH$_2$), 7.19-7.25 (m, 5H, ArH), 7.28 (d, J=8.2 Hz, 4H, ArH), 7.38 (d, J=8.2 Hz, 4H, ArH), 7.77 (s, 2H, 2×C=CHPh) ppm; $^{13}$C NMR (100 MHz, CDCl$_3$): δ=31.13, 34.78, 54.41, 61.30, 125.49, 128.27, 128.99, 130.33, 132.70, 136.38, 152.30, 187.92 ppm; ESI-MS (m/z): 478.30 (M$^+$+H); Anal. calcd for C$_{34}$H$_{39}$NO: C, 85.49; H, 8.23; N, 2.93; Found: C, 85.51; H, 8.23; N, 2.97.

1-Benzyl-3,5-bis(4-methoxybenzylidene)piperidin-4-one (5h)

Yield: 70%; mp: 160° C. (lit. mp 150-154° C.); IR (Film): ν=2968, 2838, 2745, 1670 (C=O), 1600, 1577, 1510, 1303, 1256, 1172, 1030, 830; $^1$H NMR (400 MHz, CDCl$_3$): δ=3.72 (s, 2H, NCH$_2$Ph), 3.82 (s, 4H, CH$_2$NCH$_2$), 3.87 (s, 6H, 2×PhOCH$_3$), 6.88 (d, J=8.0 Hz, 4H, ArH), 7.18-7.31 (m, 9H, ArH), 7.77 (s, 2H, 2×C=CHPh) ppm; ESI-MS (m/z): 426.20 (M$^+$+H); Anal. calcd for C$_{28}$H$_{27}$NO$_3$: C, 79.03; H, 6.40; N, 3.29; Found: C, 79.08; H, 6.42; N, 3.24.

1-Benzyl-3,5-bis(4-chlorobenzylidene)piperidin-4-one (5i)

Yield: 73%; mp: 164° C.; IR (Film): ν=2926, 2810, 2738, 1670 (C=O), 1612, 1580, 1490, 1267, 1190, 1094, 1004, 820.32, 756.02; $^1$H NMR (400 MHz, CDCl$_3$): δ=3.70 (s, 2H, NCH$_2$Ph), 3.80 (s, 4H, CH$_2$NCH$_2$), 7.24-7.25 (m, 9H, ArH), 7.33 (d, J=8.2 Hz, 4H, ArH), 7.72 (s, 2H, 2×C=CHPh) ppm; $^{13}$C NMR (100 MHz, CDCl$_3$): δ=54.19, 61.54, 128.39, 128.80, 128.90, 131.49, 135.31, 187.36 ppm; ESI-MS (m/z): 434.10 (M$^+$+H), 436.18 (M$^+$+2), 438.10 (M$^+$+4); Anal. calcd C$_{26}$H$_{21}$Cl$_2$NO: C, 71.89; H, 4.87; N, 3.22; for; Found: C, 71.90; H, 4.88; N, 3.20.

1-Benzyl-3,5-bis(4-fluorobenzylidene)piperidin-4-one (5j)

Yield: 77%; mp: 159° C.; IR (Film): ν=2810, 1670 (C=O), 1618, 1581, 1508, 1455, 1238, 1191, 1005, 832, 791; $^1$H NMR (400 MHz, CDCl$_3$): δ=3.67 (s, 2H, NCH$_2$Ph), 3.80 (s, 4H, CH$_2$NCH$_2$), 7.16-7.24 (m, 9H, ArH), 7.27 (d, J=8.8 Hz, 4H, ArH), 7.71 (s, 2H, 2×C'CHPh) ppm; ESI-MS (m/z): 402.16 (M$^+$+H); Anal. calcd for C$_{26}$H$_{21}$F$_2$NO: C, 77.79; H, 5.27; N, 3.49; Found: C, 76.85; H, 5.33; N, 3.47.

3,5-Bis-(4-bromo-benzylidene)-1-ethyl-piperidin-4-one (6a)

Yield: 64%; mp: 178° C.; IR (Film): ν=3402, 2115, 1646 (C=O), 1466, 1112, 1032, 1014, 747; $^1$H NMR (400 MHz, CDCl$_3$): δ=1.04 (t, J=7.3 Hz, 3, CH$_2$CH$_3$), 2.64 (q, J=7.3 Hz, 2H, CH$_2$CH$_3$), 3.79-3.92 (m, 4H, CH$_2$NCH$_2$), 7.22 (d, J=7.8 Hz, 4H, ArH), 7.52-7.56 (m, 4H, ArH), 7.80 (s, 2H, 2×C=CHPh) ppm; ESI-MS (m/z): 459.98 (M$^+$+H), 461.42 (M$^+$+2), 463.12 (M$^+$+4); Anal. calcd for C$_{21}$H$_{19}$Br$_2$NO: C, 54.69; H, 4.15; N, 3.04; Found: C, 53.81; H, 4.20; N, 3.03.

3,5-Bis(4-cblorobenzylidene)-1-ethylpiperidin-4-one (6b)

Yield: 68%; mp: 163° C.; IR (Film): ν=2973, 2752, 1614, 1588, 1490, 1408, 1310, 1261, 1173, 1095, 987, 824; $^1$H NMR (400 MHz, CDCl$_3$): δ=1.04 (t, J=7.3 Hz, 3H, CH$_2$CH$_3$), 2.63 (q, J=7.3 Hz, 2H, CH$_2$CH$_3$), 3.85 (s, 4H, CH$_2$NCH$_2$), 7.30 (d, J=8.2 Hz, 4H, ArH), 7.38 (d, J=8.2 Hz, 4H, ArH), 7.78 (s, 2H, 2×C=CHPh) ppm; ESI-MS (m/z): 372.08 (M$^+$+H), 374.46 (M$^+$+2), 346.22 (M$^+$+4); Anal. calcd for C$_{21}$H$_{19}$Cl$_2$NO: C, 67.75; H, 5.14; N, 3.76; Found: C, 67.77; H, 5.17; N, 3.77.

1-Ethyl-3,5-bis(4-fluorobenzylidene)piperidin-4-one (6c)

Yield: 79%; mp 114° C.; IR (Film): ν=2968, 2748, 1676 (C=O), 1617, 1600, 1508, 1413, 1225, 1157, 835; $^1$H NMR (400 MHz, CDCl$_3$): δ=1.01 (t, J=7.5 Hz, 3H, CH$_2$CH$_3$), 2.62 (q, J=7.5 Hz, 2H, CH$_2$CH$_3$), 3.85 (s, 4H, CH$_2$NCH$_2$), 7.05-7.07 (m, 4H, ArH), 7.31-7.34 (m, 4H, ArH), 7.78 (s, 2H, 2×C=CHPh) ppm; ESI-MS (m/z): 340.14 (M$^+$+H); Anal. calcd for C$_{21}$H$_{19}$F$_2$NO: C, 74.32; H, 5.64; N, 4.13; Found: C, 74.32; H, 5.64; N, 4.13.

1-Ethyl-3,5-bis(4-methylbenzylidene)piperidin-4-one (6d)

Yield: 71%; mp: 142° C.; IR (Film): ν=3026, 2983, 2818, 2748, 1670 (C=O), 1604, 1580, 1510, 1260, 1167, 987, 814; $^1$H NMR (400 MHz, CDCl$_3$): δ=1.04 (t, J=7.4 Hz, 3H, CH$_2$CH$_3$), 2.38 (s, 6H, 2×PhCH$_3$), 2.60 (q, J=7.4 Hz, 2H, CH$_2$CH$_3$), 3.86 (s, 4H, CH$_2$NCH$_2$), 7.21 (d, J=8.0 Hz, 4H, ArH), 7.29 (d, J=8.0 Hz, 4H, ArH), 7.81 (s, 2H, 2×C=CHPh) ppm; $^{13}$C NMR (100 MHz, CDCl$_3$): δ=12.35, 21.42, 51.10, 54.29, 129.31, 130.48, 132.43, 136.76, 139.32, 187.36 ppm; ESI-MS (m/z): 332.19 (M$^+$+H); Anal. calcd for C$_{23}$H$_{25}$NO: C, 83.34; H, 7.60; N, 4.23 Found: C, 83.31; H, 7.58; N, 4.25.

1-Ethyl-3,5-bis(4-ethylbenzylidene)piperidin-4-one (6e)

Yield: 20%; mp: 178° C.; IR (Film): ν=3395, 2908, 1593, 1494, 1416, 1310, 1174, 1085, 1006, 910, 834, 747; $^1$H NMR (400 MHz, CDCl$_3$): δ=1.04 (t, J=7.3 Hz, 3H, CH$_2$CH$_3$), 1.23 (t, J=7.3 Hz, 6H, 2×PhCH$_2$CH$_3$), 2.60-2.68 (m, 6H, CH$_2$CH$_3$, 2×PhCH$_2$CH$_3$), 3.82 (s, 4H, CH$_2$NCH$_2$), 7.23 (d, J=8.0 Hz, 4H, ArH), 7.32 (d, J=8.0 Hz, 4H, ArH), 7.79 (s, 2H, 2×C=CHPh) ppm; $^{13}$C NMR (100 MHz, CDCl$_3$): δ=12.38, 15.24, 28.68, 51.22, 54.41, 128.05, 130.55, 132.48, 132.71, 136.46, 145.46, 187.39 ppm; ESI-MS (m/z): 360.22 (M$^+$+H); Anal. calcd for C$_{25}$H$_{29}$NO: C, 83.52; H, 8.13; N, 3.90; Found: C, 83.51; H, 8.10; N, 3.94.

1-Ethyl-3,5-bis(4-propylbenzylidene)piperidin-4-one (6f)

Yield: 67%; Yellow liquid; IR (Film): ν=2960, 2931, 1656 (C=O), 1606, 1585, 1510, 1308, 1279, 1174, 989, 801; $^1$H NMR (400 MHz, CDCl$_3$): δ=0.89-0.95 (m, 9H, CH$_2$CH$_3$, 2×PhCH$_2$CH$_2$CH$_3$), 1.54-1.66 (m, 4H, 2×PhCH$_2$CH$_2$CH$_3$), 2.55-2.65 (m, 6H, CH$_2$CH$_3$, 2×PhCH$_2$CH$_2$CH$_3$), 3.88 (s, 4H, CH$_2$NCH$_2$), 7.14 (d, J=8.2 Hz, 4H, ArH), 7.30 (d, J=8.2 Hz, 4H, ArH), 7.77 (s, 2H, 2×C=CHPh) ppm; $^{13}$C NMR (100 MHz, CDCl$_3$): δ=13.70, 13.78, 16.03, 24.10, 24.46, 37.70, 38.10, 51.56, 52.78, 54.44, 128.32, 128.67, 129.09, 129.85, 130.48, 132.48, 136.48, 191.97 ppm; ESI-MS (m/z): 388.26 (M$^+$+H); Anal. calcd for C$_{27}$H$_{33}$NO: C, 83.68; H, 8.58; N, 3.61; Found: C, 83.70; H, 8.55; N, 3.63.

1-Ethyl-3,5-bis(4-isopropylbenzylidene)piperidin-4-one (6g)

Yield: 63%; Yellow liquid; IR (Film): ν=2908, 1658 (C=O), 1593, 1494, 1416, 1310, 1174, 1085, 1006, 910, 834, 747; $^1$H NMR (400 MHz, CDCl$_3$): δ=1.20-1.29 (m, 15H, CH$_2$CH$_3$, 2×PhCH(CH$_3$)$_2$), 2.88-292 (m, 4H, CH$_2$CH$_3$, 2×PhCH(CH$_3$)$_2$), 3.97 (s, 4H, CH$_2$NCH$_2$), 7.22-7.26 (m, 8H, ArH), 7.78 (s, 2H, C=CHPh) ppm; ESI-MS (m/z): 388.26 (M$^+$+H); Anal. calcd for C$_{27}$H$_{33}$NO: C, 83.68; H, 8.58; N, 3.61; Found: C, 83.69; H, 8.53; N, 3.65.

3,5-Bis(4-butylbenzylidene)-1-ethylpiperidin-4-one (6b)

Yield: 65%; Yellow liquid: IR (Film): ν=2957, 2930, 2858, 1672 (C=O), 1607, 1586, 1510, 1307, 1263, 1171, 989, 829; $^1$H NMR (400 MHz, CDCl$_3$): δ=0.91 (t, J=7.3 Hz, 6H, 2×PhCH$_2$CH$_2$CH$_2$CH$_3$), 1.04 (t, J=7.3 Hz, 3H, CH$_2$CH$_3$), 1.33-1.39 (m, 4H, 2×PhCH$_2$CH$_2$CH$_2$CH$_3$), 1.59-1.63 (m, 4H, 2×PhCH$_2$CH$_2$CH$_2$CH$_3$), 2.61-2.65 (m, 6H, CH$_2$CH$_3$, 2×PhCH$_2$CH$_2$CH$_2$CH$_3$), 3.85 (s, 4H, CH$_2$NCH$_2$), 7.21 (d, J=8.0 Hz, 4H, ArH), 7.30 (d, J=8.0 Hz, 4H, ArH), 7.80 (s, 2H, 2×C=CHPh) ppm; EST-MS (m/z): 416.29 (M$^+$+H); Anal. calcd for C$_{29}$H$_{37}$NO: C, 83.81; H, 8.97; N, 3.37; Found: C, 83.79; H, 8.98; N, 3.37.

3,5-Bis(4-tert-butylbenzylidene)-1-ethylpiperidin-4-one (6i)

Yield: 74%; mp: 111° C.; IR (Film): ν=2966, 2931, 2873, 1610, 1509, 1308, 1262, 1170, 990, 830; $^1$H NMR (400

MHz, CDCl$_3$): δ=1.05 (t, J=7.5 Hz, 3H, CH$_2$CH$_3$), 1.33 (s, 18H, 2×PhC(CH$_3$)$_3$), 2.59 (q, J=7.5 Hz, 2H, CH$_2$CH$_3$), 3.84 (s, 4H, CH$_2$NCH$_2$), 7.34 (d, J=8.2 Hz, 4H, ArH), 7.42 (d, J=8.2 Hz, 4H, ArH), 7.79 (s, 2H, 2×C═CHPh) ppm; $^{13}$C NMR (100 MHz, CDCl$_3$): δ=12.43, 31.14, 31.31, 34.79, 51.30, 54.47, 125.53, 130.38, 132.49, 132.58, 136.32, 152.32, 187.44 ppm; EST-MS (m/z): 416.29 (M$^+$+H); Anal. calcd for C$_{29}$H$_{37}$NO: C, 83.81; H, 8.97; N, 3.37; Found: C, 83.85; H, 9.00; N, 3.40.

1-Ethyl-3,5-bis(4-methoxybenzylidene)piperidin-4-one (6j)

Yield: 67%; mp: 156° C.; IR (Film): ν=2968, 2933, 1670 (C═O), 1599, 1510, 1302, 1256, 1167, 1030, 830, 732; $^1$H NMR (400 MHz, CDCl$_3$): δ=1.04 (t, J=7.1 Hz, 3H, CH$_2$CH$_3$), 2.62 (q, J=7.1 Hz, 2H, CH$_2$CH$_3$), 3.83 (s, 6H, 2×PhOCH$_3$), 3.85 (s, 4H, CH$_2$NCH$_2$), 6.91 (d, J=6.8 Hz, 4H, ArH), 7.34 (d, J=6.8 Hz, 4H, ArH), 7.78 (s, 2H, 2×C═CHPh) ppm; EST-MS (m/z): 364.18 (M$^+$+H); Anal. calcd for C$_{23}$H$_{25}$NO$_3$: C, 76.01; H, 6.93; N, 3.85; Found: C, 76.04; H, 6.94; N, 3.84.

Example 3. Synthesis and Characterization of 1-azidobutane (8b) and Related Compounds (8a-c)

To a mixture of butyl bromide 7b (5 g, 36.49 mmol) in DMF (30 mL) anhydrous K$_2$CO$_3$ (15.10 g, 109.48 mmol) NaN$_3$ (3.08 g, 47.44 mmol) was added. The reaction mixture was stirred overnight at 100° C. Then the reaction mixture was extracted with chloroform and organic layer was washed with water several times to remove DMF. The organic layer was dried over Na$_2$SO$_4$ and excess of solvent was removed under high vacuum to get the compound 8b. Yield: 1.90 g (52%); liquid; IR (Film): ν=3336, 3077, 2854, 2110, 1670, 1409, 1339, 1258, 1917, 911; $^1$H NMR (400 MHz, CDCl$_3$): δ=0.92 (m, 3H), 1.31-1.36 (m, 6H) ppm; ESI-MS (m/z): 100.13 (M$^+$+H).

Example 4. Synthesis and Characterization of 1-(prop-2-ynyl)piperidin-4-one (9)

In a typical reaction conditions 4-piperidone hydrochloride monohydrate 1 (5 g, 29.13 mmol) was dissolved in 20 ml, biphasic system of CHCl$_3$:H$_2$O (1:1). To this mixture, K$_2$CO$_3$ (12.06 g, 87.40 mmol) was added followed by the addition of propargyl bromide (5.17 g, 43.85 mmol). The reaction was stirred at room temperature for 8 h and progress of reaction was monitored by TLC. After completion, reaction mixture was extracted with chloroform. Organic layer was dried over Na$_2$SO$_4$ and excess of solvent was removed under high vacuum. The compound was purified over silica gel (mesh size 60-120) using EtOAc/hexane as eluent to obtain the compound 9. Yield: 3.39 g (67%); liquid; IR (Film): ν=3282, 2961, 2913, 2813, 2104 (C═CH), 1714 (C═O), 1473, 1347, 1324, 1193, 1127, 1084, 988; $^1$H NMR (400 MHz, CDCl$_3$): 2.28 (t, J=2.5 Hz, 1H, C═CH), 2.49 (t, J=5.8 Hz, 4H, 2×CH$_2$CH$_2$N), 2.89 (t, J=5.8 Hz, 4H, 2×CH$_2$CH$_2$N), 3.43 (d, J=2.2 Hz, 2H, NCH$_2$CaCH) ppm; ESI-MS (m/z): 138.08 (M$^+$+H)

Example 5. Synthesis and Characterization of 3,5-bis(4-ethylbenzylidene)-1-(prop-2-ynyl)piperidin-4-one (10b) and Related Compounds (10a-f)

Compound 9 (200 mg, 1.45 mmol) and 4-ethylbenzaldehyde (391 mg, 2.91 mmol) were dissolved in 20 mL of EtOH at 0° C. To this reaction mixture, 20% solution of NaOH (2 mL) was added dropwise. A yellow compound was precipitated out during the reaction, which was filtered and washed with cold MeOH several times. Crude product was then purified over silica gel (mesh size 60-120) using EtOH/hexane as eluent to obtain compound 10b. Yield: 328 mg (61%); mp: 130° C.; IR (Film): ν=3292, 2963, 2926, 2126 (C═CH), 1610 (C═O), 1177, 1003, 921, 830; $^1$H NMR (400 MHz, CDCl$_3$): δ=1.26 (t, J=7.3 Hz, 6H, 2×PhCH$_2$CH$_3$), 2.35 (t, J=2.2 Hz, 1H, C═CH), 2.68 (q, 4H, 2×PhCH$_2$CH$_3$), 3.51 (d, J=2.2 Hz, 2H, NCH$_2$C═CH), 3.90 (s, 4H, CH$_2$NCH$_2$), 7.24 (d, J=8.0 Hz, 4H, ArH), 7.32 (d, J=8.0 Hz, 4H, ArH), 7.79 (s, 2H, 2×C═CHPh) ppm; $^{13}$C NMR (100 MHz, CDCl$_3$): δ=17.73, 31.18, 48.98, 55.93, 77.00, 130.24, 130.58, 133.05, 134.68, 135.06, 139.01, 189.27 ppm; ESI-MS (m/z): 370.21 (M$^+$+H); Anal. calcd for C$_{26}$H$_{27}$NO: C, 84.51; H, 7.37; N, 3.79; Found: C, 84.49; H, 7.34; N, 3.75.

3,5-Bis(4-methylbenzylidene)-1-(prop-2-ynyl)piperidin-4-one (10a)

Yield: 58%; mp: 146° C.; IR (Film): ν=3284, 3243, 2918, 2146 (C═CH), 1672 (C═O), 1610, 1510, 1315, 1298, 1258, 1195, 1177, 1003, 818; $^1$H NMR (400 MHz, CDCl$_3$): δ=2.38 (s, 6H, 2×PhCH$_3$), 2.35 (t, J=2.2 Hz, 1H, C═CH), 3.51 (d, J=2.2 Hz, 2H, NCH$_2$C═CH), 3.90 (s, 4H, CH$_2$NCH$_2$), 7.21 (d, J=8.0 Hz, 4H, ArH), 7.30 (d, J=8.0 Hz, 4H, ArH), 7.79 (s, 2H, 2×C═CHPh) ppm; $^{13}$C NMR (100 MHz, CDCl$_3$): δ=23.87, 48.98, 55.93, 79.12, 131.78, 132.94, 134.64, 134.81, 139.02, 189.07 ppm; ESI-MS (m/z): 342.18 (M$^+$+H); Anal. Calcd. for C$_{24}$H$_{23}$NO: C, 84.42; H, 6.79; N, 4.10; Found: C, 84.45; H, 6.81; N, 4.13.

3,5-Bis(4-isopropylbenzylidene)-1-(prop-2-ynyl)piperidin-4-one (10c)

Yield: 58%; mp: 106° C.; IR (Film): ν=2926, 2165 (C↓CH), 1605 (C═O), 1320, 1264, 1177, 1048, 913, 816, 744; $^1$H NMR (400 MHz, CDCl$_3$): δ=1.25 (d, J=6.6 Hz, 12H, 2×PhCH(CH$_3$)$_2$), 2.35 (t, J=2.2 Hz, 1H, C═CH), 2.89-2.96 (m, 2H, 2×PhCH(CH$_3$)$_2$), 3.45 (d, J=2.9 Hz, 2H, NCH$_2$C═CH), 3.85 (s, 4H, CH$_2$NCH$_2$), 7.20 (d, J=8.0 Hz, 4H, ArH), 7.27 (d, J=8.0 Hz, 4H, ArH), 7.73 (s, 2H, 2×C═CHPh) ppm; ESI-MS (m/z): 398.24 (M$^+$+H); Anal. calcd for C$_{28}$H$_{31}$NO: C, 84.59; H, 7.86; N, 3.52; Found: C, 84.49; H, 7.83; N, 3.55.

3,5-Bis(4-tert-butylbenzylidene)-1-(prop-2-ynyl)piperidin-4-one (10d)

Yield: 56%; mp: 182° C.; IR (Film): ν=2958, 2874, 2124 (C═CH), 1672 (C═O), 1611, 1508, 1301, 1257, 1197, 1178, 1013, 825; $^1$H NMR (400 MHz, CDCl$_3$): δ=1.33 (s, 18H, 2×PhC(CH$_3$)$_3$), 2.36 (t, J=2.2 Hz, 1H, C═CH), 3.53 (d, J=2.2 Hz, 2H, NCH$_2$C═CH), 3.93 (s, 4H, CH$_2$NCH$_2$), 7.35 (d, J=8.8 Hz, 4H, ArH), 7.44 (d, J=8.8 Hz, 4H, ArH), 7.80 (s, 2H, 2×C═CHPh) ppm; $^{13}$C NMR (100 MHz, CDCl$_3$): δ=31.15, 34.81, 46.55, 53.48, 75.68, 125.59, 130.40, 132.34, 136.37, 152.44 ppm; ESI-MS (m/z): 426.27 (M$^+$+H); Anal. calcd for C$_{30}$H$_{35}$NO: C, 84.66; H, 8.29; N, 3.29; Found: C, 84.70; H, 8.27; N, 3.27.

1-(Prop-2-ynyl)-3,5-bis(4-propylbenzylidene)piperidin-4-one (10e)

Yield: 68%; mp: 96° C.; IR (Film): ν=3293, 2958, 2870, 2122 (C═CH), 1672 (C═O), 1610, 1508, 1301, 1257, 1195, 1178, 1003, 824; $^1$H NMR (400 MHz, CDCl$_3$): δ=0.87 (t, J=7.3 Hz, 6H, 2×PhCH$_2$CH$_2$CH$_3$), 1.56-1.62 (m, 4H, 2×PhCH$_2$CH$_2$CH$_3$), 2.29 (t, J=2.9 Hz, 1H, C≡CH), 2.53 (t, J=7.6 Hz, 4H, 2×PhCH$_2$CH$_2$CH$_3$), 3.46 (d, J=2.2 Hz, 2H, NCH$_2$C≡CH), 3.85 (s, 4H, CH$_2$NCH$_2$), 7.16 (d, J=8.0 Hz, 4H, ArH), 7.26 (d, J=8.0 Hz, 4H, ArH), 7.73 (s, 2H, 2×C=CHPh) ppm; ESI-MS (m/z): 398.24 (M$^+$+H); Anal. calcd for C$_{28}$H$_{31}$NO: C, 84.59; H, 7.86; N, 3.52; Found: C, 84.61; H, 7.84; N, 3.55.

3,5-Bis(4-butylbenzylidene)-1-(prop-2-ynyl)piperidin-4-one (10f)

Yield: 57%; semi-solid; IR (Film): ν=3285, 2927, 2856, 2135 (C≡CH), 1609, 1508, 1458, 1300, 1257, 1177, 1018, 1003, 828; $^1$H NMR (400 MHz, CDCl$_3$): δ=0.85 (t, J=7.6 Hz, 6H, 2×PhCH$_2$CH$_2$CH$_2$CH$_3$), 1.31-1.35 (m, 4H, 2×PhCH$_2$CH$_2$CH$_2$CH$_3$), 1.51-1.56 (m, 4H, 2×PhCH$_2$CH$_2$CH$_2$CH$_3$), 2.29 (t, J=2.2 Hz, 1H, C≡CH), 2.55-2.59 (m, 4H, 2×PhCH$_2$CH$_2$CH$_2$CH$_3$), 3.46 (d, J=2.2 Hz, 2H, NCH$_2$C≡CH), 3.85 (s, 4H, CH$_2$NCH$_2$), 7.16 (d, J=8.0 Hz, 4H, ArH), 7.25 (d, J=8.0 Hz, 4H, ArH), 7.73 (s, 2H, 2×C=CHPh) ppm; ESI-MS (m/z): 426.27 (M$^+$+H); Anal. calcd for C$_{30}$H$_{35}$NO: C, 84.66; H, 8.29; N, 3.29; Found: C, 84.70; H, 8.24; N, 3.26.

Example 6. Synthesis and Characterization of 1-((1-butyl-1H-1,2,3-triazol-4-yl)methyl)-3,5-bis(4-methylbenzylidene)piperidin-4-one (11b) and Related Compounds (11a-c, 12a-c, 13a-c, 14a-c, 15a-c, 16a-c)

Compound 10a (150 mg, 0.44 mmol) and 4-butylazide 8b (44 mg, 0.44 mmol) were dissolved in 10 mL of t-BuOH at room temperature. To this reaction mixture, mixture of CuSO$_4$.2H$_2$O (44 mg, 0.18 mmol) and sodium ascorbate (52 mg, 0.35 mmol) in 10 mL of water was added and reaction mixture was stirred at 40-45° C. for 3 h. After completion, reaction mixture was extracted with chloroform and organic layer was dried over Na$_2$SO$_4$. Excess of organic solvent was removed under high vacuum. The crude product was purified over silica gel using EtOH/hexane as eluent to obtained compound 13b. Yield: 124 mg (63%); mp: 148° C.; IR (Film): ν=2927, 1605, 1320, 1264, 1177, 1048, 1000, 913, 816, 744; $^1$H NMR (400 MHz, CDCl$_3$): δ=0.75 (t, J=7.3 Hz, 3H, NCH$_2$CH$_2$CH$_2$CH$_3$), 1.07-1.15 (m, 2H, NCH$_2$CH$_2$CH$_2$CH$_3$), 1.62-1.66 (m, 2H, NCH$_2$CH$_2$CH$_2$CH$_3$), 2.29 (s, 6H, 2×PhCH$_3$), 3.80 (s, 6H, N(CH$_2$)$_3$), 4.14 (t, J=6.9 Hz, 2H, NCH$_2$CH$_2$CH$_2$CH$_3$), 7.13 (d, J=8.0 Hz, 4H, ArH), 7.19 (s, 1H, C=CH), 7.21 (d, J=8.0 Hz, 4H, ArH), 7.69 (s, 2H, 2×C=CHPh) ppm; $^{13}$C NMR (100 MHz, CDCl$_3$): δ=13.73, 21.40, 28.39, 29.75, 50.18, 52.60, 54.67, 122.27, 129.27, 129.34, 130.50, 132.29, 136.48, 139.37, 144.40, 187.38 ppm; ESI-MS (m/z): 441.26 (M$^+$+H); Anal. calcd for C$_{28}$H$_{32}$N$_4$O: C, 76.33; H, 7.32; N, 12.72; Found: C, 76.35; H, 7.34; N, 12.73.

3,5-Bis(4-methylbenzylidene)-1-((1-propyl-1H-1,2,3-triazol-4-yl)methyl)piperidin-4-one (11a)

Yield: 59%; mp: 165° C.; IR (Film): ν=2925, 2856, 1596, 1441, 1265, 1177, 1051, 811; $^1$H NMR (400 MHz, CDCl$_3$): δ=0.73 (t, J=7.3 Hz, 3H, NCH$_2$CH$_2$CH$_3$), 1.66-1.70 (m, 2H, NCH$_2$CH$_2$CH$_3$), 2.30 (s, 6H, 2×PhCH$_3$), 3.81 (s, 6H, N(CH$_2$)$_3$), 4.12 (t, J=6.9 Hz, 2H, NCH$_2$CH$_2$CH$_3$), 7.13 (d, J=8.0 Hz, 4H, ArH), 7.19 (s, 1H, C=CH), 7.20 (d, J=8.0 Hz, 4H, ArH), 7.70 (s, 2H, 2×C=CHPh) ppm; ESI-MS (m/z): 427.24 (M$^+$+H); Anal. calcd for C$_{27}$H$_{30}$N$_4$O: C, 76.03; H, 7.09; N, 13.13; Found: C, 76.05; H, 7.11; N, 13.14.

3,5-Bis(4-methylbenzylidene)-1-((1-pentyl-1H-1,2,3-triazol-4-yl)methyl)piperidin-4-one (11c)

Yield: 55%; mp: 169° C.; IR (Film): ν=2925, 2855, 1670 (C=O), 1606, 1510, 1458, 1320, 1291, 1265, 1177, 1049, 1019, 813; $^1$H NMR (400 MHz, CDCl$_3$): δ=0.73 (t, J=7.3 Hz, 3H, NCH$_2$CH$_2$CH$_2$CH$_2$CH$_3$), 1.09-1.19 (m, 4H, NCH$_2$CH$_2$CH$_2$CH$_2$CH$_3$), 1.66-1.69 (m, 2H, NCH$_2$CH$_2$CH$_2$CH$_2$CH$_3$), 2.30 (s, 6H, 2×PhCH$_3$), 3.81 (s, 6H, N(CH$_2$)$_3$), 4.12 (t, J=7.6 Hz, 2H, NCH$_2$CH$_2$CH$_2$CH$_2$CH$_3$), 7.12 (d, J=8.0 Hz, 4H, ArH), 7.19 (s, 1H, C=CH), 7.20 (d, J=8.0 Hz, 4H, ArH), 7.70 (s, 2H, 2×C=CHPh) ppm; $^{13}$C NMR (100 MHz, CDCl$_3$): δ=13.73, 21.40, 21.91, 28.39, 29.75, 50.18, 52.60, 54.67, 122.27, 129.34, 130.54, 132.29, 136.48, 139.37, 144.40, 187.38 ppm; ESI-MS (m/z): 455.27 (M$^+$+H); Anal. calcd for C$_{29}$H$_{34}$N$_4$O: C, 76.62; H, 7.54; N, 12.32; Found: C, 76.65; H, 7.55; N, 12.35.

3,5-Bis(4-ethylbenzylidene)-1-((1-propyl-1H-1,2,3-triazol-4-yl)methyl)piperidin-4-one (12a)

Yield: 65%; mp: 149° C.; IR (Film) ν=2962, 2929, 2859, 1604, 1445, 1326, 1226, 1179, 1051, 1020, 930, 825; $^1$H NMR (400 MHz, CDCl$_3$): δ=0.72 (t, J=7.3 Hz, 3H, NCH$_2$CH$_2$CH$_3$), 1.18 (t, J=7.3 Hz, 6H, 2×PhCH$_2$CH$_3$), 1.67-1.70 (m, 2H, NCH$_2$CH$_2$CH$_3$), 2.57 (q, 4H, 2×PhCH$_2$CH$_3$), 3.82 (s, 6H, N(CH$_2$)$_3$), 4.13 (t, J=7.3 Hz, 2H, NCH$_2$CH$_2$CH$_3$), 7.15 (d, J=8.0 Hz, 4H, ArH), 7.19 (s, 1H, C=CH), 7.23 (d, J=8.0 Hz, 4H, ArH), 7.71 (s, 2H, 2×C=CHPh) ppm; $^{13}$C NMR (100 MHz, CDCl$_3$): δ=13.75, 15.28, 21.91, 28.40, 28.72, 29.75, 50.20, 52.63, 54.71, 122.32, 128.16, 130.64, 132.32, 132.53, 136.49, 144.41, 145.65, 187.62 ppm; ESI-MS (m/z): 455.27 (M$^+$+H); Anal. calcd for C$_{29}$H$_{34}$N$_4$O: C, 76.62; H, 7.54; N, 12.32; Found: C, 76.65; H, 7.55; N, 12.35.

1-((1-Butyl-1H-1,2,3-triazol-4-yl)methyl)-3,5-bis(4-ethylbenzylidene)piperidin-4-one (12b)

Yield: 59%; mp: 150° C.; IR (Film): ν=2963, 2929, 2873, 1670 (C=O), 1606, 1509, 1459, 1327, 1267, 1226, 1226, 1181, 1051, 1020, 826; $^1$H NMR (400 MHz, CDCl$_3$): δ=0.74 (t, J=7.3 Hz, 3H, NCH$_2$CH$_2$CH$_2$CH$_3$), 1.10-1.21 (m, 8H, NCH$_2$CH$_2$CH$_2$CH$_3$, 2×PhCH$_2$CH$_3$), 1.64-1.68 (m, 2H, NCH$_2$CH$_2$CH$_2$CH$_3$), 2.57 (q, 4H, 2×PhCH$_2$CH$_3$), 3.83 (s, 6H, N(CH$_2$)$_3$), 4.14 (t, J=7.7 Hz, 2H, NCH$_2$CH$_2$CH$_2$CH$_3$), 7.21 (d, J=8.0 Hz, 4H, ArH), 7.17 (s, 1H, C=CH), 7.29 (d, J=8.0 Hz, 4H, ArH), 7.72 (s, 2H, 2×C=CHPh) ppm; $^{13}$C NMR (100 MHz, CDCl$_3$): δ=13.31, 15.29, 19.49, 28.72, 32.02, 49.91, 52.62, 54.69, 54.98, 122.32, 128.16, 130.63, 132.32, 132.53, 136.50, 144.30, 145.64, 186.88 ppm; ESI-MS (m/z): 469.29 (M$^+$+H); Anal. calcd for C$_{30}$H$_{36}$N$_4$O: C, 76.89; H, 7.74; N, 11.96; Found: C, 76.89; H, 7.74; N, 11.96.

3,5-Bis(4-ethylbenzylidene)-1-((1-pentyl-1H-1,2,3-triazol-4-yl)methyl)piperidin-4-one (12c)

Yield: 67%; mp: 156° C.; IR (Film): ν=2961, 2928, 2858, 1668 (C=O), 1606, 1510, 1462, 1420, 1195, 1177, 1051, 1019, 929, 826; $^1$H NMR (400 MHz, CDCl$_3$): δ=0.75 (t, J=6.9 Hz, 3H, NCH$_2$CH$_2$CH$_2$CH$_2$CH$_3$), 1.12-1.18 (m, 4H, NCH$_2$CH$_2$CH$_2$CH$_2$CH$_3$), 1.19 (t, J=7.3 Hz, 6H, 2×PhCH$_2$CH$_3$), 1.69-1.73 (m, 2H, NCH$_2$CH$_2$CH$_2$CH$_2$CH$_3$), 2.60 (q, 4H, 2×PhCH$_2$CH$_3$), 3.85 (s, 6H, N(CH$_2$)$_3$), 4.15 (t, J=7.3 Hz, 2H, NCH$_2$CH$_2$CH$_2$CH$_3$), 7.19 (s, 1H, C=CH), 7.21 (d, J=8.0 Hz, 4H, ArH), 7.27 (d, J=8.0 Hz, 4H, ArH), 7.74 (s, 2H, 2×C=CHPh) ppm; $^{13}$C NMR (100 MHz, CDCl$_3$): δ=13.73, 15.27, 21.90, 28.39, 28.71, 29.74, 50.19, 52.63, 54.70, 122.30, 128.15, 130.62, 132.32, 132.53, 144.40, 145.63, 187.40 ppm; ESI-MS (m/z): 483.30 (M$^+$+H); Anal. calcd for C$_{31}$H$_{38}$N$_4$O: C, 77.14; H, 7.94; N, 11.61; Found: C, 77.15; H, 7.95; N, 11.64.

3,5-Bis(4-isopropylbenzylidene)-1-((1-propyl-1H-1,2,3-triazol-4-yl)methyl)piperidin-4-one (13a)

Yield: 55%; mp: 144° C.; IR (Film): ν=2959, 2928, 2871, 1672 (C=O), 1610, 1508, 1461, 1180, 1051, 1000, 829; $^1$H NMR (400 MHz, CDCl$_3$): (t, J=6.9 Hz, 3H, NCH$_2$CH$_2$CH$_3$), 1.19 (d, J=7.3 Hz, 12H, 2×PhCH(CH$_3$)$_2$), 1.71-1.78 (m, 2H, NCH$_2$CH$_2$CH$_3$), 2.85-2.88 (m, 2H, 2×PhCH(CH$_3$)$_2$), 3.84 (s, 6H, N(CH$_2$)$_3$), 4.14 (t, J=7.3 Hz, 2H, NCH$_2$CH$_2$CH$_3$), 7.20 (d, J=8.0 Hz, 5H, ArH, C=CH), 7.26 (d, J=8.0 Hz, 4H, ArH), 7.74 (s, 2H, 2×C=CHPh) ppm; ESI-MS (m/z): 483.30 (M$^+$+H); Anal. calcd for C$_{31}$H$_{38}$N$_4$O: C, 77.14; H, 7.94; N, 11.61; Found: C, 77.16; H, 7.96; N, 11.66.

1-((1-Butyl-1H-1,2,3-triazol-4-yl)methyl)-3,5-bis(4-isopropyl benzylidene)piperidin-4-one (13b)

Yield: 55%; mp: 145° C.; IR (Film): ν=2959, 2929, 2871, 1605, 1459, 1325, 1184, 1050, 1019, 931, 825; $^1$H NMR (400 MHz, CDCl$_3$): δ=0.74 (t, J=7.7 Hz, 3H, NCH$_2$CH$_2$CH$_2$CH$_3$), 1.10-1.16 (m, 2H, NCH$_2$CH$_2$CH$_2$CH$_3$), 1.18 (d, J=7.3 Hz, 12H, 2×PhCH(CH$_3$)$_2$), 1.64-1.79 (m, 2H, NCH$_2$CH$_2$CH$_2$CH$_3$), 2.81-2.91 (m, 2H, 2×PhCH(CH$_3$)$_2$), 3.83 (s, 6H, N(CH$_2$)$_3$), 4.14 (t, J=7.3 Hz, 2H, NCH$_2$CH$_2$CH$_2$CH$_3$), 7.24-7.25 (m, 5H, ArH, C=CH), 7.29 (d, J=8.0 Hz, 4H, ArH), 7.76 (s, 2H, 2×C=CHPh) ppm; $^{13}$C NMR (100 MHz, CDCl$_3$): δ=13.31, 19.49, 23.75, 24.08, 32.01, 33.99, 49.92, 52.80, 54.26, 121.90, 126.75, 126.78, 130.67, 132.12, 136.51, 150.1, 187.41 ppm; ESI-MS (m/z): 497.32 (M$^+$+H); Anal. calcd for C$_{32}$H$_{40}$N$_4$O: C, 77.38; H, 8.12; N, 11.28; Found: C, 77.36; H, 8.10; N, 11.24.

3,5-Bis(4-isopropylbenzylidene)-1-((1-pentyl-1H-1,2,3-triazol-4-yl)methyl)piperidin-4-one (13e)

Yield: 60%; mp: 143° C.; IR (Film) ν=2959, 2931, 1672, 1612, 1584, 1461, 1265, 1180, 1051, 1000, 830, 732; $^1$H NMR (400 MHz, CDCl$_3$): δ=0.77 (t, J=6.6 Hz, 3H, NCH$_2$CH$_2$CH$_2$CH$_3$), 1.07-1.14 (m, 4H, NCH$_2$CH$_2$CH$_2$CH$_3$), 1.19 (d, J=7.3 Hz, 12H, 2×PhCH(CH$_3$)$_2$), 1.67-1.75 (m, 2H, NCH$_2$CH$_2$CH$_2$CH$_3$), 2.81-2.92 (m, 2H, 2×PhCH(CH$_3$)$_2$), 3.88 (s, 6H, N(CH$_2$)$_3$), 4.18 (t, J=7.3 Hz, 2H, NCH$_2$CH$_2$CH$_2$CH$_3$), 7.24 (d, J=6.6 Hz, 4H, ArH), 7.29 (s, 1H, C=CH), 7.30 (d, J=8.0 Hz, 4H, ArH), 7.75 (s, 2H, 2×C=CHPh) ppm; $^{13}$C NMR (100 MHz, CDCl$_3$): δ=13.74, 21.90, 23.74, 28.39, 29.74, 33.98, 50.20, 52.68, 54.74, 122.32, 126.74, 130.67, 132.34, 132.68, 136.39, 144.42, 150.21, 187.41 ppm; ESI-MS (m/z): 511.34 (M$^+$+H); Anal. calcd for C$_{33}$H$_{42}$N$_4$O: C, 77.61; H, 8.29; N, 10.97; Found: C, 77.64; H, 8.25; N, 10.96.

3,5-Bis(4-tert-butylbenzylidene)-1-((1-propyl-1H-1,2,3-triazol-4-yl)methyl)piperidin-4-one (14a)

Yield: 69%; mp: 182° C.; IR (Film): ν=2905, 2963, 2871, 1671 (C=O), 1611, 1462, 1265, 1182, 1000, 834; $^1$H NMR (400 MHz, CDCl$_3$): δ=0.66 (t, J=7.3 Hz, 3H, NCH$_2$CH$_2$CH$_3$), 1.24 (s, 18H, 2×PhC(CH$_3$)$_3$), 1.66-1.70 (m, 2H, NCH$_2$CH$_2$CH$_3$), 3.82 (s, 6H, N(CH$_2$)$_3$), 4.09 (t, J=7.3 Hz, 2H, NCH$_2$CH$_2$CH$_3$), 7.17 (s, 1H, C=CH), 7.24 (d, J=8.0 Hz, 4H, ArH), 7.33 (d, J=8.0 Hz, 4H, ArH), 7.69 (s, 2H, 2×C=CHPh) ppm; ESI-MS (m/z): 511.34 (M$^+$+H); Anal. calcd for C$_{33}$H$_{42}$N$_4$O: C, 77.14; H, 7.94; N, 11.61; Found: C, 77.11; H, 7.91; N, 11.64.

1-[(1-Butyl-1H-1,2,3-triazol-4-yl)methyl]-3,5-bis(4-tert-butylbenzylidene)piperidin-4-one (14b)

Yield: 63%; mp: 145° C.; IR (Film): ν=2956, 2928, 2858, 1667 (C=O), 1605, 1575, 1511, 1465, 1330, 1269, 1181, 1051, 1020, 822; $^1$H NMR (400 MHz, CDCl$_3$): δ=0.72 (t, J=7.3 Hz, 3H, NCH$_2$CH$_2$CH$_2$CH$_3$), 1.09-1.18 (m, 2H, NCH$_2$CH$_2$CH$_2$CH$_3$), 1.26 (s, 18H, 2×PhC(CH$_3$)$_3$), 1.65-1.72 (m, 2H, NCH$_2$CH$_2$CH$_2$CH$_3$), 3.81 (s, 6H, N(CH$_2$)$_3$), 4.15 (t, J=7.3 Hz, 2H, NCH$_2$CH$_2$CH$_2$CH$_3$), 7.17 (s, 1H, C=CH), 7.24 (d, J=8.8 Hz, 4H, ArH), 7.33 (d, J=8.8 Hz, 4H, ArH), 7.69, (s, 2H, 2×C=CHPh) ppm; ESI-MS (m/z): 525.35 (M$^+$+H); Anal. calcd for C$_{34}$H$_{44}$N$_4$O: C, 77.82; H, 8.45; N, 10.68; Found: C, 77.80; H, 8.49; N, 10.66.

3,5-Bis(4-tert-butylbenzylidene)-1-[(1-pentyl-1H-1,2,3-triazol-4-yl)methyl]piperidin-4-one (14c)

Yield: 61%; mp: 146° C.; IR (Film): ν=2959, 2925, 2855, 1611, 1459, 1264, 1182, 1016, 1000, 833; $^1$H NMR (400 MHz, CDCl$_3$): δ=0.74 (t, J=7.3 Hz, 3H, NCH$_2$CH$_2$CH$_2$CH$_2$CH$_3$), 1.07-1.22 (m, 4H, NCH$_2$CH$_2$CH$_2$CH$_2$CH$_3$), 1.26 (s, 18H, 2×PhC(CH$_3$)$_3$), 1.67-1.75 (m, 2H, NCH$_2$CH$_2$CH$_2$CH$_2$CH$_3$), 3.86 (s, 6H, N(CH$_2$)$_3$), 4.16 (t, J=7.3 Hz, 2H, NCH$_2$CH$_2$CH$_2$CH$_2$CH$_3$), 7.21 (s, 1H, C=CH), 7.28 (d, J=8.8 Hz, 4H, ArH), 7.37 (d, J=8.8 Hz, 4H, ArH), 7.72 (s, 2H, 2×C=CHPh) ppm; $^{13}$C NMR (100 MHz, CDCl$_3$): δ=13.75, 21.91, 28.41, 29.75, 31.13, 34.80, 49.87, 52.31, 54.78, 122.35, 125.61, 130.44, 132.31, 132.46, 136.23, 144.79, 152.46, 187.13 ppm; ESI-MS (m/z): 539.37 (M$^+$+H); Anal. calcd for C$_{35}$H$_{46}$N$_4$O: C, 78.03; H, 8.61; N, 10.40; Found: C, 78.08; H, 8.64; N, 10.44.

1-[(1-Propyl-1H-1,2,3-triazol-4-yl)methyl]-3,5-bis(4-propylbenzyl idene)piperidin-4-one (15a)

Yield: 69%; mp: 133° C.; IR (Film): ν=2955, 2928, 2868, 1604, 1458, 1051, 1019, 806; $^1$H NMR (400 MHz, CDCl$_3$): δ=0.77 (t, J=7.3 Hz, 3H, NCH$_2$CH$_2$CH$_3$), 0.91 (t, J=7.6 Hz, 6H, 2×PhCH$_2$CH$_2$CH$_3$), 1.60-1.65 (m, 2H, NCH$_2$CH$_2$CH$_3$), 1.72-1.77 (m, 4H, 2×PhCH$_2$CH$_2$CH$_3$), 2.56 (t, J=6.9 Hz, 4H, 2×PhCH$_2$CH$_2$CH$_3$), 3.87 (s, 6H, N(CH$_2$)$_3$), 4.17 (t, J=6.6 Hz, 2H, NCH$_2$CH$_2$CH$_3$), 7.18 (d, J=8.0 Hz, 4H, ArH), 7.24 (s, 1H, C=CH), 7.27 (d, J=8.0 Hz, 4H, ArH), 7.78 (s, 2H, 2×C=CHPh) ppm; ESI-MS (m/z): 483.30 (M$^+$+H); Anal. calcd for C$_{31}$H$_{38}$N$_4$O: C, 77.14; H, 7.94; N, 11.61; Found: C, 77.16; H, 7.96; N, 11.64.

1-[(1-Butyl-1H-1,2,3-triazol-4-yl)methyl]-3,5-bis(4-propyibenzylidene)piperidin-4-one (15b)

Yield: 67%; mp: 144° C.; IR (Film): ν=2957, 2929, 2871, 1665 (C=O), 1605, 1575, 1560, 1181, 1050, 1020, 821; $^1$H NMR (400 MHz, CDCl$_3$): δ=0.74 (t, J=7.3 Hz, 3H, NCH$_2$CH$_2$CH$_2$CH$_3$), 0.86 (t, J=7.3 Hz, 6H, 2×PhCH$_2$CH$_2$CH$_3$), 1.10-1.16 (m, 2H, NCH$_2$CH$_2$CH$_2$CH$_3$), 1.54-1.69 (m, 6H, NCH$_2$CH$_2$CH$_2$CH$_3$, 2×PhCH$_2$CH$_2$CH$_3$), 2.51 (t, J=7.7 Hz, 4H, 2×PhCH$_2$CH$_2$CH$_3$), 3.82 (s, 6H, N(CH$_2$)$_3$), 4.14 (t, J=7.3 Hz, 2H, NCH$_2$CH$_2$CH$_2$CH$_3$), 7.13 (d, J=8.0 Hz, 4H, ArH), 7.19 (s, 1H, C=CH), 7.22 (d, J=8.0 Hz, 4H, ArH), 7.71 (s, 2H, 2×C=CHPh) ppm; $^{13}$C NMR (100 MHz, CDCl$_3$): δ=13.31, 13.83, 19.50, 24.32, 32.02, 37.87, 49.91, 52.55, 54.70, 122.32, 128.75, 130.54, 132.30, 132.54, 136.51, 144.16, 187.13 ppm; ESI-MS (m/z): 497.32 (M$^+$+H); Anal. calcd for C$_{32}$H$_{40}$N$_4$O: C, 77.38; H, 8.12; N, 11.28; Found: C, 77.34; H, 8.15; N, 11.30.

1-[(1-Pentyl-1H-1,2,3-triazol-4-yl)methyl]-3,5-bis(4-propylbenzylidene)piperidin-4-one (15e)

Yield: 59%; mp: 134° C.; IR (Film): ν=2956, 2929, 2869, 1666 (C=O), 1605, 1560, 1465, 1267, 1179, 1051, 1020, 807; $^1$H NMR (400 MHz, CDCl$_3$): δ=0.74 (t, J=7.3 Hz, 3H, NCH$_2$CH$_2$CH$_2$CH$_3$), 0.86 (t, J=7.3 Hz, 6H, 2×PhCH$_2$CH$_2$CH$_3$), 1.10-1.19 (m, 4H, NCH$_2$CH$_2$CH$_2$CH$_3$), 1.55-1.69 (m, 6H, NCH$_2$CH$_2$CH$_2$CH$_3$, 2×PhCH$_2$CH$_2$CH$_3$), 2.51 (t, J=8.0 Hz, 4H, 2×PhCH$_2$CH$_2$CH$_3$), 3.82 (s, 6H, N(CH$_2$)$_3$), 4.12 (t, J=7.3 Hz, 2H, NCH$_2$CH$_2$CH$_2$CH$_3$), 7.13 (d, J=8.7 Hz, 4H, ArH), 7.19 (s, 1H, C=CH), 7.22 (d, J=8.8 Hz, 4H, ArH), 7.70 (s, 2H, 2×C=CHPh) ppm; $^{13}$C NMR (100 MHz, CDCl$_3$): δ=13.83, 21.92, 24.32, 28.41, 29.76, 37.87, 50.21, 52.80, 54.70, 122.33, 128.75, 130.55, 132.53, 136.52, 144.18, 187.13 ppm; ESI-MS (m/z): 511.34 (M$^+$+H); Anal. calcd for C$_{33}$H$_{42}$N$_4$O: C, 77.61; H, 8.29; N, 10.97; Found: C, 77.64; H, 8.27; N, 10.96.

3,5-Bis(4-butylbenzylidene)-1-[(1-propyl-1H-1,2,3-triazol-4-yl)methyl]piperidin-4-one (16a)

Yield: 57%; mp: 127° C.; IR (Film): ν=2957, 2928, 2858, 1666, 1605, 1577, 1465, 1269, 1197, 1179, 1051, 1004, 823; $^1$H NMR (400 MHz, CDCl$_3$): δ=0.74 (t, J=7.3 Hz, 3H, NCH$_2$CH$_2$CH$_3$), 0.85 (t, J=7.3 Hz, 6H, 2×PhCH$_2$CH$_2$CH$_2$CH$_3$), 1.19-1.32 (m, 4H, 2×PhCH$_2$CH$_2$CH$_2$CH$_3$), 1.52-1.55 (m, 4H, 2×PhCH$_2$CH$_2$CH$_2$CH$_3$), 1.63-1.73 (m, 2H, NCH$_2$CH$_2$CH$_3$), 2.54 (t, J=7.3 Hz, 4H, 2×PhCH$_2$CH$_2$CH$_2$CH$_3$), 3.91 (s, 6H, N(CH$_2$)$_3$), 4.12 (t, J=7.3 Hz, 2H, NCH$_2$CH$_2$CH$_3$), 7.14 (d, J=8.0 Hz, 4H, ArH), 7.19 (s, 1H, C=CH), 7.20 (d, J=8.0 Hz, 4H, ArH), 7.82 (s, 2H, 2×C=CHPh) ppm; ESI-MS (m/z): 511.34 (M$^+$+H); Anal. calcd for C$_{33}$H$_{42}$N$_4$O: C, 77.61; H, 8.29; N, 10.97; Found: C, 77.58; H, 8.31; N, 11.00.

1-[(1-Butyl-1H-1,2,3-triazol-4-yl)methyl]-3,5-bis(4-butylbenzylidene)piperidin-4-one (16b)

Yield: 63%; mp: 136° C.; IR (Film): ν=2957, 2928, 2858, 1666 (C=O), 1605, 1576, 1463, 1330, 1178, 1050, 822; $^1$H NMR (400 MHz, CDCl$_3$): δ=0.81 (t, J=7.3 Hz, 3H, NCH$_2$CH$_2$CH$_2$CH$_3$), 0.89 (t, J=7.3 Hz, 6H, 2×PhCH$_2$CH$_2$CH$_2$CH$_3$), 1.15-1.21 (m, 2H, NCH$_2$CH$_2$CH$_2$CH$_3$), 1.31-1.37 (m, 4H, 2×PhCH$_2$CH$_2$CH$_2$CH$_3$), 1.56-1.60 (m, 4H, 2×PhCH$_2$CH$_2$CH$_2$CH$_3$), 1.61-1.71 (m, 2H, NCH$_2$CH$_2$CH$_2$CH$_3$), 2.58 (t, J=7.3 Hz, 4H, 2×PhCH$_2$CH$_2$CH$_2$CH$_3$), 3.87 (s, 6H, N(CH$_2$)$_3$), 4.19 (t, J=6.9 Hz, 2H, NCH$_2$CH$_2$CH$_2$CH$_3$), 7.18 (d, J=8.0 Hz, 4H, ArH), 7.24 (s, 1H, C=CH), 7.27 (d, J=8.0 Hz, 4H, ArH), 7.75 (s, 2H, 2×C=CHPh) ppm; $^{13}$C NMR (100 MHz, CDCl$_3$): δ=13.31, 13.92, 19.50, 22.35, 32.02, 33.36, 35.50, 49.91, 52.31, 54.70, 121.90, 128.69, 130.56, 132.30, 132.50, 136.50, 144.39, 187.13 ppm; ESI-MS (m/z): 525.35 (M$^+$+H); Anal. calcd for C$_{34}$H$_{44}$N$_4$O: C, 77.82; H, 8.45; N, 10.68; Found: C, 77.80; H, 8.43; N, 10.65.

3,5-Bis(4-butylbenzylidene)-1-[(1-pentyl-1H-1,2,3-triazol-4-yl)methyl]piperidin-4-one (16c)

Yield: 58%; mp: 145° C.; IR (Film): ν=2956, 2928, 2859, 1665 (C=O), 1604, 1574, 1225, 1051, 822; $^1$H NMR (400 MHz, CDCl$_3$): δ=0.79 (t, J=6.6 Hz, 3H, NCH$_2$CH$_2$CH$_2$CH$_2$CH$_3$), 0.89 (t, J=7.3 Hz, 6H, 2×PhCH$_2$CH$_2$CH$_2$CH$_3$), 1.15-1.37 (m, 8H, 2×PhCH$_2$CH$_2$CH$_2$CH$_3$, NCH$_2$CH$_2$CH$_2$CH$_2$CH$_3$), 1.56-1.60 (m, 4H, 2×PhCH$_2$CH$_2$CH$_2$CH$_3$), 1.67-1.71 (m, 2H, NCH$_2$CH$_2$CH$_2$CH$_2$CH$_3$), 2.58 (t, J=7.3 Hz, 4H, 2×PhCH$_2$CH$_2$CH$_2$CH$_3$), 3.87 (s, 6H, N(CH$_2$)$_3$), 4.17 (t, J=7.3 Hz, 2H, NCH$_2$CH$_2$CH$_2$CH$_2$CH$_3$), 7.18 (d, J=8.0 Hz, 4H, ArH), 7.24 (s, 1H, C=CH), 7.27 (d, J=8.0 Hz, 4H, ArH), 7.75 (s, 2H, 2×C=CHPh) ppm; $^{13}$C NMR (100 MHz, CDCl$_3$): δ=13.75, 13.92, 21.92, 22.35, 28.41, 29.76, 33.36, 35.50, 50.21, 53.03, 54.72, 122.31, 128.70, 130.57, 132.30, 132.51, 136.48, 144.39, 187.37 ppm; ESI-MS (m/z): 539.37 (M$^+$+H); Anal. calcd for C$_{35}$H$_{46}$N$_4$O: C, 78.03; H, 8.61; N, 10.40; Found: C, 78.00; H, 8.64; N, 10.43.

Example 7. Evaluation of Cytotoxicity

Cell Culture Methods

Two cell human cancer cell lines were used in this study: human cervical cancer cells (HeLa) and human embryonic kidney 293 cells (Hek). The cell lines were obtained from ATCC (Rockville, Md., USA). Cell lines were cultured at 37° C. and 5% CO$_2$ in DMEM medium with 10% fetal bovine serum (FBS) and 1% penicillin/streptomycin (all obtained from GibcoBRL, Grand Island, N.Y.). Cells were passaged three times weekly by trypsinisation with 0.25% trypsin/0.02% EDTA solution (Sigma) into 75 cm$^2$ tissue culture flasks (Nunc, Denmark).

MTT Assay

Both human cervical cancer cells (HeLa) and human embryonic kidney 293 cells (Hek) cell lines were seeded into 96-well plate (2.5×10$^4$ in 100 μL per well). Testing compounds were dissolved or suspended in DMSO to make 10 mM stock solutions. Addition of compounds was performed after adherent cells reached 40-50% confluence. After incubation for 48 h at 37° C. in humidified atmosphere with 5% CO$_2$, 10 μL of MTT (5 mg/mL in PBS) was added to each well and incubated for another 4 h. The culture medium was then aspirated and 100 μL of DMSO was added to each well. Optical densities at 490 nm were measured by microplate reader (PERKINELMER VICTOR 3V model 1420). All tests were performed in triplicates. Doxorubicin was used as a positive control and the same amount DMSO without compound was used as negative control. $IC_{50}$ values were obtained from the curve fitting by using Sigma plot10.

Results

Figure 2:
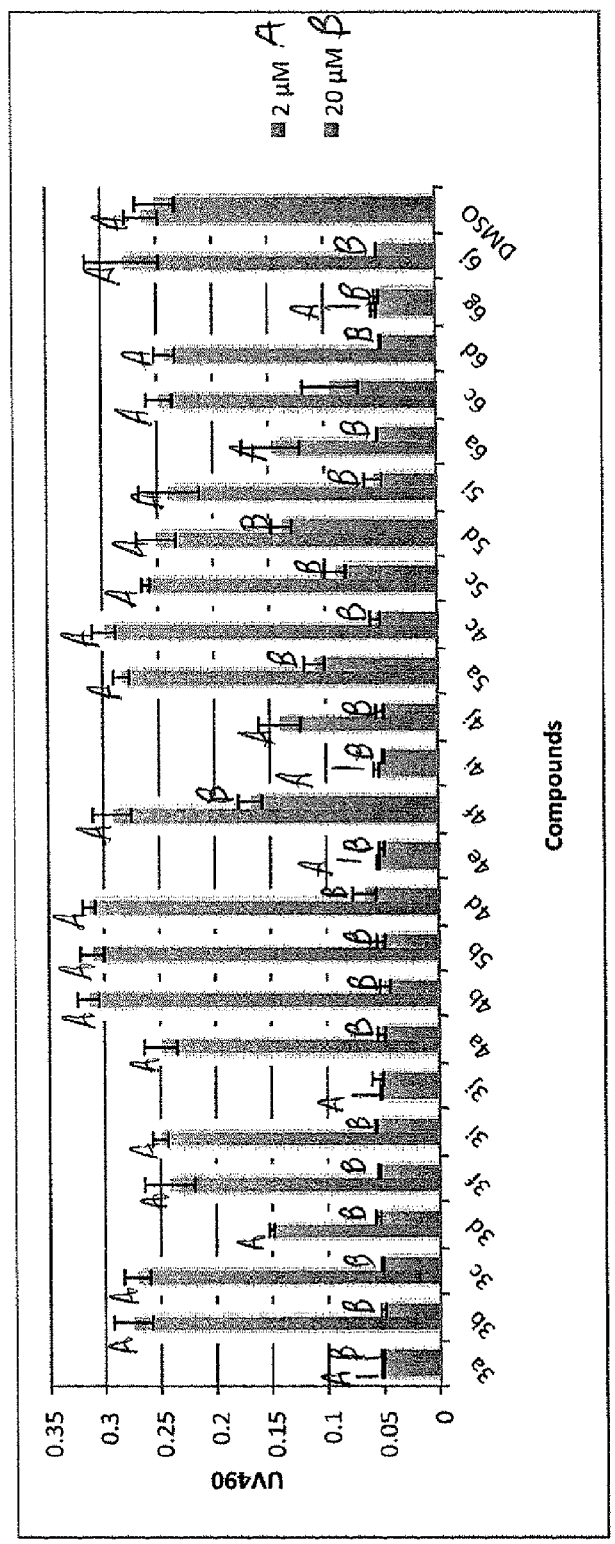
FIG. 2 is a bar graph showing the cytotoxicity of curcumin analogues in Hela cells using the MTT assay at 20 µM (red color bars) and 2 µM (blue color bars). Data represents average values of three replicates.
Figure 3A:
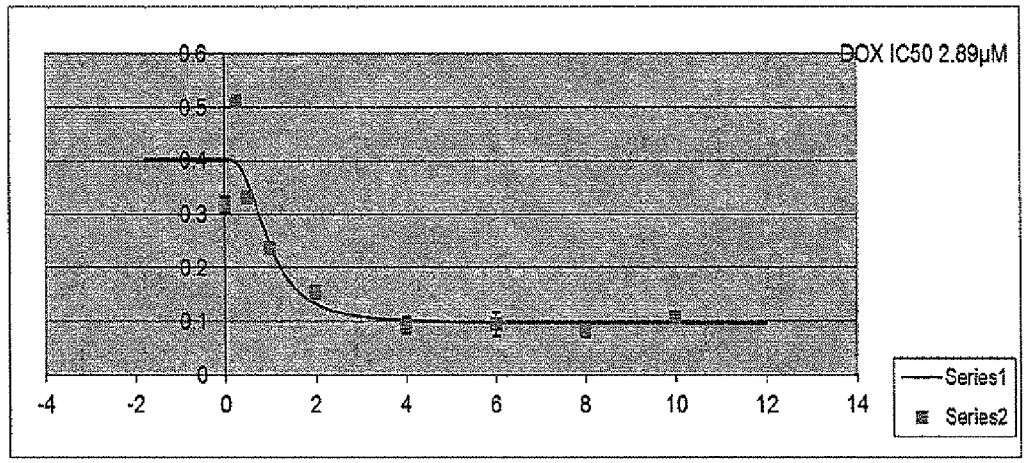
FIGS. 3A-D are dose response curves for doxorubicin and compounds 3a, 3j, and 4e against Hela cells.
Figure 3B:
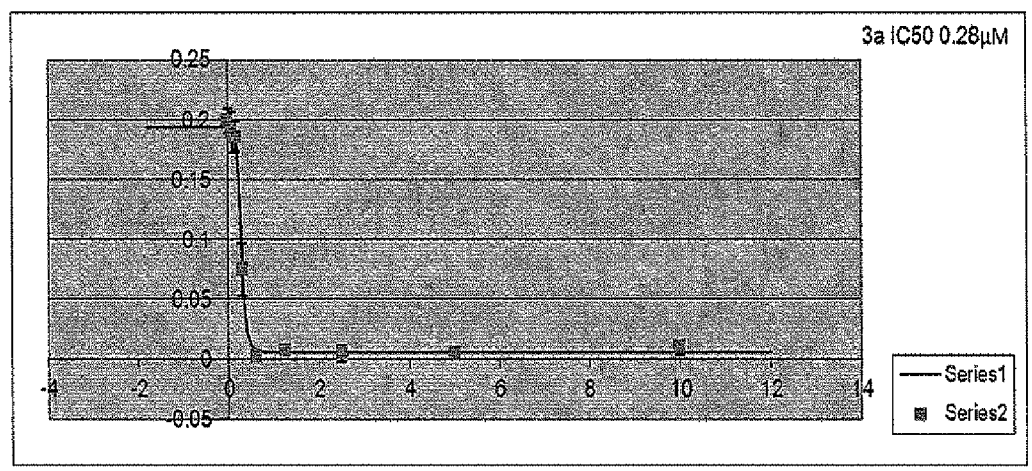
Figure 3C:
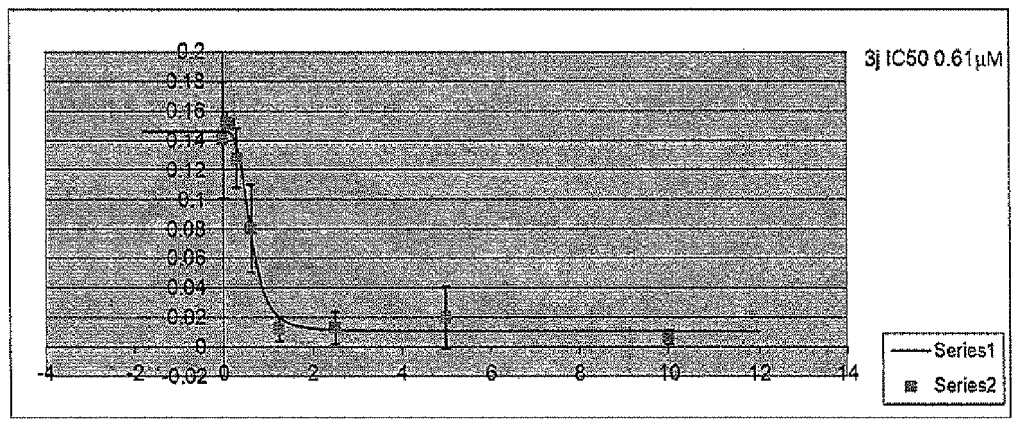
Figure 3D:
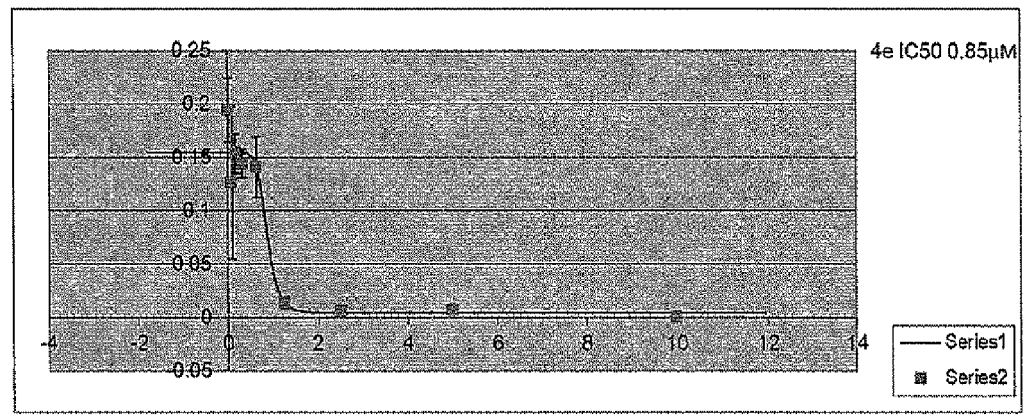
Figure 4A:
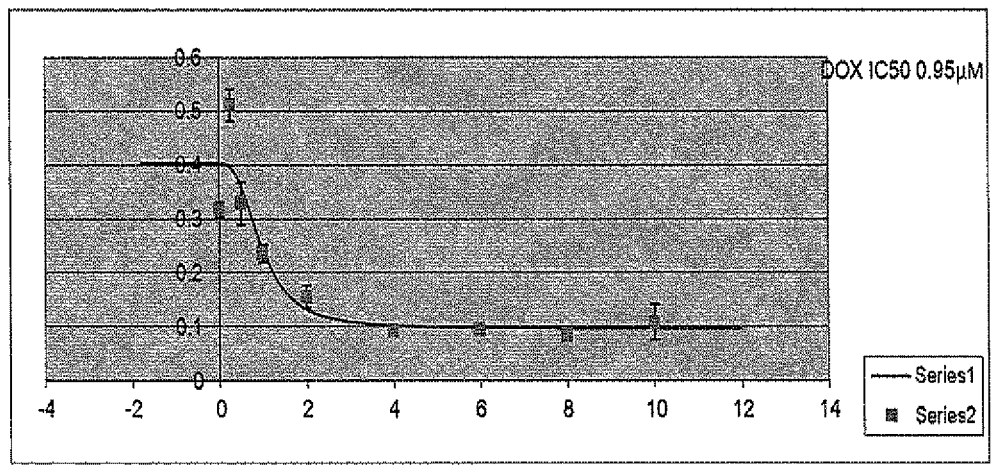
FIGS. 4A-D are dose response curves for doxorubicin and compounds 3a, 4i, and 6g against HeK cells.
Figure 4B:
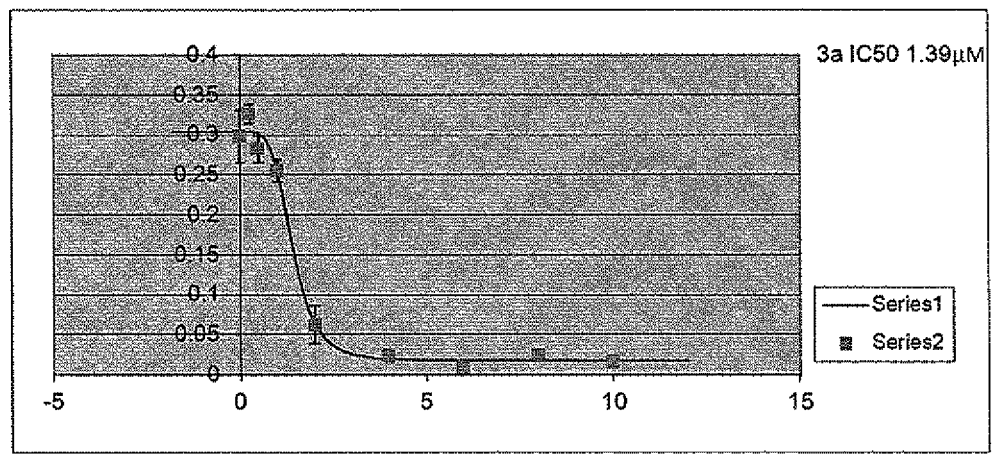
Figure 4C:
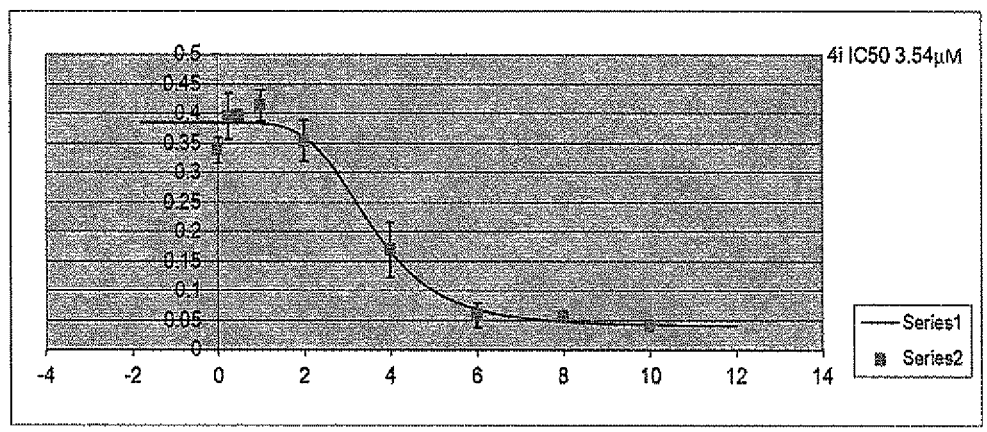
Figure 4D:
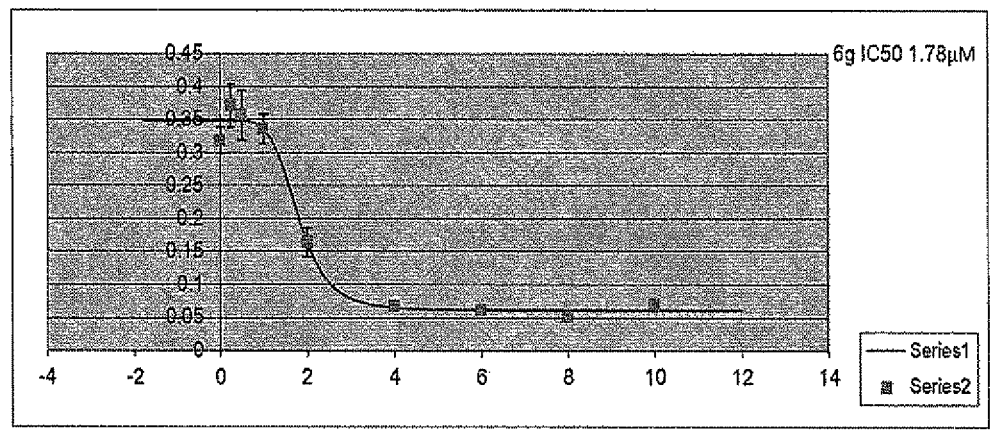

Curcumin analogs (3a-j, 4a-j, 5a-j, 6a-j), (Table 1a) were first screened for their cytotoxicity against HeLa cells using the MTT assay at 50 μM (FIG. 1). Promising candidates ($OD_{490}$<0.14) were selected for further screening at 20 μM and 2 μM (FIG. 2). Then the top five active compounds were examined for their $IC_{50}$ on HeLa and Hek cell lines. From the cytotoxicity data, it is clear that substitution on the nitrogen of piperidone with p-toluene sulfonyl (p-Ts), benzene sulfonyl (BS), or ethyl ($CH_2CH_3$) do not play any significant role in cytotoxicity. For example, 3a, 4e, and 6g showed very good activity though the substitutions are different. However, substitutions on the aromatic ring could lead to significant differences in $IC_{50}$ values. Compounds having p-methyl, p-ethyl, p-propyl, and p-isopropyl groups (3b-d, 3i, 4a-d, 5a, 5c-d, 6d) in the aromatic ring showed better effect compared with substitutions on the phenyl ring with bulky groups (3g-h, 4g, 5g, 6h-i) such as p-butyl and p-tert-butyl group (FIG. 2). Among all the tested compounds, halogen group substitution on the para position, such as p-chloro, p-bromo, and p-fluoro (3a, 3j, 4e, 4i-j, 5b, 5i-j, 6a-c) tends to confer improved inhibition activity. For example, four of the most active compounds 3a, 3j, 4e, and 4i with $IC_{50}$ values between 0.3-1.5 uM are halogen-containing. Compounds having electron donating groups showed poor anticancer activity except compound 6g, which showed excellent anticancer activity with $IC_{50}$ lower than 1 uM against HeLa cancer cell lines (FIGS. 2 and 3). Five of the most active compounds 3a, 3j, 4e, 4i and 6g were also tested against the Hek cell lines and these compounds exhibited excellent cytotoxicity (IC50=1.24-3.54 μM) (FIG. 4, Table 5). As a comparison, doxorubicin had an $IC_{50}$ of 2.89 μM in HeLa and 0.95 μM in Hek cell lines.

TABLE 5

| | $IC_{50}$ (μM) | | | | |
|---|---|---|---|---|---|
| Cell line | 3a | 3j | 4e | 4i | 6g |
| Hela | 0.28 | 0.61 | 0.85 | 1.44 | 0.86 |
| HEK | 1.39 | 1.24 | 1.97 | 3.54 | 1.78 |

Activity for compounds SR13-17, SR 34, and SR36-40 against HeLa, KB, DU145, and PC3 cell lines is shown in Table 6.

Figure 5:
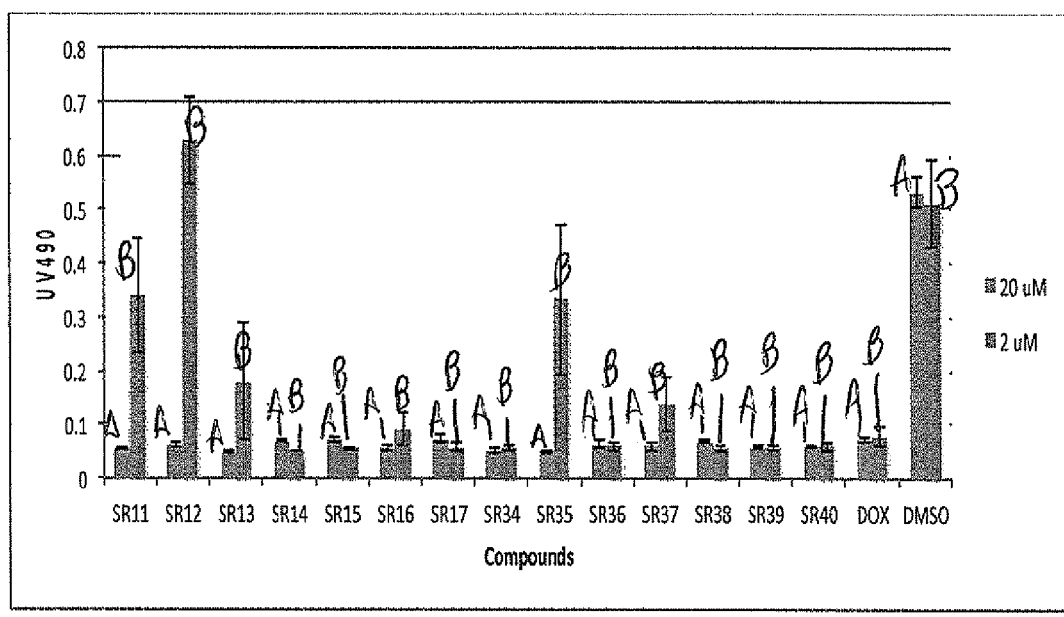
FIG. 5 is a bar graph showing the cytotoxicity (fraction of cell survival) of curcumin analogs SR11-17, SR35-40, and SR 43 in Hela cells using the MTT assay at 50 µM. Data represent average values of three replicates.

Similarly, anticancer activity of C5-curcuminoid-triazole conjugates with their alkyne counterpart (SR11-SR17 and SR34-SR40) was also evaluated against HeLa cells. As shown in FIG. 5, most of these compounds showed good activity. Therefore, $IC_{50}$ values were determined by using four different cell lines (Table 5).

Figures 6A, 6B, 6C:
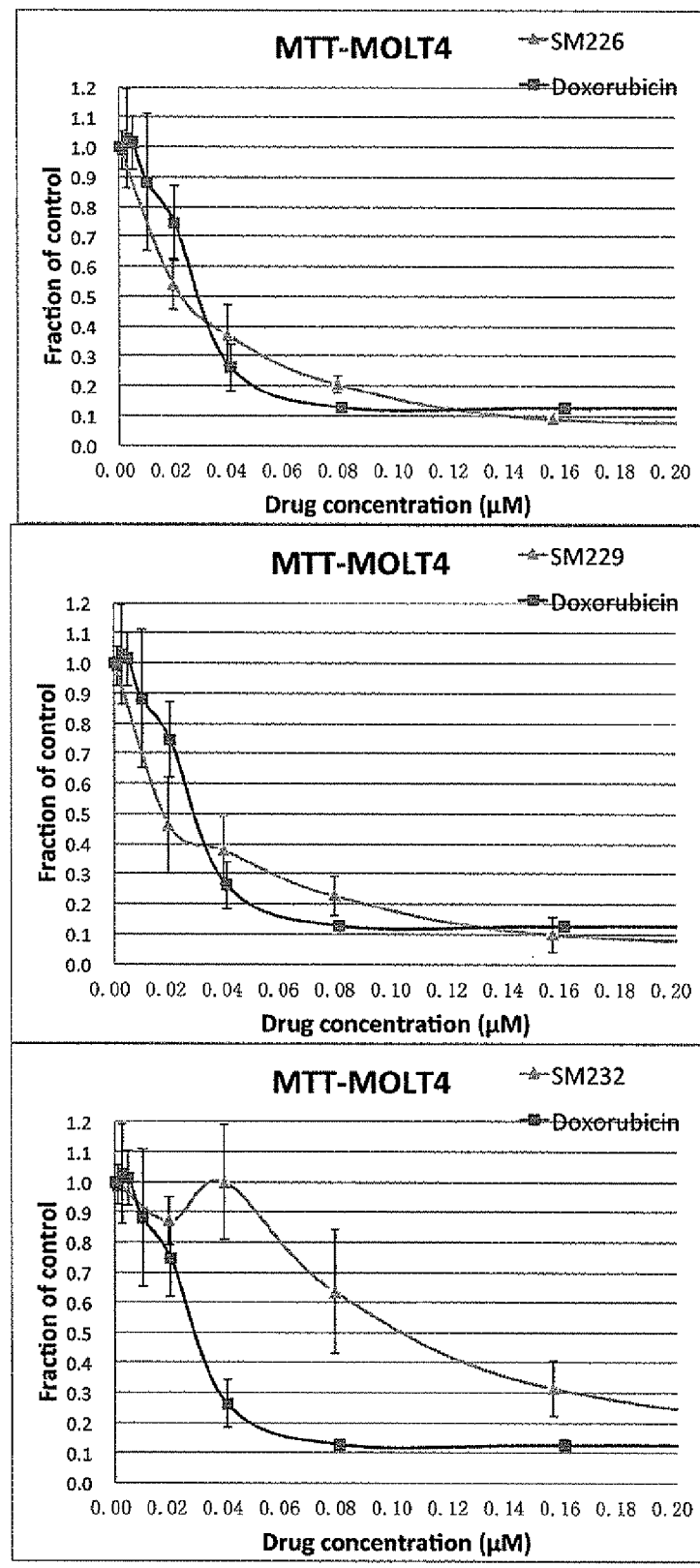
FIGS. 6A-6C are line graphs comparing the activity of SM226 (FIG. A), SM 229 (FIG. B), and SM 232 (FIG. C) with doxorubicin against MOLT 4 cell line as a function of drug concentration (micromolar).
Figures 7A, 7B, 7C:
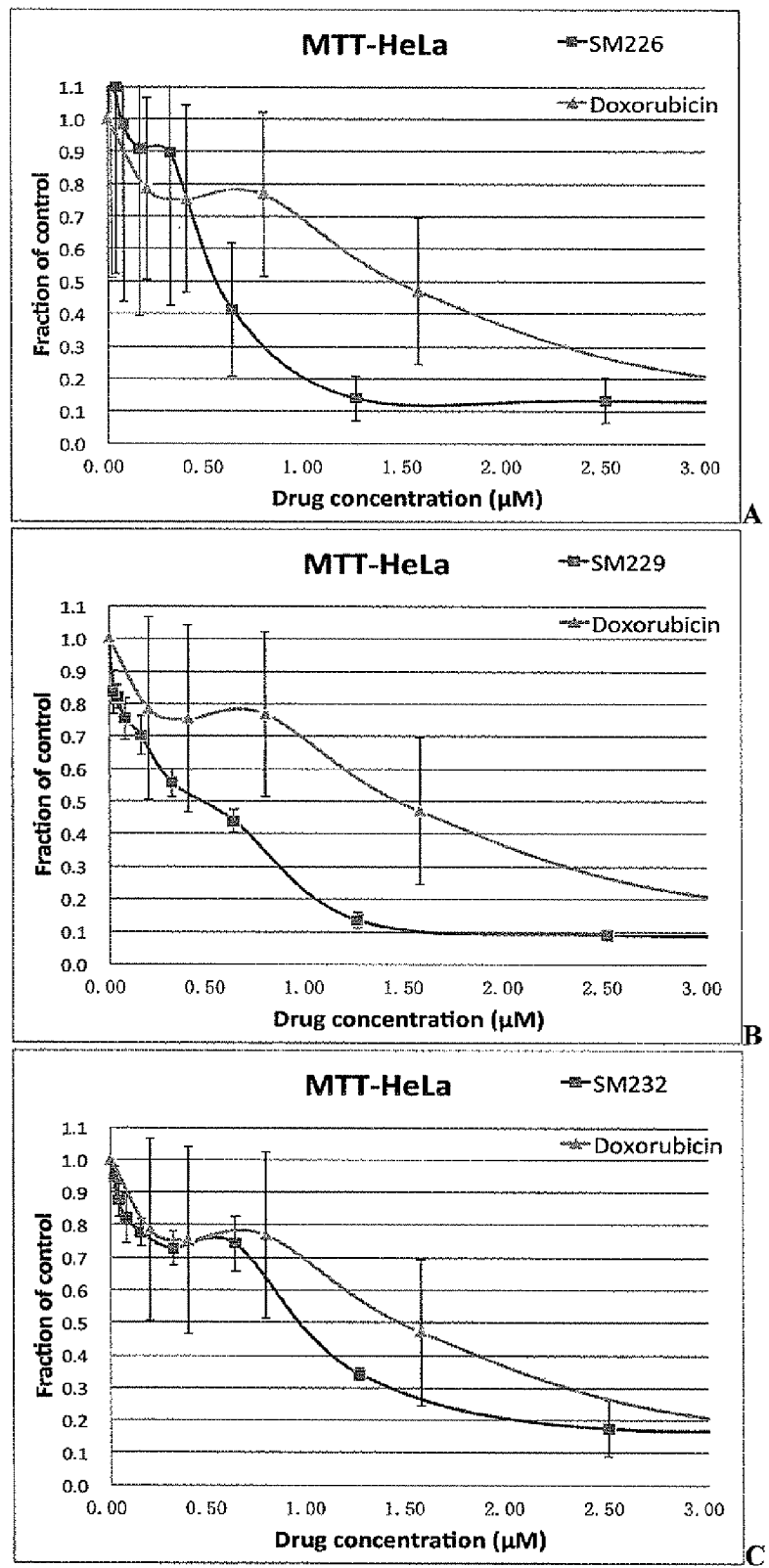
FIGS. 7A-7C are line graphs comparing the activity of SM226 (FIG. A), SM 229 (FIG. B), and SM 232 (FIG. C) with doxorubicin against HeLa cell line as a function of drug concentration (micromolar).

Anticancer activity of compounds SM226, SM229, and SM232 compared to doxorubicin against MOLT 4 and HeLa cell lines as a function of drug concentration (micromolar) is shown in FIGS. 6 and 7.

We claim:

1. A compound of Formula II:

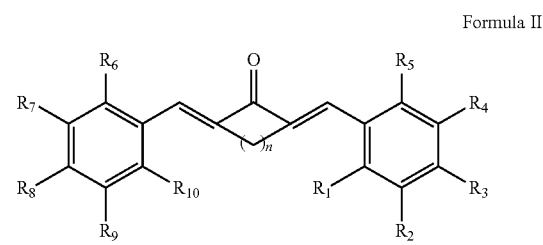

Formula II wherein, $R_1$, $R_2$, $R_4$, $R_5$, $R_6$, $R_7$, $R_9$, and $R_{10}$ are independently absent or selected from the group consisting of substituted or unsubstituted, linear, branched, or cyclic alkyl, alkenyl, or alkynyl, halogen, substituted or unsubstituted aryl or heteroaryl, substituted or unsubstituted alkoxy, hydroxy, cyano, formyl, acyl, carboxylic acid, carboxylate, primary amide, secondary amide, tertiary amide, secondary carbamate, tertiary carbamate, urea, carbinol, ester, thiol, primary amine, secondary amine, tertiary amine, thioether, sulfinyl group, sulfonyl group;

wherein, n=0, 2, 3, or 4;

$R_3$ and $R_8$ are —$O(CH_2)_mX$, wherein m is an integer from 0-10 and X is a halogen, or an aromatic or non-aromatic heterocyclic ring selected from the group consisting of:

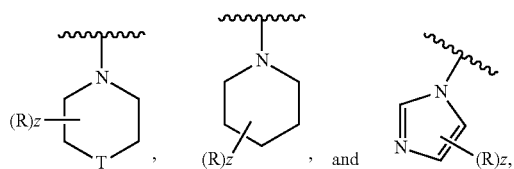

wherein each occurrence of R is independently absent or selected from the group consisting of substituted or unsubsti-

TABLE 6

| Compounds | SR13 | SR14 | SR15 | SR16 | SR17 | SR34 |
|---|---|---|---|---|---|---|
| HeLa cell | 5.3 ± 2.8 | 2.7 ± 1.3 | 2.1 ± 0.35 | 2.2 ± 0.93 | 2.5 ± 1.2 | 2.8 ± 0.93 |
| KB cell | 3.7 ± 0.21 | 1.2 ± 0.32 | 3 ± 0.31 | 2.6 ± 0.41 | 4.3 ± 2.4 | 4.7 ± 1.1 |
| DU145 cell | 6.5 ± 3.0 | 6.6 ± 4.6 | 3.1 ± 1.3 | 3.7 ± 2.4 | 9.6 ± 7.3 | 4.0 ± 0.49 |
| PC3 cell | 3.7 ± 2.1 | 1.5 ± 0.24 | 3.1 ± 1.8 | 2.0 ± 0.05 | 2.8 ± 0.80 | 2.7 ± 0.80 |
| Compounds | SR36 | SR37 | SR38 | SR39 | SR40 | Doxorubicin |
| HeLa cell | 2.0 ± 1.2 | 5.0 ± 2.2 | 2.5 ± 1.3 | 2.6 ± 1.4 | 1.8 ± 0.65 | 0.96 ± 0.27 |
| KB cell | 1.5 ± 0.30 | 4.7 ± 0.87 | 2.1 ± 0.05 | 2.6 ± 0.69 | 1.8 ± 0.29 | 0.4 ± 0.11 |
| DU145 cell | 1.9 ± 0.59 | 6.7 ± 1.9 | 6.7 ± 4.4 | 5.3 ± 2.8 | 1.9 ± 0.62 | 0.47 ± 0.25 |
| PC3 cell | 1.7 ± 0.24 | 11.0 ± 2.7 | 2.6 ± 0.4 | 3.0 ± 0.75 | 1.8 ± 0.68 | 0.23 ± 0.01 | tuted, linear, branched, or cyclic alkyl, alkenyl, or alkynyl, halogen, substituted or unsubstituted aryl or heteroaryl, substituted or unsubstituted alkoxy, hydroxy, cyano, formyl, acyl, carboxylic acid, carboxylate, primary amide, secondary amide, tertiary amide, secondary carbamate, tertiary carbamate, urea, carbinol, ester, thiol, primary amine, secondary amine, tertiary amine, thioether, sulfinyl group, sulfonyl group;

T is O, S, or NR$_{13}$, wherein each occurrence of R$_{13}$ is independently absent or selected from the group consisting of substituted or unsubstituted, linear, branched, or cyclic alkyl, alkenyl, or alkynyl; halogen, substituted or unsubstituted aryl or heteroaryl; substituted or unsubstituted alkoxy; hydroxy, cyano, formyl, acyl, carboxylic acid, carboxylate, primary amide, secondary amide, tertiary amide, secondary carbamate, tertiary carbamate, urea, carbinol, ester, thiol, primary amine, secondary amine, tertiary amine, thioether, sulfinyl group, sulfonyl group; and z, as valence permits, is an integer from 0-10.

2. The compound of claim 1, wherein at least one of R$_1$-R$_2$, R$_4$-R$_5$ and at least one of R$_6$-R$_7$, R$_9$-R$_{10}$ are halogen.

3. The compound of claim 1, wherein at least one of R$_1$, R$_2$, R$_4$, or R$_5$ and at least one of R$_6$, R$_7$, R$_9$, or R$_{10}$ are unsubstituted alkyl.

4. The compound of claim 1, wherein at least one of R$_1$, R$_2$, R$_4$, or R$_5$ and at least one of R$_6$, R$_7$, R$_9$, or R$_{10}$ are unsubstituted alkoxy.

5. The compound of claim 1, wherein n is 2 or 3; and R$_2$ and R$_9$ are other than hydrogen.

6. The compound of claim 5, wherein R$_2$ and R$_9$ are lower alkoxy groups.

7. The compound of claim 1, wherein the compound is:

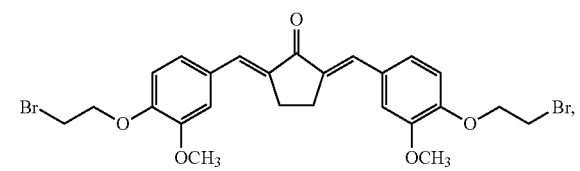

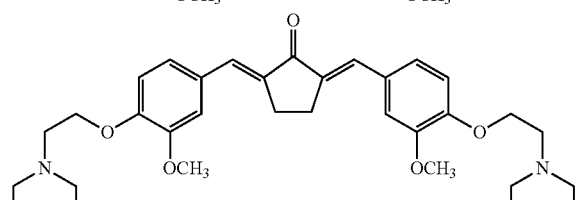

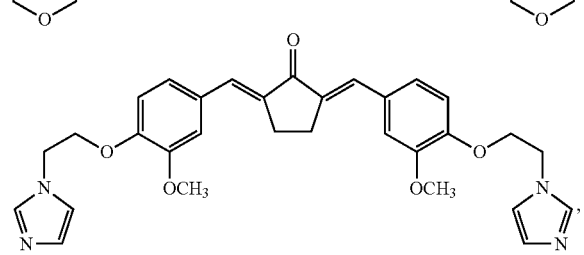

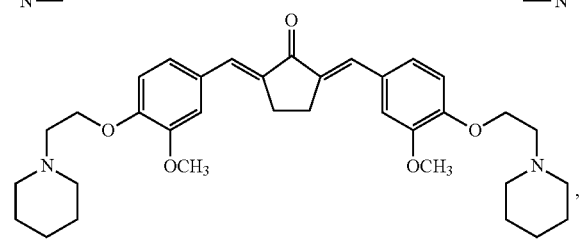

-continued or

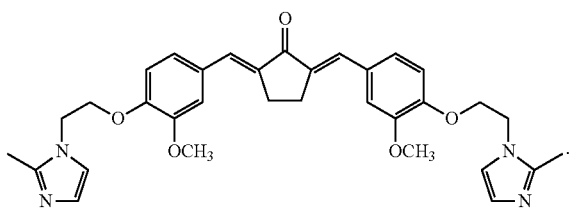

8. A pharmaceutical composition comprising the compound of claim 1 and a pharmaceutically acceptable carrier.

9. The composition of claim 8, wherein the carrier is suitable for enteral administration.

10. The composition of claim 9, wherein the carrier is suitable for oral administration.

11. The composition of claim 10, wherein the composition is the form of a tablet, soft capsule, hard capsule, caplet, solution, or suspension.

12. The composition of claim 8, wherein the carrier is suitable for parenteral administration.

13. The composition of claim 12, wherein the composition is in the form of a solution or suspension.

14. A method of treating a proliferative disorder in a patient in need thereof, the method comprising administering one or more compounds of claim 1.

15. The method of claim 14, wherein the proliferative disorder is cancer.

16. The compound of claim 5, wherein R$_2$, R$_9$, or both are methoxy.

17. A compound, wherein the compound is:

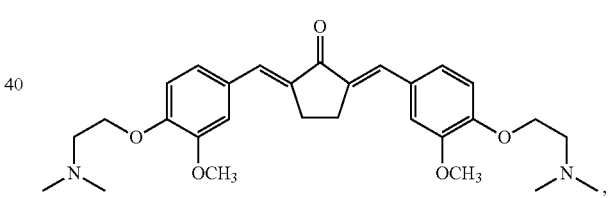

18. A compound of Formula I:

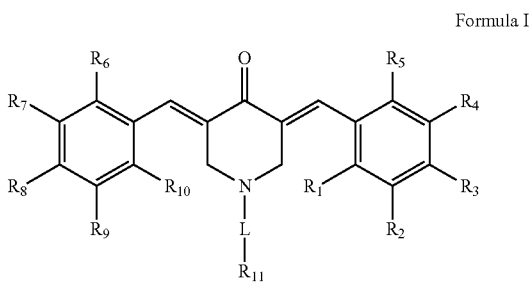

Formula I wherein, L comprises a sulfonyl or substituted heteroaryl group, wherein, R$_1$, R$_2$, R$_3$, R$_4$, R$_5$, R$_6$, R$_7$, R$_8$, R$_9$, and R$_{10}$ are independently absent or selected from the group consisting of substituted or unsubstituted, linear, branched, or cyclic alkyl, alkenyl, or alkynyl, halogen, substituted or unsubstituted aryl or heteroaryl, substituted or unsubstituted alkoxy, hydroxy, cyano, formyl, acyl, carboxylic acid, carboxylate, primary amide, secondary amide, tertiary amide, secondary carbamate, tertiary carbamate, urea, carbinol, ester, thiol, primary amine, secondary amine, tertiary amine, thioether, sulfinyl group, sulfonyl group;

wherein, $R_{11}$ is substituted or unsubstituted alkyl, cycloalkyl, alkenyl, cycloalkenyl, or alkynyl, substituted or unsubstituted benzyl, substituted or unsubstituted aryl, substituted or unsubstituted heteroaryl;

with the proviso that:
(a) when L comprises a sulfonyl, and $R_{11}$ is substituted with a halogen, $R_3$ and $R_8$ are independently linear, branched, or cyclic alkyl, alkenyl, or alkynyl, substituted or unsubstituted aryl or heteroaryl, substituted or unsubstituted alkoxy, hydroxy, cyano, formyl, acyl, carboxylic acid, carboxylate, primary amide, secondary amide, tertiary amide, secondary carbamate, tertiary carbamate, urea, carbinol, ester, thiol, primary amine, secondary amine, tertiary amine, thioether, sulfinyl group, sulfonyl group;
(b) when L comprises a sulfonyl, and $R_{11}$ is substituted with an alkoxy, $R_4$ and $R_7$ are independently substituted or unsubstituted, linear, branched, or cyclic alkyl, alkenyl, or alkynyl, halogen, substituted or unsubstituted aryl or heteroaryl, substituted or unsubstituted alkoxy, hydroxy, cyano, formyl, acyl, carboxylic acid, carboxylate, primary amide, secondary amide, tertiary amide, secondary carbamate, tertiary carbamate, urea, carbinol, ester, thiol, primary amine, secondary amine, tertiary amine, thioether, sulfinyl group, sulfonyl group; or
(c) when L comprises a sulfonyl, and $R_{11}$ is substituted with an alkyl, $R_1$, $R_{10}$, or both, are not halogen.

19. The compound of claim 18, wherein:
L is a sulfonyl group, and
$R_{11}$ is substituted or unsubstituted alkyl, cycloalkyl, alkenyl, cycloalkenyl, or alkynyl, substituted or unsubstituted benzyl, substituted or unsubstituted aryl, substituted or unsubstituted heteroaryl.

20. The compound of claim 18, wherein L comprises a substituted heteroaryl group.

21. The compound of claim 20, wherein the substituted heteroaryl group is a substituted triazole.

22. A compound having the formula:

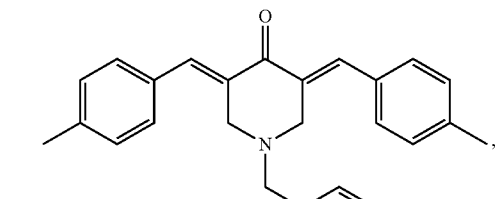,

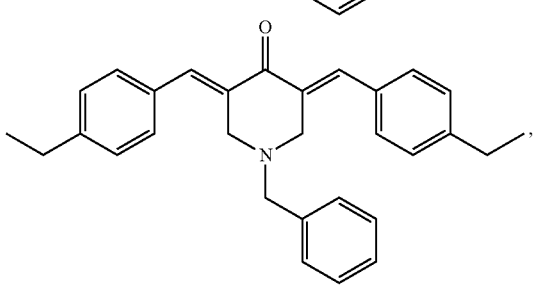,

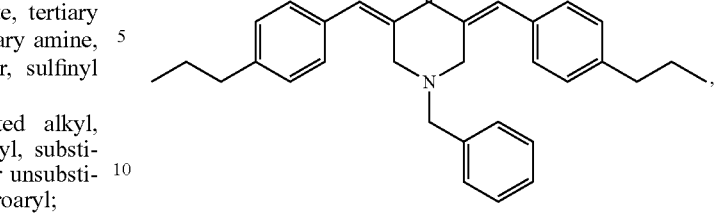,

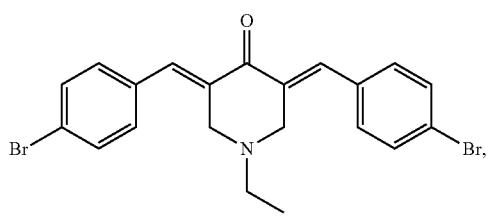,

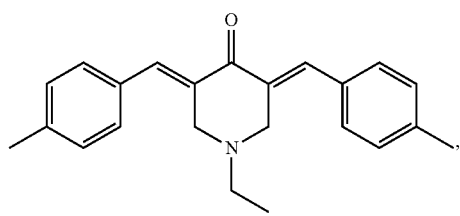,

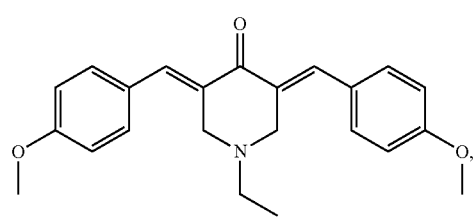,

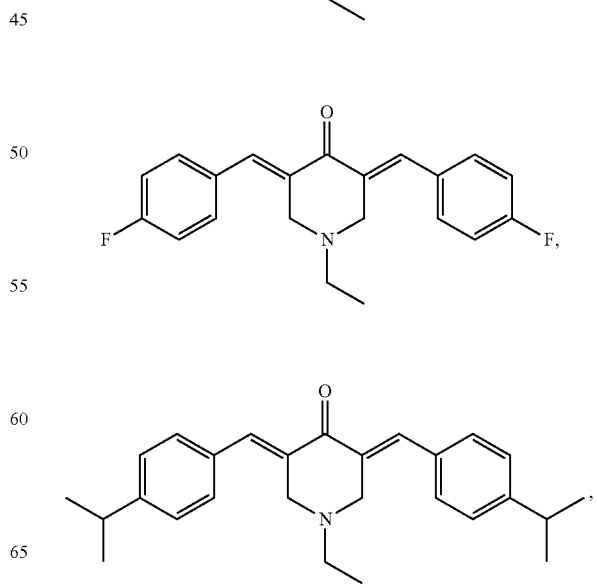

89
-continued
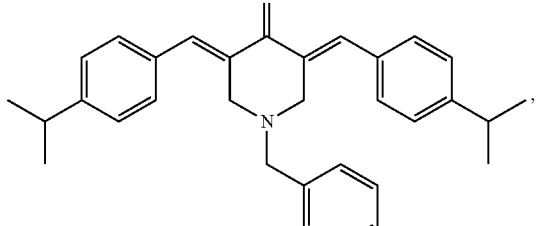
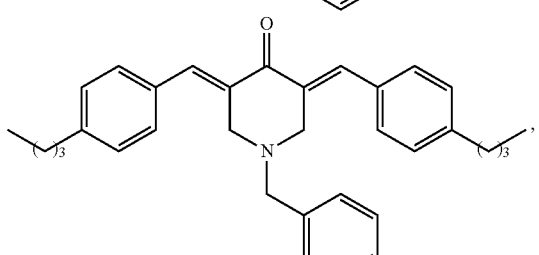
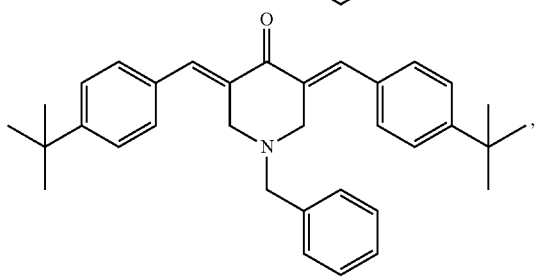
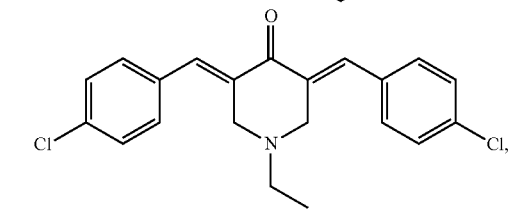
90
-continued
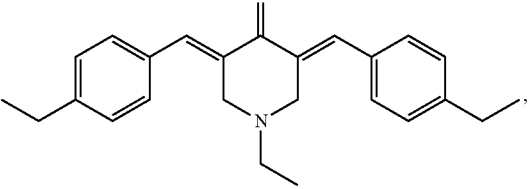
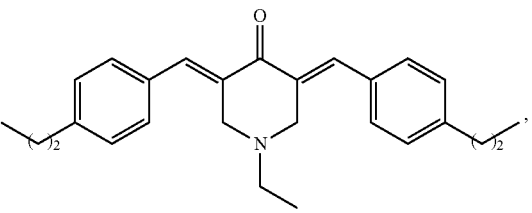
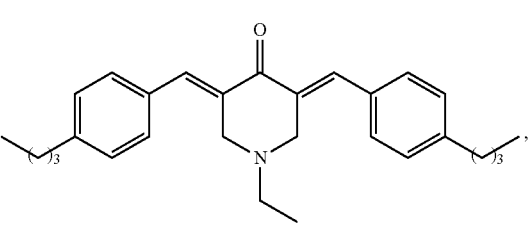
or
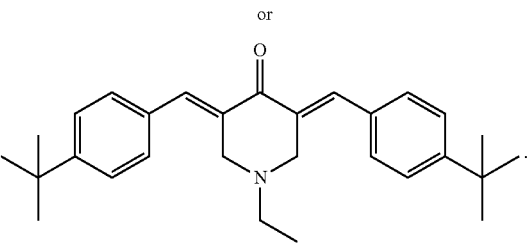
* * * * *